United States Patent
Mandla et al.

(10) Patent No.: US 12,186,420 B2
(45) Date of Patent: Jan. 7, 2025

(54) COMPOSITIONS AND METHODS OF USE FOR TREATMENT OR IMPROVEMENT OF THE CONDITION AND APPEARANCE OF SKIN

(71) Applicants: Quthero, Inc., Miami, FL (US); UTI Limited Partnership, Calgary (CA)

(72) Inventors: Serena Mandla, Toronto (CA); Jeffrey Alan Biernaskie, Calgary (CA); Holly Danielle Sparks, Rockey View County (CA); William Michael Scott, Longview (CA); Milica Radisic, Toronto (CA)

(73) Assignees: Quthero, Inc., Miami, FL (US); UTI Limited Partnership, Calgary (CA)

( * ) Notice: Subject to any disclaimer, the term of this patent is extended or adjusted under 35 U.S.C. 154(b) by 0 days.

(21) Appl. No.: 18/464,024

(22) Filed: Sep. 8, 2023

(65) Prior Publication Data
US 2024/0082134 A1    Mar. 14, 2024

Related U.S. Application Data

(62) Division of application No. 17/539,132, filed on Nov. 30, 2021, now abandoned.

(60) Provisional application No. 63/119,059, filed on Nov. 30, 2020.

(51) Int. Cl.
*A61K 38/08*    (2019.01)
*A61K 8/64*     (2006.01)
*A61K 9/00*     (2006.01)
*A61P 17/02*    (2006.01)
*A61Q 19/08*    (2006.01)
*C07K 7/08*     (2006.01)
*A61Q 19/00*    (2006.01)

(52) U.S. Cl.
CPC .............. *A61K 8/64* (2013.01); *A61K 9/0014* (2013.01); *A61K 38/08* (2013.01); *A61P 17/02* (2018.01); *A61Q 19/08* (2013.01); *A61Q 19/005* (2013.01)

(58) Field of Classification Search
CPC ........ A61K 8/64; A61K 38/08; A61K 9/0014; C07K 7/06; A61P 17/02; A61Q 19/08; A61Q 19/005
See application file for complete search history.

(56) References Cited

U.S. PATENT DOCUMENTS

2018/0296631 A1*  10/2018  Radisic ................. A61L 26/008

OTHER PUBLICATIONS

Xiao et al., Front. Bioeng. Biotechnol. Conference Abstract: 10th World Biomaterials Congress, Montreal, Canada, May 17-May 22, 2016; published online Mar. 30, 2016. (Year: 2016).*

* cited by examiner

*Primary Examiner* — Julie Ha
(74) *Attorney, Agent, or Firm* — Smart & Biggar LP

(57) ABSTRACT

Compositions, formulations and methods of use thereof for treating, preventing and improving the condition and aesthetic appearance of skin are described. Compositions, formulations and methods of use thereof for treatment of dermis wounds, aged dermis, diseased dermis or damaged dermis are also described. The present compositions and formulations comprise a peptide with an amino acid sequence of QHREDGS (SEQ ID NO: 1) and methods of use thereof.

20 Claims, 46 Drawing Sheets
Specification includes a Sequence Listing.

FIG. 7A
FIG. 7B

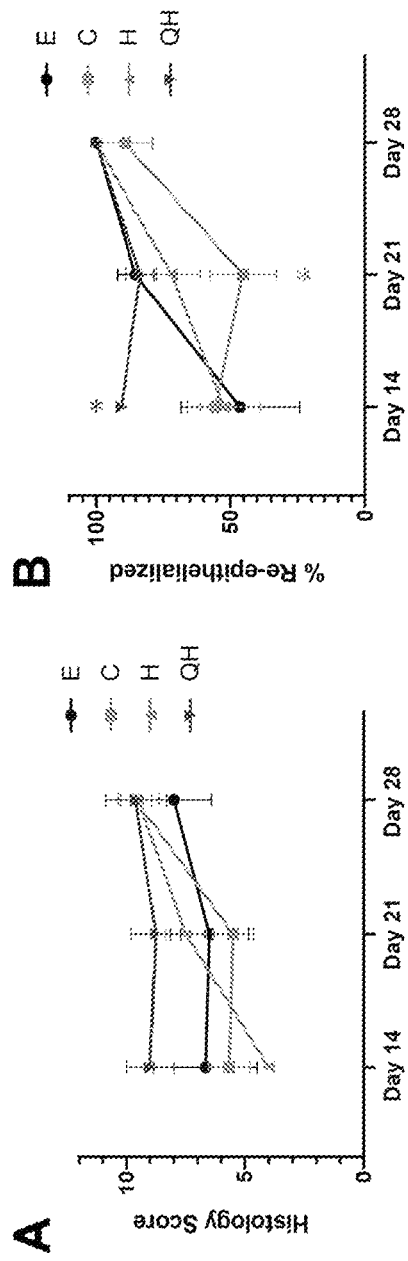
FIG. 10A
FIG. 10B
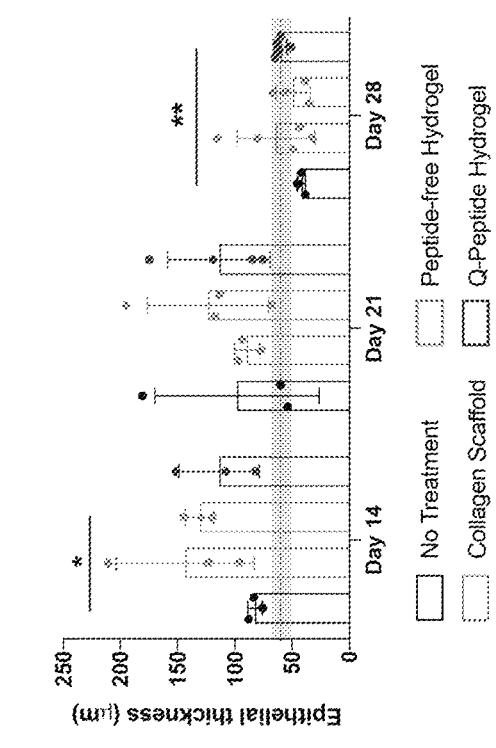
FIG. 10C

FIGS. 16G-16I
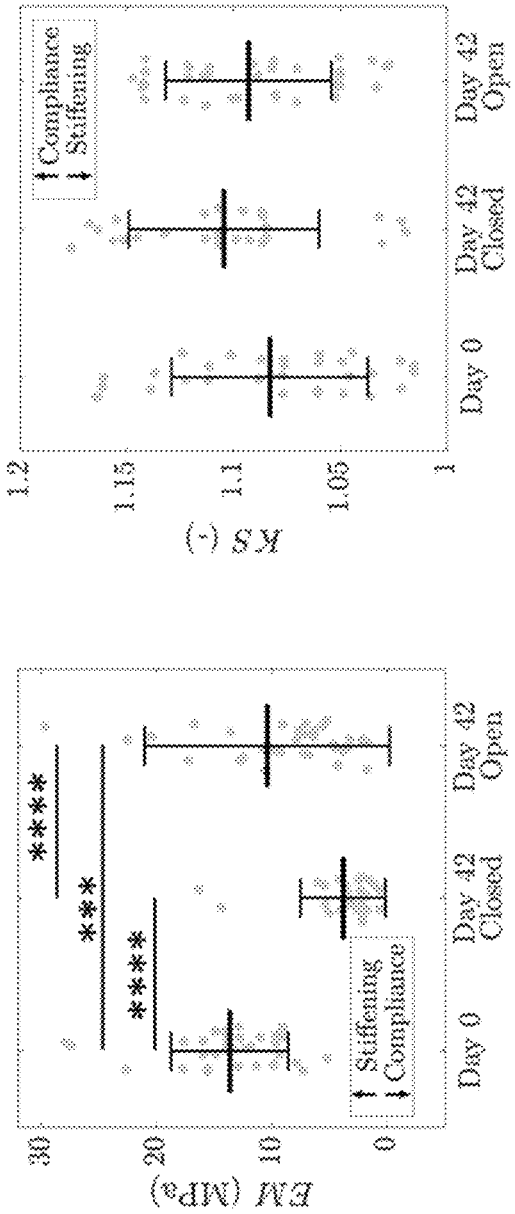
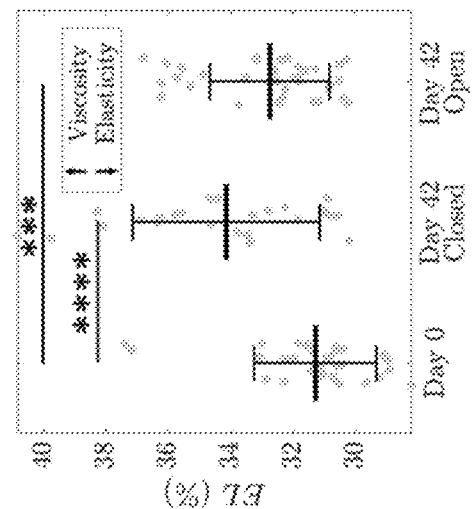

C  Q3: I felt that Kerra made my skin look healthier
100%
Total=12

D  Q4: I felt that Kerra made my skin feel smoother.
91.7%
8.3%
Total=12

E  Q5: I felt that Kerra improved the overall appearance of my skin.
100%
Total=12

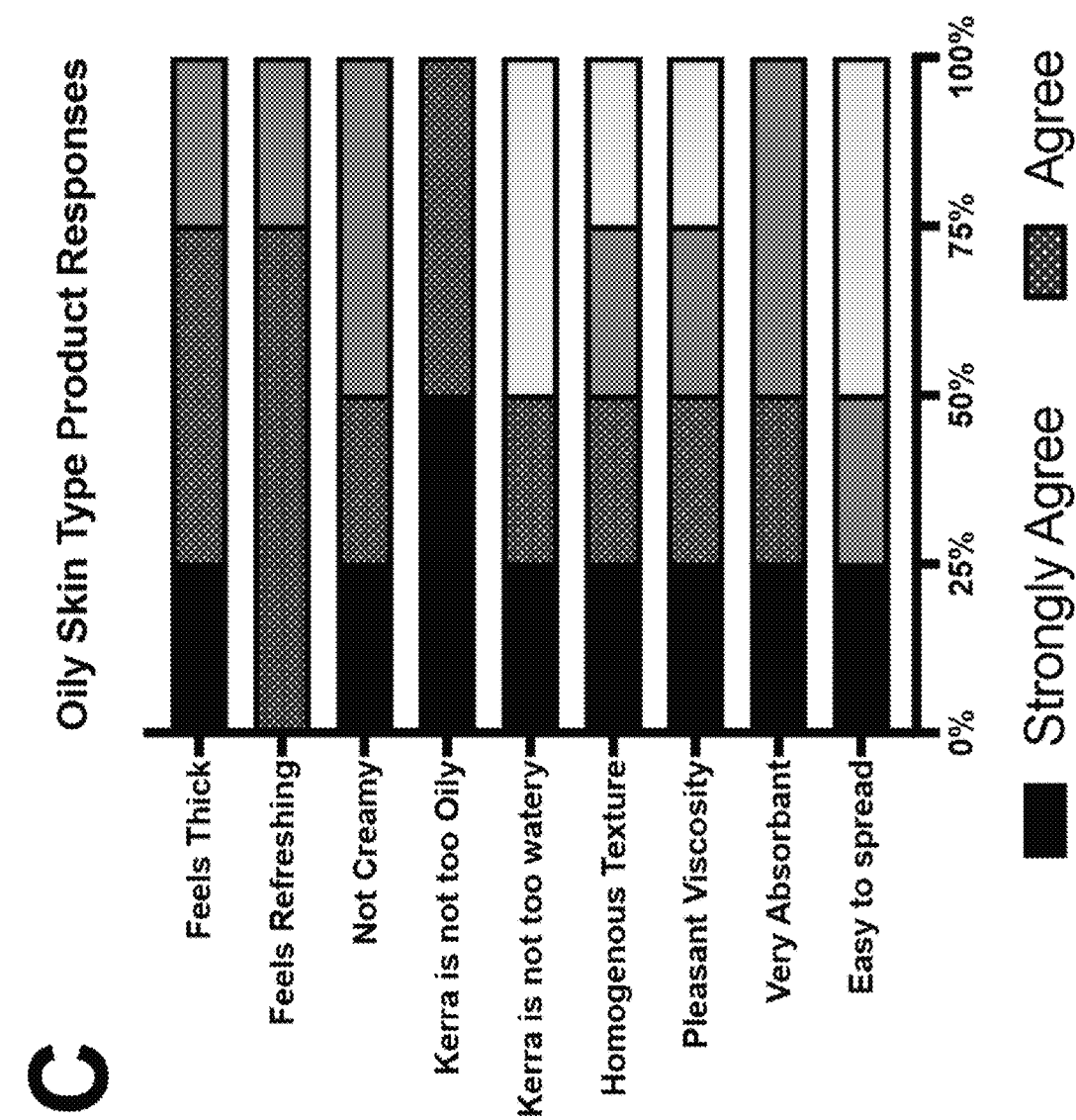

COMPOSITIONS AND METHODS OF USE FOR TREATMENT OR IMPROVEMENT OF THE CONDITION AND APPEARANCE OF SKIN

CROSS-REFERENCE TO RELATED APPLICATIONS

The present disclosure is a divisional of U.S. patent application Ser. No. 17/539,132 filed Nov. 30, 2021, which claims priority from U.S. provisional patent application No. 63/119,059, filed Nov. 30, 2020, the contents of which are hereby expressly incorporated into the present application by reference in their entirety.

INCORPORATION BY REFERENCE OF SEQUENCE LISTING

The contents of the xml file named "Sequence_Listing_56012-3012.xml", which was created on Sep. 15, 2023 and is 31 KB in size, are hereby incorporated by reference in their entireties.

FIELD OF THE INVENTION

The invention relates to compositions, formulations and methods of use thereof for treating, preventing and improving the condition and aesthetic appearance of skin. The invention also relates to compositions, formulations and methods of use thereof for treatment of wounds, such as dermis wounds, aged dermis, diseased dermis or damaged dermis.

BACKGROUND OF THE INVENTION

There is an increasing demand in the cosmetics industry to develop products that may be applied topically to the skin, which improve a condition or the appearance of skin. Subjects are interested in mitigating or delaying the dermatological signs of chronologically or hormonally-aged or photo-aged skin, such as fine lines, wrinkles, and sagging skin, and other conditions. During the aging process, the complexion of the skin, i.e., the color and appearance of the skin, deteriorates slowly from aging and/or exposure to sunlight. Numerous cosmetic and medical treatments have been developed in an attempt to treat aging or aged skin. Such cosmetics or treatments commonly contain organic acids as their active ingredients or components. These actives are frequently associated with subject discomfort, such as burning, itching, and redness.

Therefore, there remains a need for products that retard or counter the aging effects on the skin, and more specifically for products that produce such effects without undesirable side effects. In particular, there remains a need for topically applied cosmetic compositions that have anti-aging and skin texture benefits using peptide components.

Furthermore, there exists a need for new and effective treatments for more extreme skin conditions such as injuries and wounds, in particular full thickness wounds, dermis wounds, aged dermis, diseased dermis or damaged dermis. Numerous cosmetic and medical treatments have been developed in an attempt to treat wounds and promote healing. However, these active ingredients and components are frequently associated with scarring of the skin. Therefore, there exists a need for new compositions and formulations that promote healed wounds, substantially free of scars.

SUMMARY OF INVENTION

The present disclosure provides a method of treating or improving a condition or aesthetic appearance of skin on a subject in need thereof, the method comprising topically administering to the skin a formulation comprising a peptide comprising an amino acid sequence of QHREDGS (SEQ ID NO: 1), in an amount effective to treat or improve the condition or aesthetic appearance of the skin.

In some embodiments, the topical administration is for treating a wound on the subject, the formulation being topically administered to the wound, and the amount of the formulation administered being effective to treat the wound, wherein the wound is a dermis wound, an aged dermis, or a diseased dermis or damaged dermis.

In some embodiments, the method results in a healed wound substantially free of scars. In some embodiments, the dermis wound is selected from the group consisting of a surgical wound, a cosmetic wound, a burn wound, an accidental wound or a self-inflicted wound and any combinations thereof. In some embodiments, the surgical wound is a deep incisional wound or a superficial incisional wound. In some embodiments, the cosmetic wound is ablative fractional or non-fractional laser wound or a microneedling wound. In some embodiments, the burn wound is a sunburn, a radiation burn, an open blister or a peeling wound.

In some embodiments, the topical administration is for improvement of the condition or aesthetic appearance of the skin, and the improvement of the condition or aesthetic appearance of skin is at least one of: reducing dermatological signs of chronological aging, photo-aging, hormonal aging, and/or actinic aging; preventing and/or reducing the appearance of lines and/or wrinkles; reducing the noticeability of facial lines and wrinkles, facial wrinkles on the cheeks, forehead, perpendicular wrinkles between the eyes, horizontal wrinkles above the eyes, and around the mouth, marionette lines, and particularly deep wrinkles or creases; preventing, reducing, and/or diminishing the appearance and/or depth of lines and/or wrinkles; improving the appearance of suborbital lines and/or periorbital lines; reducing the appearance of crow's feet; rejuvenating and/or revitalizing skin, particularly aging skin; reducing skin fragility; preventing and/or reversing of loss of glycosaminoglycans and/or collagen; ameliorating the effects of estrogen imbalance; preventing skin atrophy; preventing, reducing, and/or treating hyperpigmentation; minimizing skin discoloration; improving skin tone, radiance, clarity and/or tautness; preventing, reducing, and/or ameliorating skin sagging; improving skin firmness, plumpness, suppleness and/or softness; improving procollagen and/or collagen production; improving skin texture and/or promoting retexturization; improving skin barrier repair and/or function; improving the appearance of skin contours; restoring skin luster and/or brightness; minimizing dermatological signs of fatigue and/or stress; resisting environmental stress; replenishing ingredients in the skin decreased by aging and/or menopause; improving communication among skin cells; increasing cell proliferation and/or multiplication; increasing skin cell metabolism decreased by aging and/or menopause; retarding cellular aging; improving skin moisturization; enhancing skin thickness; increasing skin elasticity and/or resiliency; enhancing exfoliation; improving microcirculation; or decreasing and/or preventing cellulite formation.

In some embodiments, dermatological sign of chronological aging is selected from a group consisting of rhytids, wrinkles, jowls, sun damage, dull appearance of skin, loss of skin tautness, keratosis, hyperpigmentation, melasma, solar lentigo, solar keratosis, dermatoheliosis, skin discoloration, and any combinations thereof.

In some embodiments, the topical administration is for improvement of the condition or aesthetic appearance of the skin, and the improvement of the condition or aesthetic appearance of skin is regenerating collagen in a skin area of the subject, the amount of formulation administered being effective to regenerate collagen in the skin area.

In some embodiments, the subject has wrinkles in the skin area. In some embodiments, the skin area is susceptible to developing wrinkles. In some embodiments, the skin area is on a forehead, on a cheek, on a neck, around an eye of the subject, or any combination thereof. In some embodiments, the subject has skin redness in the skin area.

In some embodiments, the topical administration is for improvement of the condition or aesthetic appearance of the skin, and the improvement of the condition or aesthetic appearance of skin is preventing or decreasing wrinkles in the subject the amount of formulation administered being effective to prevent or decrease wrinkles.

In some embodiments, the topical administration is for improvement of the condition or aesthetic appearance of the skin, and the improvement of the condition or aesthetic appearance of skin is decreasing skin redness in the subject the amount of formulation administered being effective to decrease skin redness.

In some embodiments, the skin redness results from acne, contact irritation, skin sensitivity, rosacea, eczema, surgery, laser treatment, allergies, microdermabrasion, dermabrasion or any combination thereof.

In some embodiments, the formulation of the present disclosure further comprises a topically acceptable vehicle.

In some embodiments, the topically acceptable vehicle is selected from hydroxyethyl cellulose, hydroxypropyl cellulose, methylcellulose, hydroxypropyl methylcellulose, sodium hyaluronate, hyaluronic acid, sodium carbomer, aloe gel, xanthan gum, cetyl alcohol, cetearyl alcohol, propanediol 1,3 glycerin, rosehip oil, shea butter, jojoba oil, castor oil, macadamia oil, argan oil, kukui nut oil, petrolatum, mineral oil, evening primrose oil, glyceryl stearate, Polysorbate 60, Cetearyl Olivate, Sorbitan Olivate, Sodium Stearyl Lactylate, Stearic Acid, PEG 100 Stearate, Benzyl Alcohol, Ethylhexylglycerin, Benzoic Acid, Sorbic Acid, Gluconolactone, Sodium Benzoate, Calcium Gluconate and any combinations thereof.

In some embodiments, the formulation of the present disclosure further comprises a carrier. In some embodiments, the peptide is conjugated to the carrier.

In some embodiments, the carrier is selected from a group consisting of: hydrogel, glycerol, propylene glycol, polyethylene glycol, chitosan, alginate, agarose, polyethers, polyesters, methylcellulose, hyaluronan, collagen, laminin, matrigel, fibronectin, vitronectin, poly-1-lysine, proteoglycans, fibrin glue, gels made by decellularization of engineered and natural tissues, polyglycolic acid (PGA), polylactic acid (PLA) and combinations of PGA and PLA such as PLGA, poly c-caprolactone, polyvinyl alcohol (PVA), polyethylene glycol (PEG), methyl methacrylate, poly(methyl methacrylate) (PMMA), poly(2-hydroxyethyl methacrylate) (PolyHEMA), poly(glycerol sebacate), self-assembling peptide hydrogels, AcN-RARADADARARADADA-CNH (SEQ ID NO: 2), polyurethanes, poly(isopropylacrylamide), poly(N-isopropylacrylamide) [poly(NIPAM)], and any combinations thereof. In some embodiments, the carrier comprises a hydrogel. In some embodiments, the carrier further comprises chitosan.

In some embodiments, the formulation comprises 0.5-50 wt % carrier. In some embodiments, the formulation comprises 0.001-1 wt % peptide. In some embodiments, the formulation further comprises collagen. In some embodiments, the formulation comprises 0.02-2 wt % collagen.

In some embodiments, the formulation is in the form of a gel, a tincture, a cream, an ointment, a lotion, or an aerosol spray.

In some embodiments, the formulation is delivered on a patch or a bandage.

In some embodiments, the subject is a mammal. In some embodiments, the mammal is selected from a human, a horse, a dog, a cat, a pig, and a cow. In some embodiments, the subject is a non-mammal.

The present disclosure also provides a use of a formulation for treating or improving a condition or aesthetic appearance of skin on a subject in need thereof, the use comprising topically administering the formulation to the subject in an amount effective to treat or improve the condition or aesthetic appearance of the skin, the formulation comprising a peptide comprising an amino acid sequence of QHREDGS (SEQ ID NO: 1).

The present disclosure further provides a formulation for treating or improving a condition or aesthetic appearance of skin on a subject in need thereof by topically administering the formulation to the subject in an amount effective to treat or improve the condition or aesthetic appearance of the skin, the formulation comprising a peptide comprising an amino acid sequence of QHREDGS (SEQ ID NO: 1).

BRIEF DESCRIPTION OF THE DRAWINGS

FIG. 2A shows a quantification of tissue compaction over time. Tissue area was quantified using ImageJ. Within the first 7 hours, tissues made with the Q-Peptide hydrogel compacted significantly slower compared to the Peptide-Free hydrogel. FIG. 2B is a survival curve showing the percent of intact tissues over a period of seven days.

FIGS. 7A and 7B are a series of graphs showing the passive tension of Q-Peptide Hydrogel tissues compared to Peptide-Free hydrogel tissues in an example of the present disclosure. FIG. 7A shows the passive tension after 24 hours N=12-17. FIG. 7B shows the passive tension after 7 days N=3. * P<0.05.

FIG. 9A shows wound appearance was scored using a wound closure score where open wounds=0, closed wound attached eschar (scab)=0.5, and closed wound, no eschar=1. Q-peptide treated wounds showed significantly improved wound score across on day 28. FIG. 9B shows measurement of the change in overall graft area after 28 days indicated significantly less healing occurred through wound contraction of Q-peptide treated wounds compared with peptide-free hydrogel and Primatrix®. Data are presented as mean±SD. Scale bar 500 mm. *=p<0.05, **=p<0.01. N=3-5

FIGS. 10A-10C show histology of healing wounds and accelerated wound re-epithelialization with Q-peptide hydrogel treatment in an example of the present disclosure. FIG. 10A—Representative Hemotoxylin and Eosin stained sections from the middle of wounds at 14, 21, and 28 days post wounding (DPW). Qualitative histology scoring (1-12, with higher scores indicating greater granulation tissue filling, re-epithelialization, and reduction of cellular infiltration) shows a trend (p=0.09) toward faster and more complete wound healing following treatment with Q-peptide hydrogel. FIG. 10B shows that significantly faster re-epithelialization of wounds treated with Q-peptide hydrogel was observed at earlier timepoints (days 14 and 21).

FIG. 10C—Measurement of epithelial thickness in healing wounds revealed thickening of neoepidermis in all groups at early timepoints (day 14 and 21) compared with uninjured human skin (dashed line+/−area shaded in grey). Treatment with Q-peptide hydrogel promoted more complete return to pre-injury epidermal thickness by day 28 compared with no treatment control. *=p<0.05, *=significantly less than, p<0.05. E=No treatment, P=Primatrix®, H=Peptide-free hydrogel, QH=Q-peptide hydrogel N=3-5

FIG. 11A—Quantification of blood vessel density as a % of total area shows increased neovascularization in Q-peptide treated wounds relative to no treatment and Primatrix®. FIG. 11B—Quantification of blood vessel diameter shows no significant difference across treatment groups. FIG. 11C shows the aSMA score and FIG. 11D shows CD31 staining score in extravascular structures. Data are presented as mean±SEM. *=p<0.05 E=No treatment, P=Primatrix®, H=Peptide free Hydrogel, QH=Q-peptide Hydrogel n=3.

FIG. 14A shows an odified orientation (two vertically arranged wounds dorsomedially ("medial") and dorsolaterally ("lateral") on both forelimbs) of wounds. E=No treatment, H=peptide-free hydrogel, QH=Q-peptide hydrogel, and RQH=Q-peptide hydrogel (repeated application). FIG. 14B shows an experimental timeline. Colored boxes represent relevant wound locations. FIG. 14C shows prefabricated hydrogel bandages provided ease of application in a field setting. FIG. 14D shows representative specimens of excised intact skin (Day 0) and excised wounds (Day 42) for mechanical testing. Markers placed on the tissue allowed for measurement of deformation. FIG. 14E shows biaxial tensile device. Directions (11) and (22) are along and perpendicular to hair growth, respectively. Blue and red arrows indicate how forces are applied. FIGS. 14F-14H shows derivation of effective mechanical properties from stress-deformation curves the energy loss (EL) characterizing tissue viscoelasticity, the knee stretch (KS) indicating the stretch at which collagen fibers start to engage, and the elastic moduli (EM) identifying tangential stiffness at the fully engaged state. The respective stresses are plotted versus displacements of the hooks in the equi-displacement protocol (FIG. 14F), versus the central stretches based on markers' tracking from (FIG. 14G) all the protocols and versus the (FIG. 14H) interpolated equi-stretch protocol.

FIG. 15A shows Thickness of unwounded tissue from medial and lateral skin. FIG. 15B Wound closure observations at different locations of both right and left limbs shown as a percentage closure from day 1. FIG. 15C Percent of wound closure occurring through re-epithelialization. FIG. 15D Granulation tissue (GT) present at day 14 upon removal of Tegaderm film in two horses. FIG. 15E GT scores of proximal wounds compared with distal wounds. *=p<0.05, ****=p<0.0001. n=8.

FIGS. 16A-16I show a lack of preferential directions in biomechanical data and intrinsic difference between unwounded skin and healing wounds in an example of the present disclosure. FIG. 16A shows Knee stretch (KS) ratios of each direction (11 and 22) for wounded and unwounded specimens. FIG. 16B shows representative SHG images of collagen within the dermis in unwounded (Day 0) and wounded (Day 28) tissue. FIG. 16C shows alignment of collagen fibers in the dermis, as observed on SHG images. FIG. 16D shows Knee stretch (KS) at day 0 and 42, medial compared with lateral. FIG. 16E KS and FIG. 16F energy loss (EL) in different limb locations expressed as a percent of that horses own unwounded control from the same site. FIG. 16G Elastic modulus (EM), FIG. 16H KS, and FIG. 16I EL comparison of healing wounds with restored epithelial barrier ("closed") or not ("open"). *=p<0.05, =p<0.01, *=p<0.001, ****=p<0.0001. n=8.

FIG. 17A shows representative gross wound images from horse #4 across 42 days. FIG. 17B shows a survival curve indicating the time at which wounds were observed to be fully healed across treatment groups. FIG. 17C percent of total wound closure measured as a function of wounds on day 1 control. FIG. 17D Granulation score (higher number indicates worse appearance) of distal wounds at days 14, 28, and 42. FIG. 17E Percentage of wound closure occurring through re-epithelialization and contraction. Results reported as mean+/−SD. n=8. E=No treatment, H=Peptide-free hydrogel, QH=Q-peptide hydrogel, RQH=Q-peptide hydrogel (repeated application). n=8.

FIG. 18A shows representative 20× images from day 14 biopsies stained for granulocytes & macrophages (MAC387-red) as well as von Willebrand factor (vWF-green) to highlight endothelial cells within blood vessels. FIG. 18B shows quantification of total MAC387+ immune cells per high powered field (hpf). FIG. 18C shows quantification of VwF+ blood vessels intersecting with a computerized grid overlaid per hpf. E=No treatment, H=Peptide-free hydrogel, QH=Q-peptide hydrogel, RQH=Q-peptide hydrogel (repeated application). Scale bars, 50 µM. Data represented as mean+/−SD. n=8.

FIG. 19A shows representative 20× images from day 28 biopsies stained with Hematoxylin & Eosin (H&E) FIG. 19B Epidermal and FIG. 19C dermal thickness measurements were averaged across 3 separate locations within the healed wound edge (between dashed lines) and FIG. 19D granulation tissue thickness was measured in the area of open wound (*). E=No treatment, H=Peptide-free hydrogel, QH=Q-peptide hydrogel, RQH=Q-peptide hydrogel (repeated application). Data presented as mean+/−SD. n=8.

FIG. 2(a) Elastic modulus (EM), (b) knee stretch (KS) and (c) energy loss (EL) for wounds with different treatments shown as a percent change of its own Day 0. *=p<0.05, =p<0.01, *=p<0.001, ****=p<0.0001. n=8. E=No treatment, H=Peptide-free hydrogel, QH=Q-peptide hydrogel, RQH=Q-peptide hydrogel (repeated application).

FIG. 21A—Age distribution of respondents in North America. FIG. 21B—Skin type of respondents in North America. Respondents were allowed to select more than one option. FIG. 21C—Age distribution of respondents in China. FIG. 21D—Skin type of respondents in China.

FIG. 22A—Q1: I felt that Kerra made my skin look less irritated. FIG. 22B—Q2: I felt that Kerra made my skin feel more hydrated. FIG. 22C—Q3: I felt that Kerra made my skin look healthier. FIG. 22D—Q4: I felt that Kerra made my skin feel smoother. FIG. 22E—Q5: I felt that Kerra improved the overall appearance of my skin.

FIGS. 23A-23F shows a series of graphs depicting that Chinese participants reported favourable responses when using Kerra on dry and oily skin in an example of the present disclosure. FIG. 23A—How does Kerra compare to your current product? FIG. 23B—How was your experience with Kerra? FIG. 23C—Likert scale responses from users with oily skin when asked "Rate your experience when applying Kerra to skin." FIG. 23D—Likert scale responses from users with oily skin when asked "Rate your experience after using Kerra for 7 days." FIG. 23E—Likert scale responses from users with dry skin when asked "Rate your experience when applying Kerra to skin." FIG. 23F—Likert scale responses from users with dry skin when asked "Rate your experience after using Kerra for 7 days" N=14.

FIG. 24A—Baseline acne symptoms (pain and redness) before treatment with Kerra. FIG. 24B—Participant evaluated effects on acne after 5 days of Kerra application. FIG. 24C—Overall reported effect of Kerra on acne prone skin suggests Kerra has a positive benefit. N=8 participants.

DETAILED DESCRIPTION OF THE INVENTION

Figure 1:
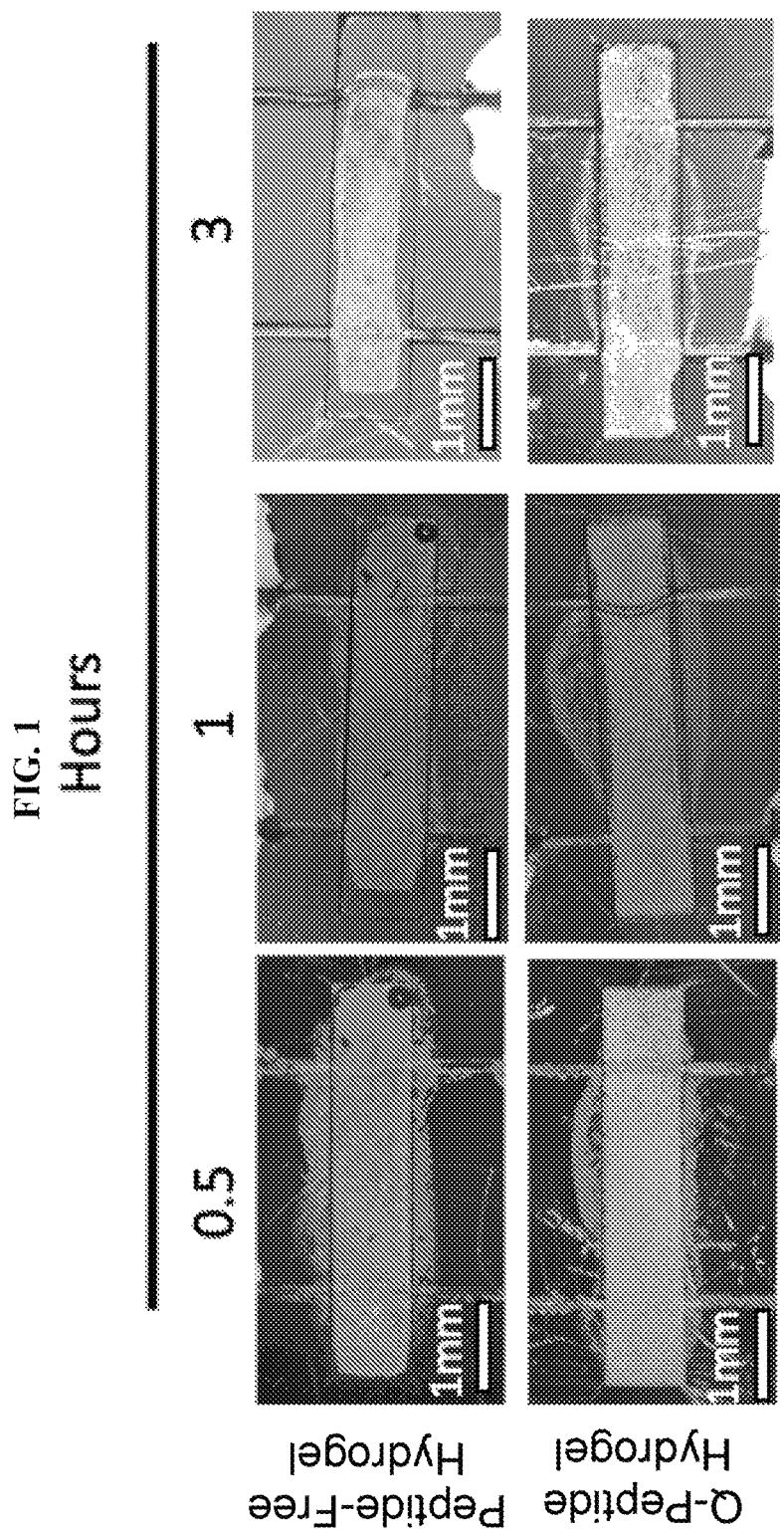
FIG. 1 is a series of representative brightfield images of tissues showing that a peptide comprising an amino acid sequence of QHREDGS (SEQ ID NO: 1), referred to herein as Q-peptide, slows gel compaction and increases the number of intact tissues over 7 days of culture, in accordance with an example of the present disclosure. Representative brightfield images of the tissues were taken over the initial three hours of compaction.

The present disclosure provides compositions and methods for their use. In one embodiment, the composition provides a use in healing of dermis wound in a subject in need thereof. In one embodiment, the composition provides a use in improving the condition and appearance of skin.

I. Definitions

Unless otherwise defined, all technical and scientific terms used herein have the same meaning as commonly understood by one of ordinary skill in the art to which this disclosure belongs. The terminology used in the description is for describing particular embodiments only and is not intended to be limiting of the disclosure.

Where a range of values is provided, it is understood that each intervening value, to the tenth of the unit of the lower limit unless the context clearly dictates otherwise, between the upper and lower limit of that range and any other stated or intervening value in that stated range is encompassed within the disclosure. The upper and lower limits of these smaller ranges may independently be included in the smaller ranges is also encompassed within the disclosure, subject to any specifically excluded limit in the stated range. Where the stated range includes one or both of the limits, ranges excluding either both of those included limits are also included in the disclosure.

The following terms are used to describe the present disclosure. In instances where a term is not specifically defined herein, that term is given an art-recognized meaning by those of ordinary skill applying that term in context to its use in describing the present disclosure.

The articles "a" and "an" as used herein and in the appended claims are used herein to refer to one or to more than one (i.e., to at least one) of the grammatical object of the article unless the context clearly indicates otherwise. By way of example, "an element" means one element or more than one element.

The phrase "and/or," as used herein in the specification and in the claims, should be understood to mean "either or both" of the elements so conjoined, i.e., elements that are conjunctively present in some cases and disjunctively present in other cases. Multiple elements listed with "and/or" should be construed in the same fashion, i.e., "one or more" of the elements so conjoined. Other elements may optionally be present other than the elements specifically identified by the "and/or" clause, whether related or unrelated to those elements specifically identified. Thus, as a non-limiting example, a reference to "A and/or B", when used in conjunction with open-ended language such as "comprising" can refer, in one embodiment, to A only (optionally including elements other than B); in another embodiment, to B only (optionally including elements other than A); in yet another embodiment, to both A and B (optionally including other elements); etc.

As used herein in the specification and in the claims, "or" should be understood to have the same meaning as "and/or" as defined above. For example, when separating items in a list, "or" or "and/or" shall be interpreted as being inclusive, i.e., the inclusion of at least one, but also including more than one, of a number or list of elements, and, optionally, additional unlisted items. Only terms clearly indicated to the contrary, such as "only one of" or "exactly one of," or, when used in the claims, "consisting of," will refer to the inclusion of exactly one element of a number or list of elements. In general, the term "or" as used herein shall only be interpreted as indicating exclusive alternatives (i.e., "one or the other but not both") when preceded by terms of exclusivity, such as "either," "one of," "only one of," or "exactly one of."

In the claims, as well as in the specification above, all transitional phrases such as "comprising," "including," "carrying," "having," "containing," "involving," "holding," "composed of," and the like are to be understood to be open-ended, i.e., to mean including but not limited to. Only the transitional phrases "consisting of" and "consisting essentially of" shall be closed or semi-closed transitional phrases, respectively, as set forth in the United States Patent Office Manual of Patent Examining Procedures, Section 2111.03.

As used herein in the specification and in the claims, the phrase "at least one," in reference to a list of one or more elements, should be understood to mean at least one element selected from anyone or more of the elements in the list of elements, but not necessarily including at least one of each and every element specifically listed within the list of elements and not excluding any combinations of elements in the list of elements. This definition also allows that elements may optionally be present other than the elements specifically identified within the list of elements to which the phrase "at least one" refers, whether related or unrelated to those elements specifically identified. Thus, as a non-limiting example, "at least one of A and B" (or, equivalently, "at least one of A or B," or, equivalently "at least one of A and/or B") can refer, in one embodiment, to at least one, optionally including more than one, A, with no B present (and optionally including elements other than B); in another embodiment, to at least one, optionally including more than one, B, with no A present (and optionally including elements other than A); in yet another embodiment, to at least one, optionally including more than one, A, and at least one, optionally including more than one, B (and optionally including other elements); etc.

It should also be understood that, in certain methods described herein that include more than one step or act, the order of the steps or acts of the method is not necessarily limited to the order in which the steps or acts of the method are recited unless the context indicates otherwise.

The terms "co-administration" and "co-administering" or "combination therapy" refer to both concurrent administration (administration of two or more therapeutic agents at the same time) and time varied administration (administration of one or more therapeutic agents at a time different from that of the administration of an additional therapeutic agent or agents), as long as the therapeutic agents are present in the patient to some extent, preferably at effective amounts, at the same time.

The term "compound", as used herein, unless otherwise indicated, refers to any specific chemical compound disclosed herein and includes tautomers, regioisomers, geometric isomers, and where applicable, stereoisomers, including optical isomers (enantiomers) and other stereoisomers (diastereomers) thereof, as well as pharmaceutically acceptable salts and derivatives, including prodrug and/or deuterated forms thereof where applicable, in context. Deuterated small molecules contemplated are those in which one or more of the hydrogen atoms contained in the drug molecule have been replaced by deuterium.

Within its use in context, the term compound generally refers to a single compound, but also may include other compounds such as stereoisomers, regioisomers and/or optical isomers (including racemic mixtures) as well as specific enantiomers or enantiomerically enriched mixtures of disclosed compounds. The term also refers, in context to prodrug forms of compounds which have been modified to facilitate the administration and delivery of compounds to a site of activity. It is noted that in describing the present compounds, numerous substituents and variables associated with same, among others, are described. It is understood by those of ordinary skill that molecules which are described herein are stable compounds as generally described hereunder. When the bond is shown, both a double bond and single bond are represented or understood within the context of the compound shown and well-known rules for valence interactions.

The term "patient" or "subject" is used to describe an animal, preferably a human or a domesticated animal, to whom treatment, including prophylactic treatment, with the compositions according to the present disclosure is provided. For treatment of those conditions or disease states which are specific for a specific animal such as a human patient, the term patient refers to that specific animal, including a domesticated animal such as a dog or cat, a mammal such as mice, rats, and non-human primates, or a farm animal such as a horse, cow, sheep, etc. In general, in the present disclosure, the term patient refers to a human patient unless otherwise stated or implied from the context of the use of the term.

The terms "treat," treatment," and "treating" refer to (1) a reduction in severity or duration of a condition, (2) the amelioration of one or more symptoms associated with a condition without necessarily curing the condition, or (3) the prevention of a condition.

The terms "healing," as in "wound healing" refers to (1) a reduction in size, severity or duration of a wound, (2) the amelioration of one or more symptoms associated with a wound without necessarily curing the wound, or (3) a lessening in the growth or severity of a wound.

The term "effective" is used to describe an amount of a compound, composition or component which, when used within the context of its intended use, effects an intended result. The term effective subsumes all other effective amount or effective concentration terms, which are otherwise described or used in the present application.

The term "dermis wound" is used to describe a wound that affects the dermis of the skin and not just the epidermis.

The term "aged dermis" is used to describe a dermis in an aged individual characterized by changes such as decrease of collagen III and increase in elastic modulus.

The term "damaged dermis" is used to describe a dermis that has been affected to change its appearance, mechanical properties and composition by external factors such as (but not limited to) sun exposure, accidents, surgical or dermatological procedures, acne and acute illness.

The term "diseased dermis" is used to describe a dermis that exhibits pathophysiological and phenotypic changes in cellular composition, extracellular matrix composition and mechanical properties in comparison to the healthy dermis in the same subject.

The term "deep incisional wound" is used to describe a wound that results from an incision that extends through the skin layers as well as the deep tissue consisting of underlying fascia and muscle.

The term "superficial incisional wound" is used to describe a wound that only spans through the skin and subcutaneous layer.

The term "ablative non-fractional laser wound" is used to describe a wound resulting from removal of the outer surface of the skin in the entire area of the skin treated by the laser.

The term "ablative fractional laser wound" is used to describe a wound resulting from removal of the outer surface of the skin in small fractions of the area of the skin treated by the laser.

The term "microneedling wound" is used to describe a skin wound created by the microneedling procedure with or without radiofrequency.

The terms "substantially", "approximately," and "about" generally mean plus or minus 10% of the value stated, e.g., about 100 would include 90 to 110.

II. Compositions of the Disclosure

The present disclosure provides a peptide comprising, consisting essentially of or consisting of an amino acid sequence of $X_1X_2X_3X_4X_5X_6X_7$, wherein $X_1$ is an optional residue selected from glutamine, threonine, serine or asparagine;

$X_2$ is an optional positively charged residue selected from histidine, arginine or lysine;

$X_3$ is glutamate, threonine, isoleucine, histidine, lysine, glutamine, tyrosine, valine or leucine;

$X_4$ is glycine or valine;

$X_5$ is an optional residue selected from serine, threonine, aspartic acid, isoleucine or glycine;

$X_6$ is an optional residue selected from leucine, valine, glutamine, glycine, isoleucine or serine;

and X7 is an optional residue selected from aspartic acid, asparagine, valine or lysine.

In some embodiments, the peptide comprises an amino acid sequence of SEQ ID NO: 22, wherein $X_1$ is Q, wherein $X_2$ is H, wherein $X_3$ is R, wherein $X_4$ is E, wherein $X_5$ is D, wherein $X_6$ is G and wherein $X_7$ is S.

In some embodiments, the peptide comprises, consists essentially of or consists of an amino acid sequence of QHREDGS (SEQ ID NO: 1). In some embodiments, the peptide comprises, consists essentially of or consists of an amino acid sequence of REDG (SEQ ID NO: 3). In some embodiments, the peptide comprises, consists essentially of or consists of an amino acid sequence of RLDG (SEQ ID NO: 4). In some embodiments, the peptide comprises, consists essentially of or consists of an amino acid sequence of REDGS (SEQ ID NO: 5). In some embodiments, the peptide comprises, consists essentially of or consists of an amino acid sequence of RLDGS (SEQ ID NO: 6). In some embodiments, the peptide comprises, consists essentially of or consists of an amino acid sequence of HREDG (SEQ ID NO: 7). In some embodiments, the peptide comprises, consists essentially of or consists of an amino acid sequence of HRLDG (SEQ ID NO: 8). In some embodiments, the peptide comprises, consists essentially of or consists of an amino acid sequence of HREDGS (SEQ ID NO: 9). In some embodiments, the peptide comprises, consists essentially of or consists of an amino acid sequence of HRLDGS (SEQ ID NO: 10). In some embodiments, the peptide comprises, consists essentially of or consists of an amino acid sequence of QHREDG (SEQ ID NO: 11). In some embodiments, the peptide comprises, consists essentially of or consists of an amino acid sequence of QHRLDG (SEQ ID NO: 12). In some embodiments, the peptide comprises, consists essentially of or consists of an amino acid sequence of QHREDVS (SEQ ID NO: 13). In some embodiments, the peptide comprises, consists essentially of or consists of an amino acid sequence of QHREDGS (SEQ ID NO: 14). In some embodiments, the peptide comprises, consists essentially of or consists of an amino acid sequence of QHRLDGS (SEQ ID NO: 15). In some embodiments, the peptide comprises, consists essentially of or consists of an amino acid sequence of KRLDGS (SEQ ID NO: 16). In some embodiments, the peptide comprises, consists essentially of or consists of an amino acid sequence of QHREDGSL (SEQ ID NO: 17). In some embodiments, the peptide comprises, consists essentially of or consists of an amino acid sequence of QHRLDGSL (SEQ ID NO: 18). In some embodiments, the peptide comprises, consists essentially of or consists of an amino acid sequence of QHRLDGSLD (SEQ ID NO: 19). In some embodiments, the peptide comprises, consists essentially of or consists of an amino acid sequence of QHREDGSLD (SEQ ID NO: 20). In some embodiments, the peptide consists of an amino acid sequence of QHREDGS (SEQ ID NO: 1).

In some embodiments, the composition or peptide of the invention comprise, consist essentially of or consists of a non-naturally occurring peptide as described in U.S. Pat. No. 9,096,643 and U.S. Publication Nos. US20180296631A1 and US20190328824A1, each of which are incorporated herein by reference in their entirety.

In some embodiments, the peptide may be linear, cyclic, cross-linked or immobilized as long as the cell-protective activity of the peptide is retained. In addition, the peptide may form a broad U-shape to assume the native structural characteristics of this peptide as it exists in angiopoietin 1.

In still other embodiments, the peptide may include modifications which do not substantially affect the U-shape of the core residues so as to retain the cell-protective activity of the peptide, e.g. integrin-binding activity. For example, the peptide may be modified to include one or more additional amino acid residues at either the C- or N-termini, or to include a terminal protecting group that may function to stabilize the peptide, protect the peptide from undesirable degradation or improve the activity thereof. Any chemical group which serves to protect peptide ends may be used. Useful N-terminal protecting groups include, for example, lower alkanoyl groups of the formula R—C(O)— wherein R is a linear or branched lower alkyl chain comprising from 1-5 carbon atoms. Examples of N-terminal protecting groups include the acetyl group and amino acid analogues lacking the amino function. Examples of suitable carboxyl terminal protecting groups include, for example, ester-forming alkyl groups, particularly lower alkyl groups such as methyl, ethyl and propyl, as well as amide-forming amino functions such as primary amine (—NH2), as well as monoalkylamino and dialkylamino groups such as methylamino, ethylamino, dimethylamino, diethylamino, methylethylamino and the like. C-terminal protection can also be achieved using a decarboxylated amino acid analogue, such as agmatine. Of course, N- and C-protecting groups of even greater structural complexity may alternatively be incorporated, if desired.

In yet other embodiments, the peptide may also be modified at one or more of its core amino acid residues, for example, to include a derivatized R-group. Suitable modifications include those which may stabilize the U-shape of the peptide, to optimize the activity thereof, or which function to protect the peptide from degradation.

III. Formulations

The present disclosure provides formulations, dosages and methods for administration of the compositions described herein (e.g. QHREDGS (SEQ ID NO: 1)).

In some embodiments, the QHREDGS (SEQ ID NO: 1) peptide is soluble.

The disclosed compositions and pharmaceutical compositions and formulations can further comprise at least one of any suitable auxiliary, such as, but not limited to, diluent, binder, stabilizer, buffers, salts, lipophilic solvents, preservative, adjuvant or the like. Pharmaceutically acceptable auxiliaries are preferred. Non-limiting examples of, and methods of preparing such sterile solutions are well known in the art, such as, but limited to, Gennaro, Ed., Remington's Pharmaceutical Sciences, 18th Edition, Mack Publishing Co. (Easton, Pa.) 1990 and in the "Physician's Desk Reference", 52nd ed., Medical Economics (Montvale, N.J.) 1998. Pharmaceutically acceptable carriers can be routinely selected that are suitable for the mode of administration, solubility and/or stability of the protein scaffold, fragment or variant composition as well known in the art or as described herein.

A. Topical Formulations

The compositions of the invention (e.g. QHREDGS (SEQ ID NO: 1)) may be provided in physiologically acceptable vehicles or carriers. The vehicle may be either hydrophobic or hydrophilic. Suitable, hydrophobic carriers include, for example, waxy non-ionic substances commonly used in cosmetics, such as esters and ethers of fatty alcohols and of fatty acids, with carbon chain length from C8 to C22, preferably from C8 to C15, or from C12 to C15.

Exemplary fatty hydrophobic carriers include, but are not limited to, isopropyl myristate, isopropyl palmitate, octyl palmitate, isopropyl lanolate, acetylated lanolin alcohol, the benzoate of C12-C15 alcohols, cetearyl octanoate, cetyl palmitate, myristyl myristate, myristyl lactate, cetyl acetate, propylene glycol dicaprylate/caprate, decyl oleate, acetylated lanolin, stearyl heptanoate, diisostearyl malate, octyl hydroxystearate, octyl hydroxystearate, isopropyl isostearate, shea butter or rosehip oil.

Exemplary suitable hydrophilic carriers may comprise, but are not limited to, water, lower alcohols (C1-6), glycols and alkoxylated glycols commonly used in cosmetics, including ethylene glycol, diethylene glycol, triethylene glycol, propylene glycol, dipropylene glycol, and the like.

The topically acceptable vehicle may be in the form of an emulsion. Non-limiting examples of suitable emulsions include water-in-oil emulsions, oil-in-water emulsions, silicone-in-water emulsions, water-in-silicone emulsions, wax-in-water emulsions, water-oil-water triple emulsions or the like having the appearance of a cream, gel or microemulsions. As used herein, the term "oil" includes silicone oils, and naturally derived oils such as rosehip oil, unless otherwise indicated. The emulsion may include an emulsifier, such as a nonionic, anionic or amphoteric surfactant, glyceryl stearate, Polysorbate 60, Cetearyl Olivate, Sorbitan Olivate, Sodium Stearyl Lactylate, Stearic Acid, PEG 100 Stearate or a gellant, typically in an amount from about 0.001% to about 5% by weight.

The topically acceptable vehicle may include but are not limited to water; vegetable oils; mineral oils; ester oils such as octal palmitate, isopropyl myristate and isopropyl palmitate; ethers such as dicapryl ether and dimethyl isosorbide; alcohols such as ethanol and isopropanol; fatty alcohols such as cetyl alcohol, cetearyl alcohol, stearyl alcohol and behenyl alcohol; isoparaffins such as isooctane, isododecane (IDD) and isohexadecane; silicone oils such as cyclomethicone, dimethicone, dimethicone cross-polymer, polysiloxanes and their derivatives, preferably organomodified derivatives including PDMS, dimethicone copolyol, dimethiconols, and amodimethiconols; hydrocarbon oils such as mineral oil, petrolatum, isoeicosane and polyolefins, e.g., (hydrogenated) polyisobutene; polyols such as propylene glycol, glycerin, butylene glycol, pentylene glycol, hexylene glycol, caprylyl glycol; waxes such as beeswax, carnauba, ozokerite, microcrystalline wax, polyethylene wax, and botanical waxes; or any combinations or mixtures of the foregoing. Aqueous vehicles may include one or more solvents miscible with water, including lower alcohols, such as ethanol, isopropanol, and the like. The vehicle may comprise from about 50% to about 99% by weight of the formulation.

In some embodiments, the peptides of the invention are formulated for delivery using targeted delivery systems. Exemplary targeted delivery systems include but are not limited to liposomes, microspheres (see, e.g., U.S. Pat. No. 5,770,222 to Unger et al), so that the components and/or active constituents can more readily reach and affect the subcutaneous layer of the area of application, e.g., face or neck, or the other area of the skin.

The peptides of the invention may also be formulated in a formulation for topical administration. Examples of a topical formulation include, but are not limited to, a lotion, cream, serum, spray, aerosol, cake, ointment, essence, gel, paste, patch, pencil, towelette, mask, stick, foam, elixir, concentrate, and the like, particularly for topical administration. Preferably, the composition is formulated as a gel, a tincture, a cream, an ointment, a lotion, or an aerosol spray.

The topical formulation comprises a peptide of the invention from about 0.000001% by weight to about 20% by weight of the formulation. In some embodiments, the topical formulation comprises a peptide from about 0.00001% by weight to about 10% by weight of the formulation. In some embodiments, the topical formulation comprises a peptide from about 0.00001% by weight to about 5% by weight of the formulation. In some embodiments, the topical formulation comprises a peptide from about 0.00001% by weight to about 0.0001% by weight of the formulation. In some embodiments, the topical formulation comprises a peptide from about 0.00001% by weight to about 0.001% by weight of the formulation. In some embodiments, the topical formulation comprises a peptide from about 0.001% by weight or to about 1% by weight of the formulation.

In some embodiments, the topical formulation has a pH range from about 1 to about 13. In some embodiments, the topical formulation has a pH range of from about 2 to about 12. In some embodiments, the topical formulation has a pH range of from about 3.5 to about 7. In some embodiments, the topical formulation has a pH range of from about 7 to about 10.5. In some embodiments, the topical formulation has a pH range from about 3 to about 4, about 4 to about 5, about 5 to about 6, about 6 to about 7, about 7 to about 8, about 8 to about 9, about 9 to about 10, about 10 to about 11 or about 11 to about 12. Suitable pH adjusters, such as, but not limited to, sodium hydroxide, citric acid and triethanolamine may be added to bring the pH within the desired range.

The pharmaceutical composition or topical formulation of the disclosure may further include one or more additional skin actives, including but not limited to, anti-aging components, retinoids, botanicals, keratolytic agents, desquamating agents, keratinocyte proliferation enhancers, collagenase inhibitors, elastase inhibitors, depigmenting agents, anti-inflammatory agents, steroids, anti-acne agents, antioxidants, anti-scarring agents and advanced glycation end-product (AGE) inhibitors. The amounts of these various ingredients are those conventionally used in the cosmetic field to achieve their intended purpose, and range individually or collectively typically from about 0.001% to about 20% by weight of the formulation. The nature of these ingredients and their amounts must be compatible with the production and function of the compositions of the disclosure.

Exemplary anti-aging components include, but are not limited to botanicals (e.g., *Butea frondosa* extract, *Tiliacora triandra* extract, *Portulaca oleracea, Melicope elleryana*, etc.); phytol; phytonic acid; retinoids; hydroxy acids (including alpha-hydroxy acids and beta-hydroxy acids), salicylic acid and alkyl salicylates; exfoliating agents (e.g., glycolic acid, 3,6,9-trioxaundecanedioic acid, etc.), estrogen synthetase stimulating compounds (e.g., caffeine and derivatives); compounds capable of inhibiting 5 alpha-reductase activity (e.g., linolenic acid, linoleic acid, finasteride, and mixtures thereof); and barrier function enhancing agents (e.g., ceramides, glycerides, cholesterol and its esters, alpha-hydroxy and omega-hydroxy fatty acids and esters thereof, etc.).

Exemplary retinoids include, but are not limited to, retinoic acid (e.g., all-trans, or 9-cis, or 13-cis), and derivatives thereof, retinaldehyde, retinol (Vitamin A) and esters thereof, such as retinyl palmitate, retinyl acetate and retinyl propionate, and salts thereof. Particular mention may be made of retinol. When present, the retinoids will typically be included in amounts from about 0.0001% to about 5% by weight, more typically from about 0.01% to about 2.5% by weight, or from about 0.1% to about 1.0% by weight. Formulations comprising retinoids may also include an antioxidant such as ascorbic acid and/or BHT and/or a chelating agent such as EDTA or a salt thereof (e.g., disodium EDTA) in amounts effective to stabilize the retinoid (e.g., 0.0001%-5%).

The pharmaceutical composition or topical formulation of the disclosure may further include one or more of a skin penetration enhancer; an emollient, such as isopropyl myristate, petrolatum, volatile or non-volatile silicones oils (e.g., methicone, dimethicone), ester oils, mineral oils, rosehip oil, shea butter, jojoba oil, castor oil, macadamia oil, argan oil, kukui nut oil, petrolatum, mineral oil, evening primrose oil and fatty acid esters; a humectant, such as glycerin, hexylene glycol or caprylyl glycol; a skin plumper, such as palmitoyl oligopeptide, collagen, collagen and/or glycosaminoglycan (GAG) enhancing agents; a sunscreen, such as avobenzone or octyl methoxycinnamate; an exfoliating agent; or an antioxidant.

Exemplary exfoliating agents include, but are not limited to, alpha-hydroxy acids, beta-hydroxy acids, oxa-acids, oxadiacids, and their derivatives such as esters, anhydrides or salts thereof. Exemplary hydroxy acids include, but are not limited to, glycolic acid, lactic acid, malic acid, tartaric acid, citric acid, 2-hydroxy alkanoic acid, mandelic acid, salicylic acid or derivatives thereof. An exfoliating agent may comprise from about 0.001% to about 20% by weight of the formulation.

Exemplary antioxidants include, but are not limited to, compounds having phenolic hydroxy functions, such as ascorbic acid and its derivatives/esters; beta-carotene; catechins; curcumin; ferulic acid derivatives (e.g., ethyl ferulate, sodium ferulate); gallic acid derivatives (e.g., propyl gallate); lycopene; reductic acid; rosmarinic acid; tannic acid; tetrahydrocurcumin; tocopherol and its derivatives, including tocopheryl acetate; uric acid; or any mixtures thereof. Other suitable antioxidants are those that have one or more thiol functions (—SH), in either reduced or non-reduced form, such as glutathione, lipoic acid, thioglycolic acid, and other sulfhydryl compounds. The antioxidant may be inorganic, such as bisulfites, metabisulfites, sulfites, or other inorganic salts and acids containing sulfur. Antioxidants may comprise, individually or collectively, from about 0.001% to about 10% by weight of the formulation. Antioxidants may comprise, individually or collectively, from about 0.01% to about 5% (w/w) of the total weight of the formulation.

The pharmaceutical composition or topical formulation of the disclosure may further include one or more other components, including, but are not limited to: vitamins, such as tocopherol and ascorbic acid; vitamin derivatives such as ascorbyl monopalmitate, tocopheryl acetate, and Vitamin E palmitate; thickeners such as hydroxyalkyl cellulose, carboxymethylcellulose, carbombers, cetyl alcohol, cetearyl alcohol and vegetable gums such as xanthan gum; gelling agents, such as ester-terminated polyester amides, hydroxyethyl cellulose, hydroxypropyl cellulose, methylcellulose, hydroxypropyl methylcellulose, sodium hyaluronate, hyaluronic acid, sodium carbome or aloe gel; structuring agents; metal chelating agents such as EDTA or salts thereof; pigments; colorants; and pH adjusters. Representative pH adjusting buffers include organic acid salts, such as salts of citric acid, ascorbic acid, gluconic acid, carbonic acid, tartaric acid, succinic acid, acetic acid, or phthalic acid; Tris, tromethamine hydrochloride, or phosphate buffers.

The pharmaceutical composition or topical formulation of the disclosure may further include one or more other components, known to those skilled in the art including, but not limited to, film formers, moisturizers, minerals, viscosity and/or rheology modifiers, anti-acne agents, insect repellents, skin cooling compounds, skin protectants, lubricants, fragrances, preservatives, stabilizers, and mixtures thereof. The components may individually or collectively comprise from about 0.0001% to about 20% by weight of the formulation.

The pharmaceutical composition or topical formulation of the disclosure may further include one or more compatible cosmetically acceptable adjuvants commonly used and known in the art, including, but not limited to: colorants, pearls, chromalites, micas, pigments, dyes, fragrances, emollients, humectants (such as propanediol 1,3 glycerin), preservatives (such as Benzyl Alcohol, Ethylhexylglycerin, Benzoic Acid, Sorbic Acid, Gluconolactone, Sodium Benzoate or Calcium Gluconate), vitamins, chelators, thickeners, anesthetics, anti-allergenic s, antifungals, antimicrobials, other anti-inflammatory agents, antioxidants, antiseptics, depigmenting agents, film formers, insect repellents, pharmaceutical agents, photostabilizing agents, sunscreens, stabilizers, surfactants, thickeners, viscosity modifiers, and botanicals.

The pharmaceutical composition or topical formulation of the disclosure may further include cosmetic ingredients including, but not limited to, a skin penetration enhancer, a surface smoother, a skin plumper, an optical diffuser, an exfoliation promoter, and an antioxidant. Details with respect to these and other suitable cosmetic ingredients can be found in the "International Cosmetic Ingredient Dictionary and Handbook," 10th Edition (2004), published by the Cosmetic, Toiletry, and Fragrance Association (CTFA), at pp. 2177-2299, which is herein incorporated by reference in its entirety. The amounts of cosmetic ingredients and those used in the cosmetic or pharmaceutical fields, may can comprise from about 0.01% to about 20% of the total weight of the formulation.

The pharmaceutical composition or topical formulation of the disclosure may further include a sunscreen to protect the skin from damaging ultraviolet rays. In some embodiments, the sunscreen provides both UVA and UVB protection, by using either a single sunscreen or a combination of sunscreens. Exemplary sun screens include, but are not limited to avobenzone, cinnamic acid derivatives (such as octylmethoxy cinnamate), octyl salicylate, oxybenzone, octocrylene, titanium dioxide, zinc oxide, or any mixtures thereof. The sunscreen may comprise from about 1 wt % to about 30 wt % of the total weight of the formulation.

B. Formulations Comprising Carriers

A formulation of the invention may comprise a peptide of the invention and at least one carrier. In some embodiments, the peptide may be conjugated to the carrier. In certain embodiments, the carrier is a hydrogel. In some embodiments, the hydrogel comprises at least one of chitosan, alginate, agarose, methylcellulose, hyaluronan, collagen, laminin, matrigel, fibronectin, vitronectin, poly-1-lysine, proteoglycans, fibrin glue, gels made by decellularization of engineered and natural tissues, and a combination thereof. In some embodiments, the hydrogel comprises chitosan.

The formulation may comprise a peptide of the invention from about 0.000001% by weight to about 20% by weight of the formulation. In some embodiments, the formulation comprises a peptide from about 0.00001% by weight to about 10% by weight of the formulation. In some embodiments, the formulation comprises a peptide from about 0.00001% by weight to about 5% by weight of the formulation. In some embodiments, the formulation comprises a peptide from about 0.00001% by weight to about 0.0001% by weight of the formulation. In some embodiments, the formulation comprises a peptide from about 0.00001% by weight to about 0.001% by weight of the formulation. In some embodiments, the formulation comprises a peptide from about 0.001% by weight or to about 1% by weight of the formulation.

In some embodiments, the formulation comprises a carrier at about 10%, about 15%, about 20%, about 25%, about 30%, about 35%, about 40%, about 45%, about 50%, about 55%, about 60%, about 65%, about 70% or about 75% by weight of the formulation. In some embodiments, the formulation comprises a carrier at about 10% to about 40% by weight of the formulation. In some embodiments, the formulation comprises a carrier at about 20% to about 50% by weight of the formulation. In some embodiments, the formulation comprises a carrier at about 30% to about 60% by weight of the formulation. In some embodiments, the formulation comprises a carrier at about 40% to about 70% by weight of the formulation. In some embodiments, the formulation comprises a carrier at about 20% to about 50% by weight of the formulation.

The amount of peptide or combination of peptides as described herein e.g., QHREDGS (SEQ ID NO: 1) peptide, in the carrier is not particularly limited and can be adjusted based by one of ordinary skill in the art based on the severity of the wound and other factors generally considered by the skilled artisan. In certain embodiments of the invention, the concentration of peptide or combination of peptides present in the carrier is from about 10 μM to about 1000 μM. In still other embodiments, the peptide or combination of peptides are present in the carrier is from about 50 μM to about 800 μM; about 75 μM to about 750 μM; about 100 μM to about 600 μM; or about 150 μM to about 500 μM.

In some embodiments, the formulation further comprises a collagen. In some embodiments, the formulation comprises collagen at about 0.01%, about 0.02%, about 0.03%, about 0.04%, about 0.05%, about 0.06%, about 0.07%, about 0.08%, about 0.09%, about 1.0%, about 1.1%, about 1.2%, about 1.3%, about 1.4%, about 1.5%, about 1.6%, about 1.7%, about 1.8%, about 1.9%, about 2.0%, about 2.1%, about 2.2%, about 2.3%, about 2.4%, about 2.5%, about 2.6%, about 2.7%, about 2.8%, about 2.9% or about 3.0% by weight of the formulation. In some embodiments, the formulation comprises collagen at about 0.02% to about 2% by weight of the formulation.

In one embodiment, the invention provides, a formulation comprising a peptide as described herein dispersed in or immobilized on a carrier.

Suitable carriers for this purpose will generally be at least one of: i) biocompatible (i.e., any material synthetic or naturally occurring that is non-toxic to the subject), ii) biodegradable, and iii) mechanically stable enough to withstand the environment into which they are administered. Suitable carriers may be pre-formed films, or three-dimensional porous or fibrous scaffolds. The carriers may also be injectable, so that they can be applied with a syringe in a minimally invasive manner. Examples of suitable carriers include, but are not limited to, natural carriers such as polysaccharides, e.g. chitosan, alginate, agarose, methylcellulose, hyaluronan, collagen (e.g. collagen I, collagen II and collagen IV), laminin, matrigel, fibronectin, vitronectin, poly-1-lysine, proteoglycans, fibrin glue, gels made by decellularization of engineered and natural tissues as well as embryoid bodies. Also included as suitable carriers are synthetic carriers such as polyglycolic acid (PGA), polylactic acid (PLA) and combinations of PGA and PLA such as PLGA, poly.epsilon.-caprolactone, polyvinyl alcohol (PVA), polyethylene glycol (PEG), methyl methacrylate, poly(methyl methacrylate) (PMMA), poly(2-hydroxyethyl methacrylate) (PolyHEMA), poly(glycerol sebacate), self-assembling peptide hydrogels such as AcN-RARADADA-RARADADA-CNH (SEQ ID NO.: 2), polyurethanes, poly (isopropylacrylamide), and poly(N-isopropylacrylamide) [poly(NIPAM)]. Combinations of any of these materials may also be used as well as chemically modified forms thereof such as carboxylated or aminated forms.

In a particular embodiment, the composition comprises a QHREDGS (SEQ ID NO: 1) peptide and at least one hydrogel composed of at least one carrier and a solvent. As examples of suitable carriers, non-limiting mention is made of glycerol, propylene glycol, polyethylene glycol, chitosan, alginate, agarose, polyethers, polyesters, methylcellulose, hyaluronan, collagen, laminin, matrigel, fibronectin, vitronectin, poly-1-lysine, proteoglycans, fibrin glue, gels made by decellularization of engineered and natural tissues, or a combination thereof. In certain embodiments, the hydrogel comprises or is polyglycolic acid (PGA), polylactic acid (PLA) and combinations of PGA and PLA such as PLGA, poly ε-caprolactone, polyvinyl alcohol (PVA), polyethylene glycol (PEG), methyl methacrylate, poly(methyl methacrylate) (PMMA), poly(2-hydroxyethyl methacrylate) (PolyHEMA), poly(glycerol sebacate), self-assembling peptide hydrogels, AcN-RARADADARARADADA-CNH (SEQ ID NO.: 2), polyurethanes, poly(isopropylacrylamide), poly(N-isopropylacrylamide) [poly(NIPAM)], derivatives of the same or combinations thereof.

In certain embodiments, the carrier is a hydrogel. In additional embodiments, a suitable solvent is water. Other carriers and solvents may be used.

In still additional embodiments, the composition is comprised or dispersed within a second carrier, for example, a polymer or co-polymer material, such as polyvinyl, polyacrylic, polyurethane, polyethylene or the like. In certain embodiments, the second carrier is woven or a non-woven layer or multi-layer article that comprises or includes the peptide-hydrogel as described herein.

In some embodiments, the compositions include at least one water-based hydrogel. As non-limiting examples of such hydrogels, mention is made of hydrogels prepared from polyacrylic acids, povidones, celluloses, and aloe. In some embodiments, a carboxy-methyl-cellulose hydrogel is used. Other hydrogels may also be used in accordance with the present disclosure.

In particular embodiments, the carrier is chosen from polymers, such as water-soluble polymers, polymers of neutral charge, or water-soluble polymers of neutral charge. The carrier may also be considered by the FDA to be generally regarded as safe (GRAS). As examples of carriers which may be used in accordance with the present disclosure, non-limiting mention is made of hydrogels, including cellulose containing hydrogels such as carboxy-methyl-cellulose (CMC). In some embodiments of the present disclosure, the at least one carrier also includes at least one of water, glycerol, and mixtures thereof.

The average molecular weight of the hydrogel or the carrier may range, for example, from about 100 Daltons (Da) to about 1,000,000 Da, such as from about 500,000 Da to about 1,000,000 Da.

The viscosity of the carrier may also be chosen to suit a desired application. For example, the viscosity of the carrier may range from greater than 0 to about 10,000 centipoise (cps) or more, such as from about 100 to about 10,000 cps, from about 500 to about 5,000 cps, or even from about 1000 to about 3000 cps. In some embodiments, the carrier is a high viscosity CMC that exhibits a viscosity ranging from about 1,500 to about 3,000 cps, as measured from a 1% solution of CMC in water at 25° C. In many instances, the viscosity of the carrier is both concentration and temperature dependent. That is, the viscosity may decrease as temperature increases, and vice versa. Similarly, the viscosity may decrease as concentration decreases, and vice versa.

In some embodiments, the compositions of the present disclosure also include at least one stabilizer. Such stabilizers may serve a variety of purposes. For example, stabilizers may be added to the compositions of the present disclosure for the purpose of buffering the pH and/or the viscosity of the carrier (e.g., a hydrogel) in the presence of various metal salts. The stabilizer may be natural or synthetic, and is optionally biodegradable and/or bioerodable. Non-limiting examples of pH stabilizers that are suitable for use in accordance with the present disclosure include buffering salts and organic chemical compounds such as triethanolamine, often abbreviated as TEA, which is both a tertiary amine and a tri-alcohol. Citric acid is also suitable for use in the present disclosure as a pH stabilizer.

The peptide of the present disclosure can be immobilized in or conjugated to the hydrogel by any means known in the art including, but not limited to, solvent casting. In particular embodiments, the hydrogel and the peptide are conjugated to using 1-ethyl-3-(3-dimethylaminopropyl) carbodiimide (EDC) chemistry. In such embodiments, the hydrogel and the peptide are dissolved in a solvent, such as saline, optionally containing a phosphate buffer. The dissolved materials are mixed with EDC and N-hydroxysulfosuccinimide (S—NHS) and reacted. After conjugation, the materials can be worked up using standard procedures and used to prepare a film or other composition for administration.

C. Pharmaceutical Formulations and Scaffolds

In certain embodiments, the invention provides a pharmaceutical formulation comprising at least one composition of the invention as described herein.

In some embodiments, the pharmaceutical formulations further comprise at least one excipient, such as a water-soluble polymer, a surfactant, and/or another enhancer such as a pharmaceutically acceptable excipient. Non-limiting examples of pharmaceutically acceptable excipients are described in Remington's Pharmaceutical Sciences by E. W. Martin, and include cellulose, starch, glucose, lactose, sucrose, gelatin, malt, rice, flour, chalk, silica gel, sodium stearate, glycerol monostearate, talc, sodium chloride, dried skim milk, glycerol, propylene, glycol, water, ethanol, and the like. In some embodiments, the pharmaceutical formulations also contain pH buffering reagents, and wetting or emulsifying agents.

The pharmaceutical formulations of the invention can be in the any form suitable for administration to a patient, such as in the form of an aqueous dispersion or suspension. The pharmaceutical formulations may also contain various additional ingredients, such as suspending, stabilizing and/or dispersing agents.

In some embodiments, the pharmaceutical formulations are in the form of a controlled-release formulation.

The compositions of the present disclosure may also include at least one excipient. The at least one excipient may be chosen, for example, from surfactants (cationic, anionic, or neutral), surface stabilizers, and other enhancers, such as preservatives. Non-limiting examples of surfactants that may be used in accordance with the present disclosure include nonionic surfactants such as a polysorbate surfactant (e.g., polysorbate 20 (Tween 20TH), and polysorbate 80 (Tween 80TH)). In some embodiments, the compositions of the present disclosure contain multiple pH stabilizers so as to form a pH buffering system within the composition. As an example of a preservative that may be added to the compositions of the present disclosure, non-limiting mention is made of glycerol, which may act as a preservative at certain concentrations.

The compositions of the present disclosure may also include at least one emulsifier. Non-limiting examples of suitable emulsifiers include, phospholipids, propylene glycol, polysorbate, poloxamer, and glyceryl monostearate. Of course, other known pharmaceutical emulsifiers may be used.

Commonly used pharmaceutical ingredients that can be used as appropriate to formulate the composition for its intended route of administration include: acidifying agents (examples include but are not limited to acetic acid, citric acid, fumaric acid, hydrochloric acid, nitric acid); alkalinizing agents (examples include but are not limited to ammonia solution, ammonium carbonate, diethanolamine, monoethanolamine, potassium hydroxide, sodium borate, sodium carbonate, sodium hydroxide, triethanolamine, trolamine); adsorbents (examples include but are not limited to powdered cellulose and activated charcoal); aerosol propellants (examples include but are not limited to carbon dioxide, $CC_2F_2$, $F_2ClC—CClF_2$ and $CClF_3$); air displacement agents (examples include but are not limited to nitrogen and argon); antifungal preservatives (examples include but are not limited to benzoic acid, butylparaben, ethylparaben, methylparaben, propylparaben, sodium benzoate); antimicrobials (examples include but are not limited to silver, bismuth, chlorhexidine, polyhexamethylene biguanide (PHMB), hypochlorous acid/sodium hypochlorite, crystal violet, ozone, and antibiotics (e.g., bacitracin)); antimicrobial preservatives (examples include but are not limited to benzalkonium chloride, benzethonium chloride, benzyl alcohol, cetylpyridinium chloride, chlorobutanol, phenol, phenylethyl alcohol, phenylmercuric nitrate and thimerosal); antioxidants (examples include but are not limited to ascorbic acid, ascorbyl palmitate, butylated hydroxyanisole, butylated hydroxytoluene, hypophosphorus acid, monothioglycerol, propyl gallate, sodium ascorbate, sodium bisulfite, sodium formaldehyde sulfoxylate, sodium metabisulfite); binding materials (examples include but are not limited to block polymers, natural and synthetic rubber, polyacrylates, polyurethanes, silicones, polysiloxanes and styrene-butadiene copolymers); buffering agents (examples include but are not limited to potassium metaphosphate, dipotassium phosphate, sodium acetate, sodium citrate anhydrous and sodium citrate dihydrate); carrying agents (examples include but are not limited to acacia syrup, aromatic syrup, aromatic elixir, cherry syrup, cocoa syrup, orange syrup, syrup, corn oil, mineral oil, peanut oil, sesame oil, bacteriostatic sodium chloride injection and bacteriostatic water for injection); chelating agents (examples include but are not limited to edetate disodium and edetic acid); colorants (examples include but are not limited to FD&C Red No. 3, FD&C Red No. 20, FD&C Yellow No. 6, FD&C Blue No. 2, D&C Green No. 5, D&C Orange No. 5, D&C Red No. 8, caramel and ferric oxide red); clarifying agents (examples include but are not limited to bentonite); emulsifying agents (examples include but are not limited to acacia, cetomacrogol, cetyl alcohol, glyceryl monostearate, lecithin, sorbitan monooleate, polyoxyethylene 50 monostearate); encapsulating agents (examples include but are not limited to gelatin and cellulose acetate phthalate); flavorants (examples include but are not limited to anise oil, cinnamon oil, cocoa, menthol, orange oil, peppermint oil and vanillin); humectants (examples include but are not limited to glycerol, propylene glycol and sorbitol); levigating agents (examples include but are not limited to mineral oil and glycerin); oils (examples include but are not limited to arachis oil, mineral oil, olive oil, peanut oil, sesame oil and vegetable oil); ointment bases (examples include but are not limited to lanolin, hydrophilic ointment, polyethylene glycol ointment, petrolatum, hydrophilic petrolatum, white ointment, yellow ointment, and rose water ointment); penetration enhancers (transdermal delivery) (examples include but are not limited to monohydroxy or polyhydroxy alcohols, mono- or polyvalent alcohols, saturated or unsaturated fatty alcohols, saturated or unsaturated fatty esters, saturated or unsaturated dicarboxylic acids, essential oils, phosphatidyl derivatives, cephalin, terpenes, amides, ethers, ketones and ureas); plasticizers (examples include but are not limited to diethyl phthalate and glycerol); solvents (examples include but are not limited to ethanol, corn oil, cottonseed oil, glycerol, isopropanol, mineral oil, oleic acid, peanut oil, purified water, water for injection, sterile water for injection and sterile water for irrigation); stiffening agents (examples include but are not limited to cetyl alcohol, cetyl esters wax, microcrystalline wax, paraffin, stearyl alcohol, white wax and yellow wax); suppository bases (examples include but are not limited to cocoa butter and polyethylene glycols (mixtures)); surfactants (examples include but are not limited to benzalkonium chloride, nonoxynol 10, oxtoxynol 9, polysorbate 80, sodium lauryl sulfate and sorbitan monopalmitate); suspending agents (examples include but are not limited to agar, bentonite, carbomers, carboxymethylcellulose sodium, hydroxyethyl cellulose, hydroxypropyl cellulose, hydroxypropyl methylcellulose, kaolin, methylcellulose, tragacanth and veegum); sweetening agents (examples include but are not limited to aspartame, dextrose, glycerol, mannitol, propylene glycol, saccharin sodium, sorbitol and sucrose); thickening agents (examples include but are not limited to beeswax, cetyl alcohol and paraffin); tonicity agents (examples include but are not limited to dextrose and sodium chloride); viscosity increasing agents (examples include but are not limited to alginic acid, bentonite, carbomers, carboxymethylcellulose sodium, methylcellulose, polyvinyl pyrrolidone, sodium alginate and tragacanth); and wetting agents (examples include but are not limited to heptadecaethylene oxycetanol, lecithins, sorbitol monooleate, polyoxyethylene sorbitol monooleate, and polyoxyethylene stearate).

In particular embodiments, the pharmaceutical formulation of the invention are adhered to a backing or dressing for application as a patch or bandage. In such embodiments, the pharmaceutical patch according to the invention comprises a backing layer and a pharmaceutical layer. The construction and use of transdermal patches for the delivery of pharmaceutical agents is well known in the art (see, e.g., U.S. Pat. No. 5,023,252, issued Jun. 11, 1991, incorporated herein by reference). Such patches may be constructed for continuous, pulsatile, or on demand delivery of pharmaceutical agents.

The term "pharmaceutical layer" as used herein refers to any layer comprising a composition of the invention or any layer comprising a peptide and a hydrogel as defined herein.

The term "backing layer" as used herein refers to any layer that represents the surface layer after the application of the pharmaceutical patch. This definition includes permanent backing layer commonly used for pharmaceutical patches as well as thin non-removable films that are typically used in thin flexible patches.

In some embodiments, the backing layer comprises one or more polymers selected from the group consisting of polyurethanes, polyester elastomers, polyether block amides, polyacrylates, ethylene vinyl acetates, ethylene acrylate copolymers, ionomer resins, polyvinyl chloride, polyvinylidene chloride, polyesters and polyolefins, such as polyethylene; polyolefins, in particular polyethylene, polyesters, ethylene vinylacetate copolymers and polyurethanes are particularly preferred. Other materials which can be used to form the backing include, but are not limited to, modified cellulosics such as cotton, rayon, ramie and the like; modified polyolefins such as low density polyethylene and polypropylene, modified polyesters and modified poly(acrylonitriles). Examples of particular materials of these types include oxidized cellulosics; phophorylated cellulosics; carboxymethylated cellulosics; succinylated cellulosics; grafts of polyolefins such as polypropylene with polyacrylics such as polyacrylic acid, hydrolyzed poly(acrylamides), polyacrylates, and poly(acrylonitriles); grafts of cellulosics with polyacrylics such as polyacrylic acid, hydrolyzed poly(acrylamides), polyacrylates and poly(acrylonitriles); sulfonated polyolefins; partially hydrolyzed poly(acrylonitriles) and partially hydrolyzed polyesters.

The backing layer may be a non-woven fabric or a laminate. In certain embodiments, the backing layer comprises a polymer film, such as a polyester film, and a heat seal layer. In some embodiments, the backing layer may be rendered self adhesive by application of a thin layer of glue such as an acrylic adhesive.

The thickness of the backing layer is not particularly limited. Preferably, the backing layer has a thickness within the range of from 0.1 to 5000 µm; from 0.5 to 1000 µm; from 1 to 750 µm; from 5 to 500 µm; or from 10 to 250

The pharmaceutical patch according to the invention optionally comprises a removable protective layer (release liner).

In certain embodiments, the removable protective layer comprises a polymer film and a silicone coating or fluoropolymer coating. In particular embodiments, the polymer film is a polyolefin, in particular polyethylene or polypropylene film or polyester, in particular polyethylene terephthalate film.

At least one stabilizer and/or at least one excipient (described previously) may be added to the carrier before or after combining the carrier with the particles. For example, a pH stabilizer such as triethanolamine may be added to the carrier to stabilize the pH of the final product and/or the dispersion/suspension, if a specific pH is desired. After the components are mixed, the final product is allowed to cool to room temperature. The viscosity of the final product may be controlled, for example, by controlling the amount of stabilizer and/or other components.

In an additional aspect, the description provides a tissue scaffold comprising a composition including at least one peptide as described herein and a carrier, wherein the peptide is immobilized to the carrier. In certain embodiments, the at least one peptide has the amino acid sequence QHREDGS (SEQ ID NO: 1). In certain embodiments, the carrier is a hydrogel. In additional embodiments, the hydrogel is a polyacrylic acid hydrogel, a povidone hydrogel or a cellulose hydrogel; chitosan, alginate, agarose, methylcellulose, hyaluronan, collagen, laminin, matrigel, fibronectin, vitronectin, poly-1-lysine, prozation of engineered and natural tissues, and proteoglycans, fibrin glue, gels made by decellularization of engineered and natural tissues, and a combination thereof; polyglycolic acid (PGA), polylactic acid (PLA) and combinations of PGA and PLA such as PLGA, poly ε-caprolactone, polyvinyl alcohol (PVA), polyethylene glycol (PEG), methyl methacrylate, poly(methyl methacrylate) (PMMA), poly(2-hydroxyethyl methacrylate) (PolyHEMA), poly(glycerol sebacate), self-assembling peptide hydrogels, AcN-RARADADARARADADA-CNH (SEQ ID NO: 2), polyurethanes, poly(isopropylacrylamide), poly (N-isopropylacrylamide) [poly(NIPAM)] or a combination thereof.

In any of the aspects or embodiments described herein, the composition further comprises at least one peptide having the amino acid sequence REDG (SEQ ID NO: 3), RLDG (SEQ ID NO: 4), REDGS (SEQ ID NO: 5), RLDGS (SEQ ID NO: 6), HREDG (SEQ ID NO: 7), HRLDG (SEQ ID NO: 8), HREDGS (SEQ ID NO: 9), HRLDGS (SEQ ID NO: 10), QHREDG (SEQ ID NO: 11), QHRLDG (SEQ ID NO: 12), QHREDVS (SEQ ID NO: 13), QHREDGS (SEQ ID NO: 14), QHRLDGS (SEQ ID NO: 15), KRLDGS (SEQ ID NO: 16), QHREDGSL (SEQ ID NO: 17), QHRLDGSL (SEQ ID NO: 18), QHRLDGSLD (SEQ ID NO: 19), QHREDGSLD (SEQ ID NO: 20) or a combination thereof.

In certain embodiments, the peptide is conjugated to the hydrogel within the tissue scaffold.

In any of the aspects or embodiments described herein, the tissue scaffold is in the form of a sheet, a graft, a bead, a wafer, a chip, a disc, a tube, a cylinder or a cone.

In any of the aspects or embodiments, the tissue scaffold further comprising an acidifying agent, an alkalinizing agent, an adsorbent, an aerosol propellant, an air displacement agent, an antifungal preservative, an antimicrobial agent, an antimicrobial preservative, an antioxidant, a binding material, a buffering agent, a carrying agent, a chelating agent, a colorant, a clarifying agent, an emulsifying agent, an encapsulating agent, a flavor ant, a humectant, a levigating agent, an oil, an ointment base, a penetration enhancer, a plasticizer, a stiffening agent, a surfactant, a suspending agent, a thickening agent, a tonicity agent, a viscosity increasing agent, a wetting agent, or a combination thereof.

In any of the aspects or embodiments, the tissue scaffold further comprises an additional active agent. In any of the aspects or embodiments, the tissue scaffold includes an QHREDGS peptide in an amount effective to induce at least one of cell growth, cell differentiation, tissue repair or a combination thereof.

In any of the aspects or embodiments described herein, the tissue scaffold is configured for use in vitro or for use in in vivo tissue growth, grafting, repair or combinations thereof.

In some embodiments, the tissue scaffold of the invention further comprises at least one stabilizer.

In still other embodiments the tissue scaffold of the invention is in the form of a sheet, a graft, a bead, a wafer, a chip, a disc, a tube, a cylinder or a cone.

In certain embodiments, the tissue scaffold of the invention, further comprises an acidifying agent, an alkalinizing agent, an adsorbent, an aerosol propellant, an air displacement agent, an antifungal preservative, an antimicrobial agent, an antimicrobial preservative, an antioxidant, a binding material, a buffering agent, a carrying agent, a chelating agent, a colorant, a clarifying agent, an emulsifying agent, an encapsulating agent, a flavor ant, a humectant, a levigating agent, an oil, an ointment base, a penetration enhancer, a plasticizer, a stiffening agent, a surfactant, a suspending agent, a thickening agent, a tonicity agent, a viscosity increasing agent, a wetting agent, or a combination thereof. In still other embodiments, the tissue scaffold of the invention further comprises an additional active agent.

IV. Combination Therapies

In any of the aspects or embodiments described herein, the described compositions and formulations can be used alone or in combination with another therapeutic agent to treat such conditions. It should be understood that the compositions and formulations of the invention can be used alone or in combination with an additional active agent, e.g., a therapeutic agent, said additional agent being selected by the skilled artisan for its intended purpose. For example, the additional agent can be a therapeutic agent art-recognized as being useful to treat the disease or condition being treated by the compositions and formulations of the present invention. The additional agent also can be an agent that imparts a beneficial attribute to the therapeutic composition e.g., an agent that affects the viscosity of the composition.

It should further be understood that the combinations which are to be included within this invention are those combinations useful for their intended purpose. The agents set forth below are illustrative for purposes and not intended to be limited. The combinations, which are part of this invention, can be the compounds of the present invention and at least one additional agent selected from the lists below. The combination can also include more than one additional agent, e.g., two or three additional agents if the combination is such that the formed composition can perform its intended function.

Preferred combinations include antimicrobial agents. Such agents include, but are not limited to, silver, bismuth, chlorhexidine, polyhexamethylene biguanide (PHMB), hypochlorous acid/sodium hypochlorite, crystal violet, ozone, and antibiotics (e.g., bacitracin)).

Preferred combinations are non-steroidal anti-inflammatory drug(s) also referred to as NSAIDS which include drugs like ibuprofen. Other preferred combinations are corticosteroids including prednisolone; the well-known side-effects of steroid use can be reduced or even eliminated by tapering the steroid dose required when treating patients in combination with the S IP receptor agonists or antagonists of this invention. Non-limiting examples of therapeutic agents for rheumatoid arthritis with which a composition of the invention can be combined include the following: cytokine suppressive anti-inflammatory drug(s) (CSAIDs); antibodies to or antagonists of other human cytokines or growth factors, for example, TNF, LT, IL-I, IL-2, IL-3, IL-4, IL-5, IL-6, IL-7, IL-8, IL-12, IL-15, IL-16, IL-21, IL-23, interferons, EMAP-II, GM-CSF, FGF, and PDGF. S/T kinase inhibitors of the invention can be combined with antibodies to cell surface molecules such as CD2, CD3, CD4, CD8, CD25, CD28, CD30, CD40, CD45, CD69, CD80 (B7.1), CD86 (B7.2), CD90, CTLA or their ligands including CD154 (gp39 or CD40L).

Preferred combinations of therapeutic agents may interfere at different points in the autoimmune and subsequent inflammatory cascade; preferred examples include TNF antagonists like chimeric, humanized or human TNF antibodies, D2E7 (HUMIRA™), (PCT Publication No. WO 97/29131), CA2 (REMICADE™), CDP571, and soluble p55 or p75 TNF receptors, derivatives, thereof, (p75TNFR1gG (ENBREL™) or p55TNFR1gG (Lenercept), and also TNFα converting enzyme (TACE) inhibitors; similarly IL-1 inhibitors (Interleukin-1-converting enzyme inhibitors, IL-1RA etc.) may be effective for the same reason. Other preferred combinations include Interleukin 11. Yet other preferred combinations are the other key players of the autoimmune response which may act parallel to, dependent on or in concert with IL-18 function; especially preferred are IL-12 antagonists including IL-12 antibodies or soluble IL-12 receptors, or IL-12 binding proteins. It has been shown that IL-12 and IL-18 have overlapping but distinct functions and a combination of antagonists to both may be most effective. Yet another preferred combination are non-depleting anti-CD4 inhibitors. Yet other preferred combinations include antagonists of the co-stimulatory pathway CD80 (B7.1) or CD86 (B7.2) including antibodies, soluble receptors or antagonistic ligands.

Compositions and formulations of the invention may also be combined with agents, such as methotrexate, 6-MP, azathioprine sulphasalazine, mesalazine, olsalazine chloroquinine/hydroxychloroquine, pencillamine, aurothiomalate (intramuscular and oral), azathioprine, cochicine, corticosteroids (oral, inhaled and local injection), beta-2 adrenoreceptor agonists (salbutamol, terbutaline, salmeteral), xanthines (theophylline, aminophylline), cromoglycate, nedocromil, ketotifen, ipratropium and oxitropium, cyclosporin, FK506, rapamycin, mycophenolate mofetil, leflunomide, NSAIDs, for example, ibuprofen, corticosteroids such as prednisolone, phosphodiesterase inhibitors, adensosine agonists, antithrombotic agents, complement inhibitors, adrenergic agents, agents which interfere with signalling by proinflammatory cytokines such as TNFα or IL-1 (e.g. IRAK, NIK, IKK, p38 or MAP kinase inhibitors), IL-1I3 converting enzyme inhibitors, T-cell signalling inhibitors such as kinase inhibitors, metalloproteinase inhibitors, sulfasalazine, 6-mercaptopurines, angiotensin converting enzyme inhibitors, soluble cytokine receptors and derivatives thereof (e.g. soluble p55 or p75 TNF receptors and the derivatives p75TNFRIgG (Enbrel™ and p55TNFRIgG (Lenercept)), sIL-1RI, sIL-1RII, sIL-6R), antiinflammatory cytokines (e.g. IL-4, IL-10, IL-11, IL-13 and TGF (3), celecoxib, folic acid, hydroxychloroquine sulfate, rofecoxib, etanercept, infliximab, naproxen, valdecoxib, sulfasalazine, methylprednisolone, meloxicam, methylprednisolone acetate, gold sodium thiomalate, aspirin, triamcinolone acetonide, propoxyphene napsylate/apap, folate, nabumetone, diclofenac, piroxicam, etodolac, diclofenac sodium, oxaprozin, oxycodone HCl, hydrocodone bitartrate/apap, diclofenac sodium/misoprostol, fentanyl, anakinra, tramadol HCl, salsalate, sulindac, cyanocobalamin/fa/pyridoxine, acetaminophen, alendronate sodium, prednisolone, morphine sulfate, lidocaine hydrochloride, indomethacin, glucosamine sulf/chondroitin, amitriptyline HCl, sulfadiazine, oxycodone HCl/acetaminophen, olopatadine HCl misoprostol, naproxen sodium, omeprazole, cyclophosphamide, rituximab, IL-1 TRAP, MRA, CTLA4-IG, IL-18 BP, anti-IL-12, Anti-IL15, BIRB-796, SCIO-469, VX-702, AMG-548, VX-740, Roflumilast, IC-485, CDC-801, and Mesopram. Preferred combinations include methotrexate or leflunomide and in moderate or severe rheumatoid arthritis cases, cyclosporine and anti-TNF antibodies as noted above.

Compositions and formulations of the invention may also be combined with agents, such as alemtuzumab, dronabinol, daclizumab, mitoxantrone, xaliproden hydrochloride, fampridine, glatiramer acetate, natalizumab, sinnabidol, a-immunokine NNSO3, ABR-215062, AnergiX.MS, chemokine receptor antagonists, BBR-2778, calagualine, CPI-1189, LEM (liposome encapsulated mitoxantrone), THC.CBD (cannabinoid agonist), MBP-8298, mesopram (PDE4 inhibitor), MNA-715, anti-IL-6 receptor antibody, neurovax, pirfenidone allotrap 1258 (RDP-1258), sTNF-R1, talampanel, teriflunomide, TGF-beta2, tiplimotide, VLA-4 antagonists (for example, TR-14035, VLA4 Ultrahaler, Antegran-ELAN/Biogen), interferon gamma antagonists and IL-4 agonists.

Non-limiting examples of therapeutic agents for psoriasis with which a compound of formulation of the invention can be combined include the following: calcipotriene, clobetasol propionate, triamcinolone acetonide, halobetasol propionate, tazarotene, methotrexate, fluocinonide, betamethasone diprop augmented, fluocinolone acetonide, acitretin, tar shampoo, betamethasone valerate, mometasone furoate, ketoconazole, pramoxine/fluocinolone, hydrocortisone valerate, flurandrenolide, urea, betamethasone, clobetasol propionate/emoll, fluticasone propionate, azithromycin, hydrocortisone, moisturizing formula, folic acid, desonide, pimecrolimus, coal tar, diflorasone diacetate, etanercept folate, lactic acid, methoxsalen, hc/bismuth subgal/znox/resor, methylprednisolone acetate, prednisone, sunscreen, halcinonide, salicylic acid, anthralin, clocortolone pivalate, coal extract, coal tar/salicylic acid, coal tar/salicylic acid/sulfur, desoximetasone, diazepam, emollient, fluocinonide/emollient, mineral oil/castor oil/na lact, mineral oil/peanut oil, petroleum/isopropyl myristate, psoralen, salicylic acid, soap/tribromsalan, thimerosal/boric acid, celecoxib, infliximab, cyclosporine, alefacept, efalizumab, tacrolimus, pimecrolimus, PUVA, UVB, and sulfasalazine.

Non-limiting examples of therapeutic agents for psoriatic arthritis with which a compound of formulation of the invention can be combined include the following: methotrexate, etanercept, rofecoxib, celecoxib, folic acid, sulfasalazine, naproxen, leflunomide, methylprednisolone acetate, indomethacin, hydroxychloroquine sulfate, prednisone, sulindac, betamethasone diprop augmented, infliximab, methotrexate, folate, triamcinolone acetonide, diclofenac, dimethylsulfoxide, piroxicam, diclofenac sodium, ketoprofen, meloxicam, methylprednisolone, nabumetone, tolmetin sodium, calcipotriene, cyclosporine, diclofenac sodium/misoprostol, fluocinonide, glucosamine sulfate, gold sodium thiomalate, hydrocodone bitartrate/apap, ibuprofen, risedronate sodium, sulfadiazine, thioguanine, valdecoxib, alefacept and efalizumab.

Non-limiting examples of therapeutic agents for restenosis with which a compound of formulation of the invention can be combined include the following: sirolimus, paclitaxel, everolimus, tacrolimus, ABT-578, and acetaminophen.

Preferred examples of therapeutic agents for SLE (Lupus) with which a compound of formulation of the invention can be combined include the following: NSAIDS, for example, diclofenac, naproxen, ibuprofen, piroxicam, indomethacin; COX2 inhibitors, for example, celecoxib, rofecoxib, valdecoxib; anti-malarials, for example, hydroxychloroquine; steroids, for example, prednisone, prednisolone, budenoside, dexamethasone; cytotoxics, for example, azathioprine, cyclophosphamide, mycophenolate mofetil, methotrexate; inhibitors of PDE4 or purine synthesis inhibitor, for example Cellcept®. A compound of formula (I), (Ia), (Ib), or (Ic) may also be combined with agents such as sulfasalazine, 5-aminosalicylic acid, olsalazine, Imuran® and agents which interfere with synthesis, production or action of proinflammatory cytokines such as IL-1, for example, caspase inhibitors like IL-1I3 converting enzyme inhibitors and IL-1ra. A compound of formula (I), (Ia), (Ib), or (Ic) may also be used with T cell signaling inhibitors, for example, tyrosine kinase inhibitors; or molecules that target T cell activation molecules, for example, CTLA-4-IgG or anti-B7 family antibodies, anti-PD-1 family antibodies. A compound of formula (I), (Ia), (Ib), or (Ic) can be combined with IL-11 or anti-cytokine antibodies, for example, fonotolizumab (anti-IFNg antibody), or anti-receptor receptor antibodies, for example, anti-IL-6 receptor antibody and antibodies to B-cell surface molecules. A compound of formula (I), (Ia), (Ib), or (Ic) may also be used with LJP394 (abetimus), agents that deplete or inactivate B-cells, for example, Rituximab (anti-CD20 antibody), lymphostat-B (anti-BlyS antibody), TNF antagonists, for example, anti-TNF antibodies, D2E7 (PCT Publication No. WO 97/29131; HUMIRA™), CA2 (REMICADE™), CDP571, TNFR-Ig constructs, (p75TNFRIgG (ENBREL™) and p55TNFRIgG (Lenercept™)).

One or more compound of formulation of the invention can be administered to a human patient by themselves or in pharmaceutical compositions where they are mixed with pharmaceutically acceptable carriers or excipient(s) at doses to treat or ameliorate a disease or condition as described herein. Mixtures of these compounds can also be administered to the patient as a simple mixture or in suitable formulated pharmaceutical compositions. A therapeutically effective dose refers to that amount of the compound or compounds sufficient to result in the prevention or attenuation of a disease or condition as described herein. Techniques for formulation and administration of the compounds of the instant application may be found in references well known to one of ordinary skill in the art, such as "Remington's Pharmaceutical Sciences," Mack Publishing Co., Easton, PA, latest edition.

V. Methods of Use

A. Method of Treating a Dermis Wound

Mammalian skin is comprised of three layers: the epidermis that comprises the surface of the skin, the dermis, and the deep hypodermis (also called subcutaneous adipose layer). The human epidermis is very thin and is a stratified epithelium made of epithelial cells and keratinocytes organized in layers. The deepest (basal) layer lies on a basement membrane at the dermal-epidermal junction. The dermis layer consists of dermal fibroblasts and extracellular matrix. Blood vessels, nerves and hair follicles reside in the dermis.

The nature of the wound dictates the repair mechanism. "Partial-thickness" wounds involve the epidermis and may involve a portion of the dermis. These wounds can be further classified in "superficial" or "shallow" and "deep" partial-thickness wounds, depending on the amount of dermis lost. Typically, epithelial-derived adnexal structures such as hair follicles, sebaceous glands, apocrine glands and/or eccrine sweat glands remain partially intact in a partial-thickness wound. They heal primarily by re-epithelialization. New epidermis forms from outgrowths of eccrine sweat glands and pilosebaceous units underlying the wound. Keratinocyte migration from the wound edge is minimal. Wounds heal with minimal scarring and skin structure is minimally altered in the repaired site. By contrast, "Full-thickness" wounds destroy the dermis and possibly the subcutaneous muscle and fat layers underneath. These wounds may possibly affect fibroblasts, blood vessels, nerves, hair follicles. They do not heal by re-epithelialization alone but require formation of a granulation tissue to fill the void of the wound before epithelial covering. After healing, the wound site bares a scar. Skin structure remains greatly modified with disappearance of appendages and altered vasculature. All surgical wounds cut through the entire dermis.

In human wound healing, the re-epithelialization process requires abundant new cells to replace the keratinocytes that have been lost by injury. In partial thickness wound healing, the epidermis mostly originates from the pilosebaceous units and eccrine sweat glands underlying the wound, with also little contribution of the wound margin. Full-thickness wounds differ from partial-thickness wounds in that they lack a base for keratinocyte repopulation. Therefore, a full-thickness wound requires a prior "fibrous" healing or healing that occurs in the dermis, fat, or fascia, prior to reepithelialization. When the wound is deep enough so that no dermis or dermal cells remains in the wound bed, granulation tissue must be produced entirely by fibroblasts. Fibroblasts are drawn from several sources, primarily the healthy dermis at the wound margins, from which fibroblasts can divide and migrate, circulating fibrocytes and bone marrow progenitor cells. Fibroblasts can also be recruited from multipotent cells that are resident in the dermis and have the potential to differentiate into other dermal fibroblasts such as myofibroblasts. Fibroblasts and myofibroblasts help to draw the wound closed, and contribute to the synthesis, bundling and alignment of collagen fibres, the primary constituent of scar tissue.

QHREDGS (SEQ ID NO: 1) is an angiopoietin-1 derived peptide, which interacts with integrins, receptors that function in cell-adhesion and ECM-binding to promote and enhance wound healing. The peptide enhances endothelial cell metabolism, tube formation kinetics, and survival in response to apoptotic stimuli. The peptide was also shown to promote neonatal rat cardiomyocyte attachment and survival, to inhibit human induced pluripotent stem cell (hiPSC) apoptosis during cells expansion, to induce osteoblast matrix deposition and mineralization, and to have cardiac protective effects in a chitosan-collagen hydrogel both in vitro and in vivo.

The QHREDGS (SEQ ID NO: 1) peptide can promote keratinocyte survival and migration and thereby accelerate diabetic wound healing. The QHREDGS (SEQ ID NO: 1) peptide is useful as a soluble supplement or immobilized in a substrate on the survival of normal human keratinocytes upon oxidative stress by protecting keratinocytes against hydrogen peroxide stress in a dose dependent manner. Collective migration of both normal and diabetic human keratinocytes can be promoted with the QHREDGS (SEQ ID NO: 1) peptide. Accelerated wound closure is also promoted with the QHREDGS (SEQ ID NO: 1) peptide, primarily due to faster re-epithelialization and increased granulation tissue formation.

The present disclosure provides the use of a disclosed composition, a pharmaceutical composition or a formulation comprising a peptide of the disclosure for the treatment of a wound in a tissue, organ, animal, or subject, as known in the art or as described herein, using the disclosed compositions and pharmaceutical compositions, e.g., administering or contacting the tissue, organ, animal, or subject with a therapeutic effective amount of the composition or pharmaceutical composition. In one aspect, the subject is a mammal. Preferably, the subject is human. The terms "subject" and "patient" are used interchangeably herein.

The disclosure provides a method for modulating or treating at least one wound in a tissue, organ, animal or subject. In some aspects, the wound is a dermis wound, an aged dermis, a diseased dermis, a damaged dermis, a surgical wound, a cosmetic wound, an accidental wound, a non-penetrating wound, a burn wound, a self-inflicted wound or a combination thereof. In some embodiments, the wound is a dermis wound. Surgical wounds include but are not limited to deep incisional wounds or superficial incisional wounds. Non-penetrating wounds include but are not limited to skin abrasions or bruises. Burn wounds include but are not limited to sunburns, radiation burns, open blisters or peeling wounds. Cosmetic wounds include but are not limited to fractional ablative laser wounds, non-fractional ablative laser wounds, ablative laser wounds, non-ablative laser wounds or micro-needling wounds.

In some embodiments, the wound is external to the body cavity of the patient, including but not limited to, an external surface wound or wound to the epithelium lining the gastrointestinal system or airways.

In some embodiments, the wound is at least one of a sore, a cold sore, a cutaneous opening, a lesion, an abrasions, a burn, a rash, an ulcer, a pressure ulcer, an arterial ulcer, a venous ulcer, a diabetes-related wound, a burn, a sun burn, an aging skin wound, a corneal ulceration wound, an inflammatory gastrointestinal tract disease wound, a bowel inflammatory disease wound, a Crohn's disease wound, an ulcerative colitis, a hemorrhoid, an epidermolysis bulosa wound, a skin blistering wound, a psoriasis wound, an animal skin wound, a proud flesh wound, an animal diabetic wound, a retinopathy wound, an oral wound (mucositis), a vaginal mucositis wound, a gum disease wound, a laceration, a surgical incision wound, a post-surgical adhesions wound, a grafted skin site, or a donor skin site.

In still other embodiments, the invention relates to the treatment of a skin condition associated with, caused by, or affected by diabetes; including, but not limited to atherosclerotic skin changes, bacterial and fungal infections of the skin, itching, NLD, Granuloma annulare, diabetic dermopathy, sclerederma, diabeticorum, APD, and cutaneous infections.

B. Method of Improving a Condition or Aesthetic Appearance of Skin

The skin is made up of multiple layers of cells that are constantly going through self-shedding and regeneration once every 30 days in repeated cycles. The layers may be broadly divided into two sections—the top epidermis and the underlying dermis. Histological studies of the skin show that a wrinkle is formed following a series of major cellular changes. During the early phase of aging (from age 35-45), there is a gradual and progressive slowing of cellular turnover and regeneration. This results in the skin getting thinner. As a result, the normally undulating ridge-like dermal-epidermal junction (DEJ) becomes flatter. This flatness reduces the surface area of nutritional exchange between the underlying dermis on the bottom and the epidermis on top.

Reduced nutrition to the epidermis from aging is one factor that causes cellular exhaustion and weakness. Without proper nutrition to the epidermis, cellular metabolism of the epidermal cell is slowed. Furthermore, the transportation of certain unwanted byproducts of cellular metabolism such as free radicals are reduced. The accumulation of such free radicals within the cell may lead to undesirable mutational damages in the cell and ultimately cancer.

The adhesion in the DEJ is normally supplied by Collagen 4 (a multi-sheet structure or basal layer) and collagen 7 (anchored to the sheets structure). The progressive loss of nutrients to the DEJ slows the circulation of the messengers that serve to promote the neo-synthesis process of such collagen. Without an optimal amount of collagen, the skin sags even more, propagating the dearth of nutrients. Paradoxically, matured aging skin contains more elastin, which the body uses to fill in the empty space left by the deficiency of collagen. Such elastin, unfortunately, is fragmented, calcified, and contains excessive lipids. In addition to the loss of skin thickness due to the lack of collagen support, the aging or aged skin is more loose and lacks elasticity. These two properties are hallmarks of wrinkles. This process of aging and appearance of wrinkles is accelerated during the later phase of aging (age 45 and higher). By age 50, very few people can escape wrinkles.

While genetics play a significant role, the number of wrinkles present is highly dependent on the amount of sun exposure. The lines in a "lived-in face," especially for those who spend a considerable amount of time outdoors, is a consequence in part of oxidative damage due to overexposure to ultraviolet (UV) sunlight—both UVA (responsible for tanning, wrinkling, and melanoma) and UVB (responsible for sunburn and basal and squamous cell carcinoma). UV light may further damage skin by increasing the production of proteolytic enzymes that break down collagen, the connective tissue located beneath the dermis.

The present disclosure provides the use of a disclosed composition, pharmaceutical composition or formulation comprising a peptide of the disclosure (e.g. QHREDGS (SEQ ID NO: 1)) for improving the aesthetic appearance or condition of the skin of an animal or a subject, as known in the art or as described herein, using the disclosed compositions and pharmaceutical compositions, e.g., administering or contacting the skin of an animal or a subject with a therapeutic effective amount of the composition or pharmaceutical composition for a time sufficient to improve the aesthetic appearance of the skin. In one aspect, the subject is a mammal. Preferably, the subject is human. The terms "subject" and "patient" are used interchangeably herein.

The present disclosure provides a method for improving the aesthetic appearance of skin. Improving the aesthetic appearance of skin includes but are not limited to reducing dermatological signs of chronological aging, photo-aging, hormonal aging, and/or actinic aging; preventing and/or reducing the appearance of lines and/or wrinkles; reducing the noticeability of facial lines and wrinkles, facial wrinkles on the cheeks, forehead, perpendicular wrinkles between the eyes, horizontal wrinkles above the eyes, and around the mouth, marionette lines, and particularly deep wrinkles or creases; preventing, reducing, and/or diminishing the appearance and/or depth of lines and/or wrinkles; improving the appearance of suborbital lines and/or periorbital lines; reducing the appearance of crow's feet; rejuvenating and/or revitalizing skin, particularly aging skin; reducing skin fragility; preventing and/or reversing of loss of glycosaminoglycans and/or collagen; ameliorating the effects of estrogen imbalance; preventing skin atrophy; preventing, reducing, and/or treating hyperpigmentation; minimizing skin discoloration; improving skin tone, radiance, clarity and/or tautness; preventing, reducing, and/or ameliorating skin sagging; improving skin firmness, plumpness, suppleness and/or softness; improving procollagen and/or collagen production; improving skin texture and/or promoting retexturization; improving skin barrier repair and/or function; improving the appearance of skin contours; restoring skin luster and/or brightness; minimizing dermatological signs of fatigue and/or stress; resisting environmental stress; replenishing ingredients in the skin decreased by aging and/or menopause; improving communication among skin cells; increasing cell proliferation and/or multiplication; increasing skin cell metabolism decreased by aging and/or menopause; retarding cellular aging; improving skin moisturization; enhancing skin thickness; increasing skin elasticity and/or resiliency; enhancing exfoliation; improving microcirculation; decreasing and/or preventing cellulite formation and any combinations thereof.

Symptoms of chronological aging include: dry and thin skin, fine wrinkles, abnormal blood vessels, age spots, and benign and malignant skin tumors. Young skin renews itself more frequently than older skin. The top layers thereby lose more moisture due to the aging process, and older skin has a dryer and more dehydrated appearance. Diminished production of collagen leads to fine wrinkles initially observed around the eyes (commonly known as "crow's feet"), forehead, and other sun-exposed areas. More pronounced effects include furrows at the site of facial expression lines and sagging folds over the eyelids, neck, jaw, and arms. Within the many small, delicate blood vessels supplying nutrients to the skin, abnormalities develop. This is particularly conspicuous over the nose and cheeks. Age spots are pigmentations that surfaced as a result of a deregulation of pigment cells in sun-exposed areas.

The aesthetic improvement of human skin may be an improvement of any attribute or characteristic of skin, including without limitation: (a) treatment, reduction, and/or prevention of fine lines or wrinkles; (b) reduction of skin pore size; (c) improvement in skin thickness, plumpness, and/or tautness; (d) improvement in skin smoothness, suppleness and/or softness; (e) improvement in skin tone, radiance, and/or clarity; (f) improvement in procollagen, and/or collagen production; improvement in maintenance and remodeling of elastin; improvement in skin texture and/or promotion of retexturization; (g) improvement in skin barrier repair and/or function; (h) improvement in appearance of skin contours; (i) restoration of skin luster and/or brightness; (j) replenishment of essential nutrients and/or constituents in the skin; (k) improvement of skin appearance decreased by aging and/or menopause; (l) improvement in skin moisturization; (m) increase in skin elasticity and/or resiliency; (n) treatment, reduction, and/or prevention of skin sagging; (o) improvement in skin firmness; (p) reduction of pigment spots and/or mottled skin; and (q) improvement of optical properties of skin by light diffraction or reflection.

The present disclosure also provides a method for treating and/or preventing scarring of a wound or a skin comprising topically applying to an area of the skin in need thereof a topical composition, a pharmaceutical composition or a formulation comprising an effective amount of a peptide of the invention, for a time sufficient to improve the appearance of the skin.

The present disclosure also provides a method for preventing or treating aging of a skin comprising topically applying to an area of the skin in need thereof a topical composition, a pharmaceutical composition or a formulation comprising an effective amount of a peptide of the invention, for a time sufficient to improve the appearance of the skin (e.g. to remediate, reverse, reduce, ameliorate, or prevent dermatological signs of aging). Skin aging includes but is not limited to rhytids, wrinkles, jowls, sun damage, dull appearance of skin, loss of skin tautness, keratosis, hyperpigmentation, melasma, solar lentigo, solar keratosis, dermatoheliosis or skin discoloration.

The present disclosure provides a method for regenerating collagen in a human skin area, enhancing the production of collagen and/or HA in human skin comprising topically applying to an area of the skin in need thereof (e.g., sagging skin, thinning skin, skin suffering from wrinkles and fine lines, etc.) a topical composition, a pharmaceutical composition or a formulation comprising an effective amount of a peptide of the invention, for a time sufficient to improve the appearance of the skin. In some embodiments, the subject has a dermis wound in the skin area. In some embodiments, the subject has skin redness in the skin area. In some embodiments, the subject has wrinkles in the skin area. In some embodiments, the skin area is susceptible to developing wrinkles. In some embodiments the skin area is in the forehead, the cheeks, the neck or around the eye of the subject.

The present disclosure provides a method for preventing or decreasing the presence of wrinkles and/or fine lines on the skin human skin (typically, skin of the face) or for reducing the severity of, reducing the number of, or preventing or forestalling the onset of, wrinkles or fine lines on human skin comprising topically applying to an area of the skin in need thereof (e.g., sagging skin, thinning skin, skin suffering from wrinkles and fine lines, etc.) a topical composition, a pharmaceutical composition or a formulation comprising an effective amount of a peptide of the invention, for a time sufficient to improve the appearance of the skin. The composition may optionally further comprise a retinoid (e.g., retinol or retinyl palmitate) and/or an alpha-hydroxy acid (e.g., glycolic acid) and/or a beta-hydroxy acid (e.g., salicylic acid or derivative) in amounts effective to improve the appearance of skin.

The effect of a composition on the formation or appearance of fine lines and wrinkles can be evaluated qualitatively, e.g., by visual inspection, or quantitatively, e.g., by microscopic or computer assisted measurements of wrinkle morphology (e.g., the number, depth, length, area, volume and/or width of wrinkles per unit area of skin).

The present disclosure provides a method for decreasing skin redness in a subject in need thereof comprising administering a topical composition, a pharmaceutical composition or a formulation comprising an effective amount of a peptide of the invention, for a time sufficient to improve the appearance of the skin. Skin redness may result from, but is not limited to, acne, contact irritation, skin sensitivity, rosacea, eczema, surgery, laser treatment, allergies, microdermabrasion, dermabrasion or a combination thereof.

The present disclosure provides a method for decreasing, preventing, reducing the severity of, or forestalling the onset of acne in a subject in need thereof comprising administering a topical composition, a pharmaceutical composition or a formulation comprising an effective amount of a peptide of the invention, for a time sufficient to improve the appearance of the skin.

The present disclosure provides a method for treating thin skin comprising administering a topical composition, a pharmaceutical composition or a formulation comprising an effective amount of a peptide of the invention, for a time sufficient to improve the appearance of the skin. "Thin skin" is intended to include skin that is thinned due to chronological aging, menopause, or photo-damage and skin that is thinning prematurely. In some embodiments, the treatment is for thin skin in men, whereas other embodiments treat thin skin in women, pre-menopausal or post-menopausal, as it is believed that skin thins differently with age in men and women, and in particular in women at different stages of life.

The present disclosure provides a method of preventing or forestalling aging skin in individuals that have not manifested signs of skin aging (most commonly in individuals under 25 years of age) comprising administering a topical composition, a pharmaceutical composition or a formulation comprising an effective amount of a peptide of the invention, for a time sufficient to improve or prevent the appearance of skin aging. The method may also reverse or treat signs of aging once manifested as is common in individuals over 25 years of age, or to slow the progression of dermatological aging in such individuals.

The invention also provides a method for ameliorating and/or preventing signs of human skin photo-aging and intrinsic aging comprising administering a topical composition, a pharmaceutical composition or a formulation comprising an effective amount of a peptide of the invention, for a time sufficient to ameliorate or prevent appearance of skin aging.

The present disclosure provides a method for reducing sebum production or improving the appearance of skin affected by cellulite, and/or reduce unwanted lipogenesis or increase lipolysis comprising administering a topical composition, a pharmaceutical composition or a formulation comprising an effective amount of a peptide of the invention, for a time sufficient to improve the appearance of the skin. The pharmaceutical composition or formulation may include one or more additional agents such as anti-acne ingredients (e.g., salicylic acid, benzoyl peroxide and other peroxides, sulfur, retinoids, etc.) in the case of a facial composition, or, in the case of a cellulite treatment, the formulation may comprise any ingredients suitable for treatment of cellulite, including without limitation, perilla oil and other unsaturated fatty oils and omega-3 fatty acids such as alpha-linolenic acid; caffeine; theophylline; xanthines; retinoids (e.g., retinol); and the like. A cellulite treatment according to the invention will typically be applied topically to skin suffering from cellulite, including skin of the buttocks and thighs for a period of time sufficient to improve the appearance thereof, including for example, daily treatment for at least four weeks, at least eight weeks, at least twelve weeks, or longer. In one embodiment, the compositions are topically applied to treat acne.

The present disclosure provides a method for treating and/or preventing hyper-pigmentation of skin and/or of the hair, for example, to lighten skin or hair comprising administering a topical composition, a pharmaceutical composition or a formulation comprising an effective amount of a peptide of the invention, for a time sufficient to improve the appearance of the skin. Hyper-pigmentation includes any coloration of an individual's skin or hair that is darker than desired by the individual and that is caused by melanocytes. Such unwanted pigmentation may also be called discoloration. Hyper-pigmented areas of the skin include areas of discrete or mottled hyper-pigmentation. Areas of discrete hyper-pigmentation can be distinct, uniform areas of darker color and may appear as brown spots or freckles on the skin, including marks commonly called pigment spots or "age spots." Areas of mottled hyper-pigmentation of the skin can be dark blotches that are larger and more irregular in size and shape than areas of discrete pigmentation. Areas of hyper-pigmentation also include areas of tanned skin, for example, skin tanned due to UV exposure. Hyper-pigmented hair includes any shade of hair that is darker than desired.

Treating hyper-pigmentation or hyper-pigmented skin/hair include but are not limited to eradicating, reducing, ameliorating, or reversing one or more of the unwanted features associated with hyper-pigmentation, such as producing an appreciable lightening of the skin or hair in the affected area. Lightening hyper-pigmented areas of the skin may be desirable and may include but are not limited to: diminishing age spots; lightening a suntan; evening or optimizing skin tones, (e.g., in areas of mottled hyper-pigmentation; in treating melasmic and chloasmic patches, freckles, after-burn scars, and post-injury hyper-pigmentation). Preventing hyper-pigmentation or hyper-pigmented skin includes but is not limited to affording skin, not yet affected by hyper-pigmentation, a benefit that serves to avoid, delay, forestall, or minimize one or more unwanted features associated with skin hyper-pigmentation, such as reducing the darkness or size of hyper-pigmented areas that eventually develop.

In some aspects, the composition, pharmaceutical composition or formulation comprising a peptide of the disclosure is topically applied to the skin in effective amounts, by which is meant an amount sufficient to achieve a measurable aesthetic improvement of human skin. In some embodiments, the composition, pharmaceutical composition or formulation is administered at least once per day, at least twice per day, and least 3 times per day, at least 4 times per day or at least 5 times per day. In some embodiments, the composition, pharmaceutical composition or formulation is administered for a period of at least one week, at least 2 weeks, at least 3 weeks, at least 4 weeks, at least 5 weeks, at least 6 weeks, at least 7 weeks, at least 8 weeks, at least 9 weeks, at least 10 weeks, at least 11 weeks or at least 12 weeks. In some embodiments, the composition, pharmaceutical composition or formulation of the disclosure will be applied to the skin in an amount from about 0.001 to about 100 mg/cm$^2$, more typically from about 0.01 to about 20 mg/cm$^2$, or from about 0.1 to about 10 mg/cm$^2$.

VI. Articles of Manufacture or Kits

This invention encompasses an article of manufacture of a kit which, when used by the medical practitioner, can simplify the administration of appropriate amounts of compositions, pharmaceutical formulations or topical formulations of the invention, to a patient.

In one aspect of the invention, an article of manufacture containing materials useful for the treatment and/or prevention of skin conditions described above is provided. The article of manufacture comprises a container and a label or package insert on or associated with the container. Suitable containers include, for example, bottles, vials, syringes, IV solution bags, etc. The containers may be formed from a variety of materials such as glass or plastic. The containers may provide protection from photo-degradation. The container holds a composition which is by itself or combined with another composition effective for treating and/or preventing the condition. At least one active agent in the composition is a peptide of the invention. The composition may further comprise a carrier described herein (e.g. a hydrogel and/or chitosan). The label or package insert indicates that the composition is used for treating the condition of choice. Moreover, the article of manufacture may comprise (a) a first container with a composition contained therein, wherein the composition comprises a peptide of the invention; and (b) a second container with a composition contained therein, wherein the composition comprises a further otherwise therapeutic agent. The article of manufacture in this embodiment of the invention may further comprise a package insert indicating that the compositions can be used to treat and/or prevent a particular condition. Alternatively, or additionally, the article of manufacture may further comprise a second (or third) container comprising a topically acceptable vehicle or a pharmaceutically acceptable buffer, such as bacteriostatic water for injection (BWFI), phosphate-buffered saline, Ringers solution and dextrose solution. It may further include other materials desirable from a commercial and user standpoint, including other buffers, intravenous cannulation devices, drip bags, patches, topical gels, pumps, diluents, filters, auto-injectors, inhalers, needles and syringes.

EXAMPLES

The following are examples of methods and compositions of the invention. It is understood that various other embodiments may be practiced, given the general description provided above.

Example 1—QHREDGS (SEQ ID NO: 1) Prevents Changes Associated with Scarring Using Dermis-On-a-Chip Model Disclosed herein is a new dermis-on-a-chip model to assess the effects of the QHREDGS (SEQ ID NO: 1) peptide on mechanisms involved in scarring. The dermis-on-a-chip model consists of adult dermal fibroblasts encapsulated into collagen-chitosan hydrogel seeded into a microwell fitted with 2 parallel elastomeric wires. During the tissue remodelling process, the fibroblasts exert tractional forces that compact the gel into a cylindrical tissue. In some cases, myofibroblast over-activation leads to tissue breakage due to the excessive pulling on the hydrogel matrix. A combination of functional readouts together with immunostaining and second harmonic generation microscopy was used to assess the anti-scarring behaviour of peptide modified gel. Anti-scarring properties were defined by: higher survival of intact tissues, slower gel compaction, and higher native collagen regeneration.

Figure 2B:
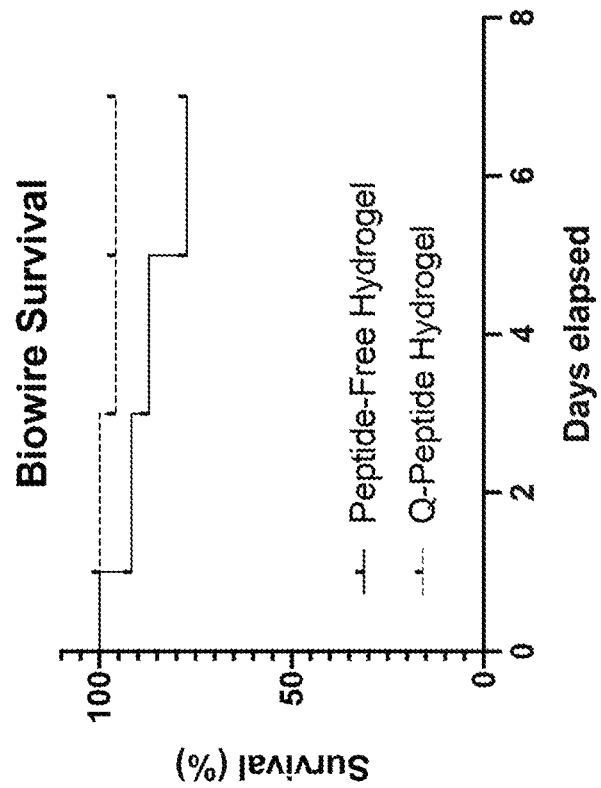
FIGS. 2A-2B are a series of graphs showing that Q-peptide slows gel compaction and increases the number of intact tissues over 7 days of culture in accordance with an example of the present disclosure. Solid line=Peptide-Free hydrogel; Dashed line=Q-peptide hydrogel. ** P<0.0001, * P<0.0005, N=16 per group.
Figure 2A:
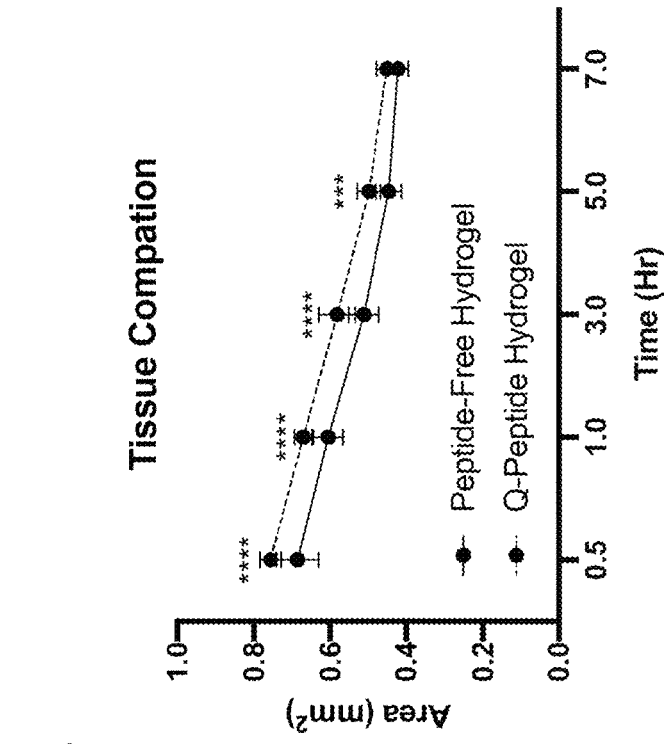
Figure 3:
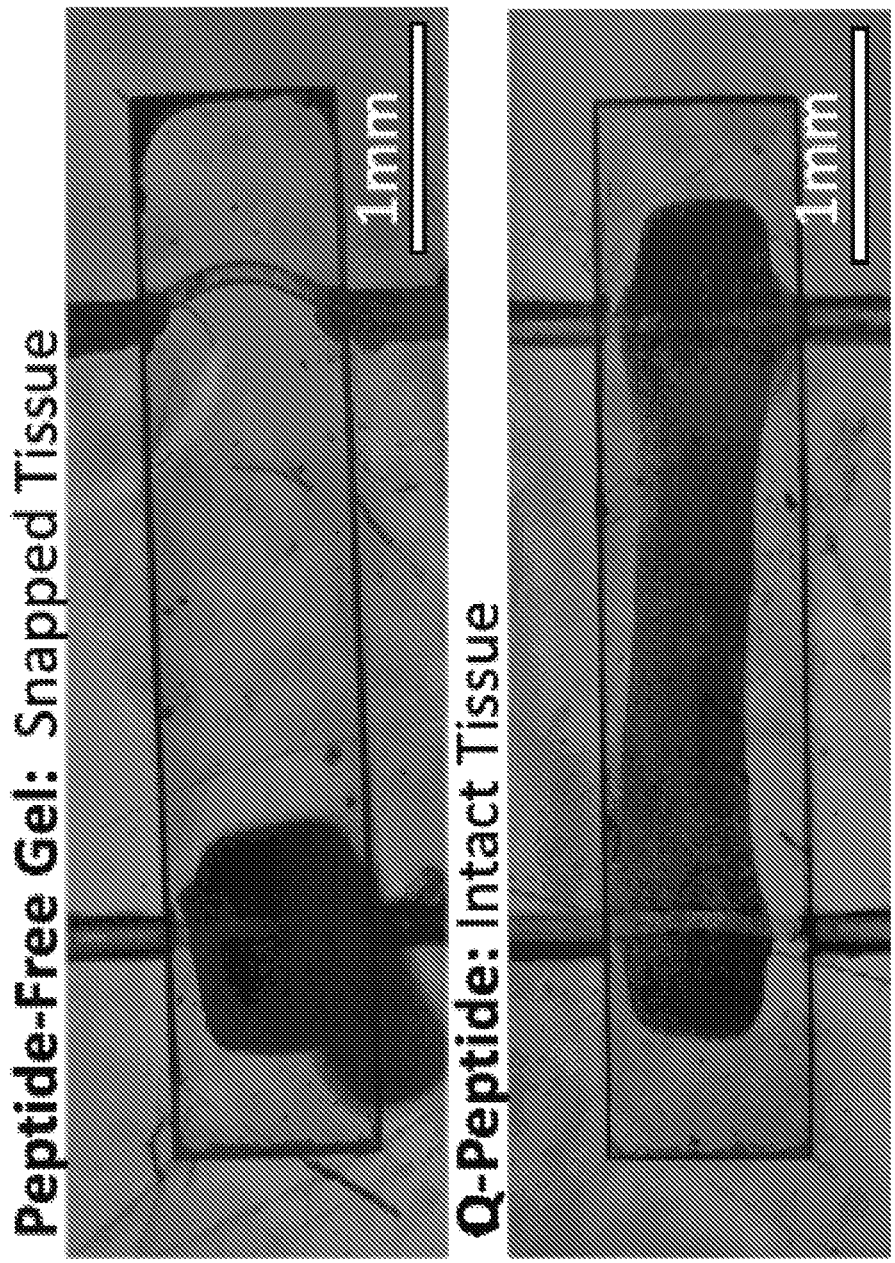
FIG. 3 is a series of representative brightfield images showing snapped tissues and intact tissues on a dermis-on-a-chip model in an example of the present disclosure.

Fibroblasts, seeded in Q-Peptide hydrogel and Peptide-Free hydrogel, compacted into tissues that were assessed over a one week period. Representative images of the tissues visually demonstrate the differences in compaction, within the first three hours (FIG. 1). Significant differences in tissue compaction rate were observed between the Q-peptide and Peptide-Free control (FIG. 2A and FIG. 2B), within the first seven hours after cell seeding. In addition, tissues were assessed daily to identify those that broke apart due to the excessive tractional forces (FIG. 3). A survival curve shown in FIG. 2B summarizes the daily changes in the number of intact tissues between the Q-Peptide hydrogel and the Peptide-Free hydrogel control, indicating an appreciably lower number of intact tissues in the Peptide-Free hydrogel compared to the Q-peptide hydrogel.

Figure 4:
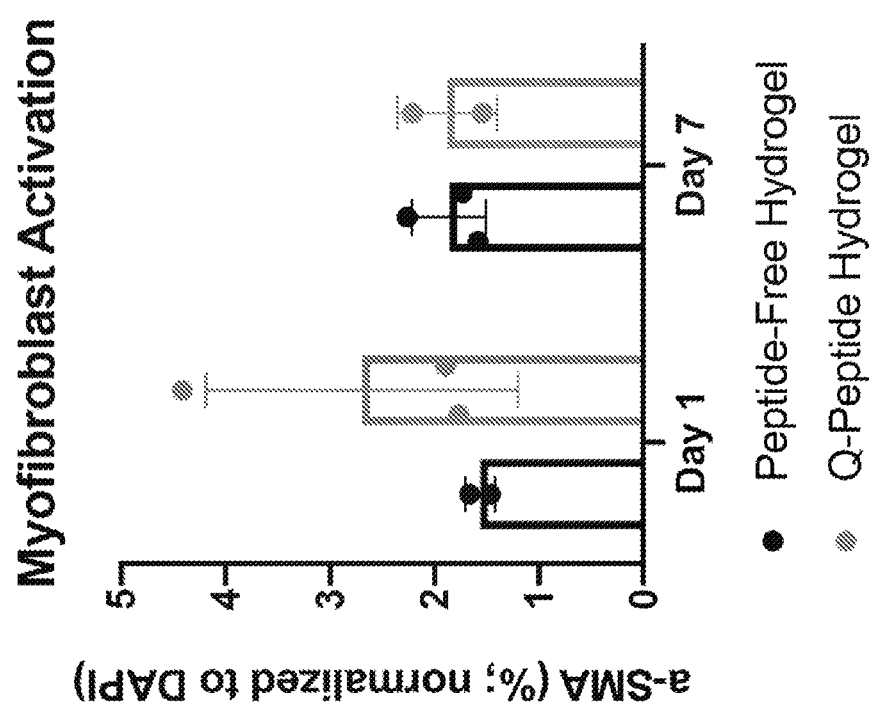
FIG. 4 shows a quantification of a-SMA staining was quantified, normalized to DAPI counterstain in an example of the present disclosure. Per tissue, 3-4 images were taken for quantification purposes. Peptide-Free hydrogel: N=2-3; Q-Peptide Hydrogel: N=2-3

Fibroblasts are known to undergo a transition to myofibroblasts. This transition results in an enhanced force generation within tissues, leading to pathological diseases such fibrosis. In order to investigate the differences in tissue compaction and tissue survival, tissues were stained for α-smooth muscle actin (α-SMA), a marker of activated myofibroblasts. Immunostaining demonstrated a small percentage of cells undergoing activation in each group. α-SMA staining was quantified and normalized to DAPI counterstain. No significant differences were observed after 7 days, between treatment with Q-peptide hydrogel and Peptide-free hydrogel control (FIG. 4).

Figure 5:
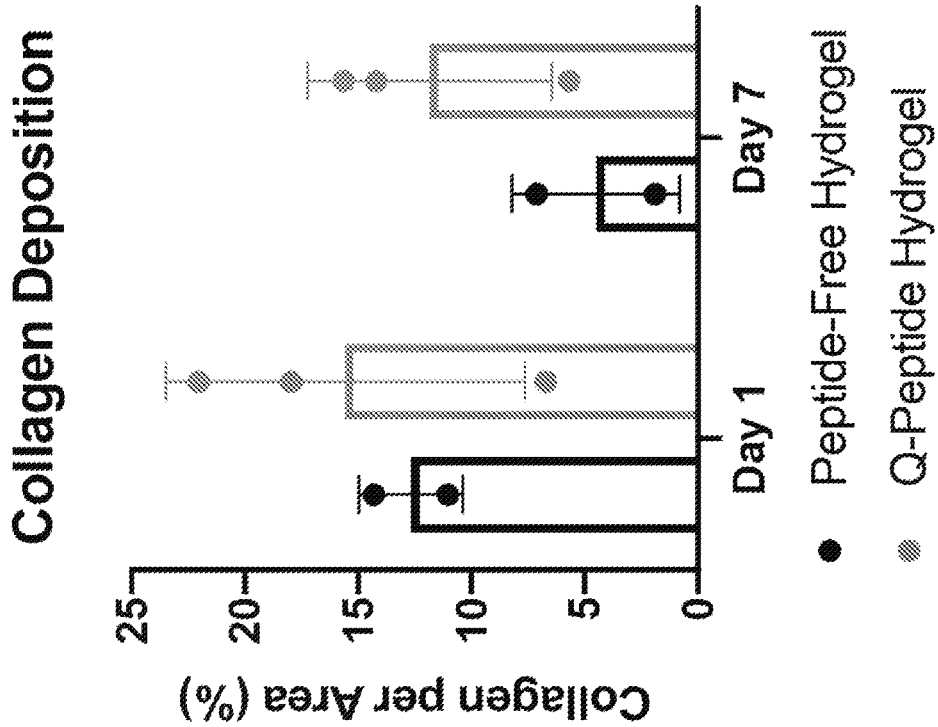
FIG. 5 shows Second Harmonic Generation (SHG) microscopy analysis of dermis-on-a-chip model in an example of the present disclosure. Representative images were taken for SHG analysis of dermis-on-a chip model with a Q-peptide Hydrogel or Peptide-Free Hydrogel on Day 1 and Day 7. Signal from collagen was quantified. Collagen per area is the average of 2-3 images/tissue. Sample size was N=2 for Peptide-Free hydrogel and N=3 for Q-Peptide hydrogel.

Second Harmonic Generation (SHG) microscopy was utilized to quantify new collagen deposition. SHG is a non-invasive technique that only registers signal from the collagen in native configuration, consistent with appropriate matrix remodelling. Disorganized fragments of collagen are not registered by the technique. Collagen deposition per area was measured using SHG on dermis-on-chip model with Q-Peptide Hydrogel or Peptide-Free Hydrogel control (FIG. 5). The results were consistent with the alpha smooth muscle actin, α-SMA, staining. The results demonstrate higher collagen restoration in the Q-Peptide in comparison to the Peptide-Free hydrogel.

Figure 6:
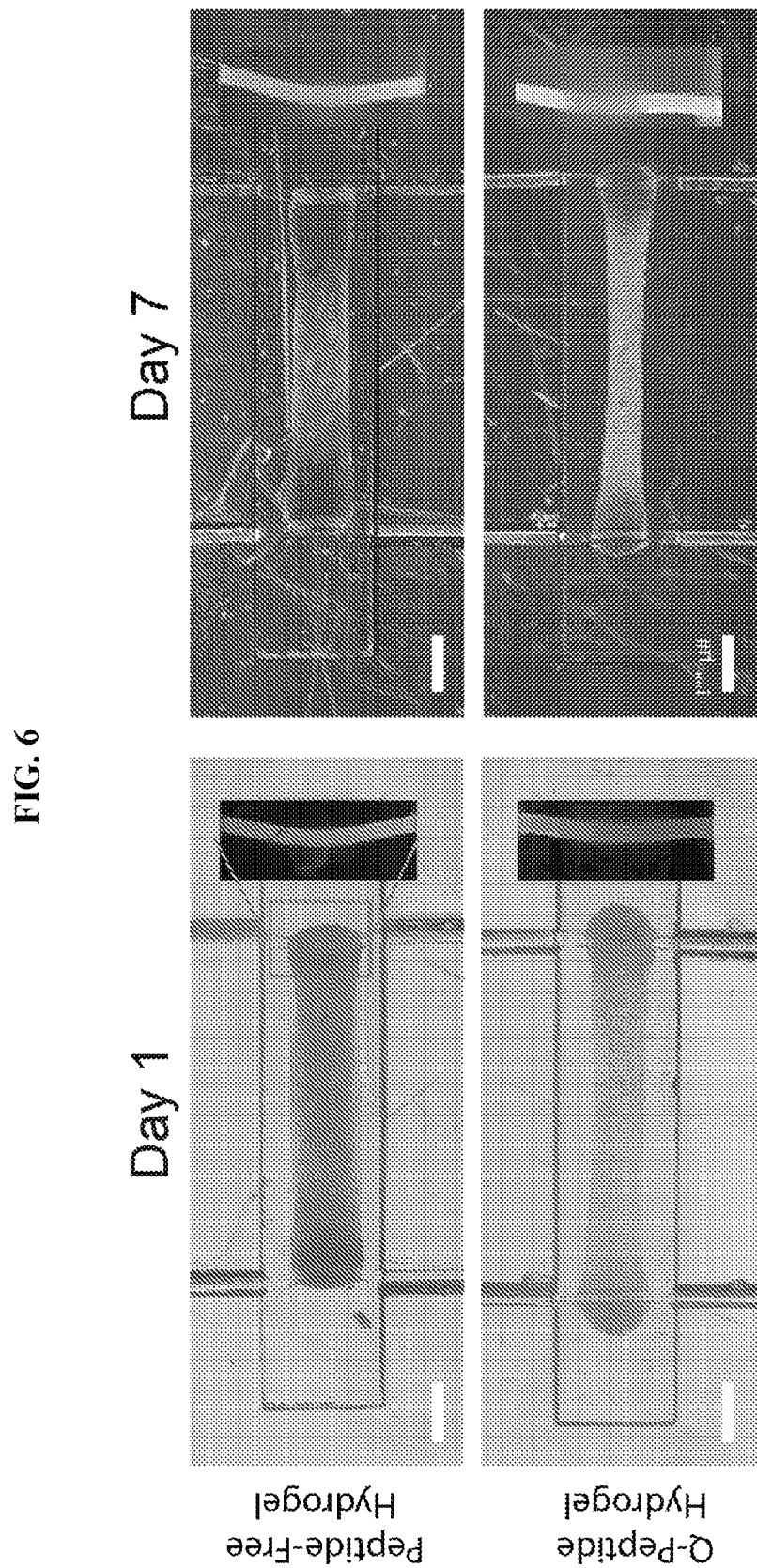
FIG. 6 shows a series of representative brightfield images of tissues on dermis-on-chip model in an example of the present disclosure. Passive tension is significantly lower in Q-Peptide hydrogel tissues compared to Peptide-Free hydrogel tissues by day 7. Inline image, as indicated by the box, is the blue autofluorescence of the wire. Scale bar=200 µm.

A unique feature of the dermis-on-a-chip platform is the ability to measure the passive force the tissue exerts. The material used to fabricate the wires in the dermis-on-a-chip platform naturally exhibit blue autofluorescence (FIG. 6). Passive tension was calculated using a custom MatLAB script. While there is no significant difference in passive force after 1 day of culture (FIG. 7A), there is a significant difference after 7 days (FIG. 7B). The Q-Peptide hydrogel tissues have a significantly lower passive tension within the tissue when compared to the Peptide-Free hydrogel tissues (FIG. 7B). The higher passive force in the Peptide-Free hydrogel tissues may contribute to the higher failure rate of the tissues over the course of 7 days.

Example 2—Materials and Methods for Assessment Wound Healing in a Human to Mouse Xenograft Model Human Split Thickness Xenograft—Human skin was harvested and grafted as previously described. Briefly, full thickness adult skin samples were obtained with informed consent from abdominoplasty patients from the Foothills Medical Center in Calgary Alberta. Within 24 hours of procurement, the human skin was grafted onto the backs of mice. Full thickness skin wounds (2 cm$^2$) were created on the backs of adult athymic (Nu/Nu) mice. HSTGs were cut to the exact size and sutured into place. The wounds were bandaged for 10 days with a foam-based silver dressing held securely with and elastic adhesive bandage circumferentially around the abdomen.

Wound Creation—After 2-3 months of integration, a 4 mm full excisional wound was created on the HSTG, and the wound received one of the following treatments: 1) no treatment, 2) FDA approved wound management material (Primatrix®), 3) Collagen-chitosan gel without the peptide (Peptide-free hydrogel) and 4) Q-peptide modified gel. The wounds were covered with an adhesive, waterproof dressing (Tegaderm™ transparent film dressing, 3M™) to ensure a moist wound healing environment and maintain product contact with the wound. Wounds were photographed on day 0 immediately after treatment, and on days 14, 21, and 28 with a standard ruler positioned at the level of the wound. Using Fiji (ImageJ, NIH), the area of the HSTG was measured on days 0, 14, 21, and 28. HSTG contraction was measured by subtracting wound area on day 0 by day 28. A positive HSTG contraction area signified that the skin grafts had contracted by the day 28 endpoint, and 0 indicated that no skin graft contraction had occurred.

Hydrogel Formation—Using 1-ethyl-3-(3-dimethylaminopropyl) carbodiimide (EDC) chemistry, the QHREDGS peptide was conjugated to chitosan (UP-G213, Novamatrix) as previously described (Xiao, Y. et. al., Methods 2015, 84, 44-52). Once conjugated and lyophilized, the peptide-chitosan was mixed with collagen at a 1:1 ratio for a final concentration of 2.5 mg/mL. The collagen was neutralized to a pH of 7 with 1M sodium hydroxide. The hydrogel was kept on ice until 10 minutes before use, where it was brought up to room temperature to initiate gelling.

Endpoint Wound Collection—Tissue samples were collected on days 14 (N=3; no treatment N=2), 21 (N>3), and 28 (N>3). The mice were sacrificed, and the wounded skin grafts were biopsied and sectioned for histological analysis.

Histological Tissue Analysis—The tissue was fixed in 4% PFA, paraffin embedded, and sectioned into 5 μm thick sections. The sections were processed and stained with hematoxylin and eosin (H&E). Slides were scanned with a ScanScope XT whole slide scanner, and measured using Aperio ImageScope (v11, Aperio Technologies). As the panniculus carnosus, the thin muscle layer under the skin, was excised during skin grafting, it cannot be used as a visual landmark for the wound edge. Instead the wound gap was defined as the distance between the healthy dermis. Percent wound closure was calculated as:

$$\% \text{ wound closure} = \frac{(4 - \text{wound gap})}{4} \times 100\% \qquad \text{EQ5-1}$$

The epithelial gap was defined as the distance between the leading epithelial tongues, and the epithelial thickness was measured at 300 μm from the leading epithelial tongues where applicable, or at 3 points across the wound if the wound had 100% re-epithelialization. In these equations, 4 mm refers to the original wound size. Percent re-epithelialization was calculated as:

$$\% \text{ re-epithelialization} = \frac{(4 - \text{epithelial gap})}{4} \times 100\% \qquad \text{EQ5-2}$$

The wound thickness was defined as the distance between the top of the dermis to the top of the underlying subcutaneous tissue. Finally, the rete ridge ratio was calculated as:

$$\textit{Rete} \text{ ridge ratio} = \frac{(\text{Length of epidermis: dermis boundary across wound})}{\text{Length of skin surface across wound}} \times 100\% \qquad \text{EQ5-3}$$

Statistical Analysis—All results are presented as mean±SD. Statistical analysis was performed using GraphPad Prism 6. Normality and equality of variances was tested using Shapiro-Wilk test and Brown-Forsythe test respectively. Significance was calculated using either a one-way ANOVA. To identify significant differences between experimental groups, a Tukey's multiple comparisons test was employed. A value of P<0.05 was considered statistically significant. Data are presented as mean±SD n=3.

Figure 8:
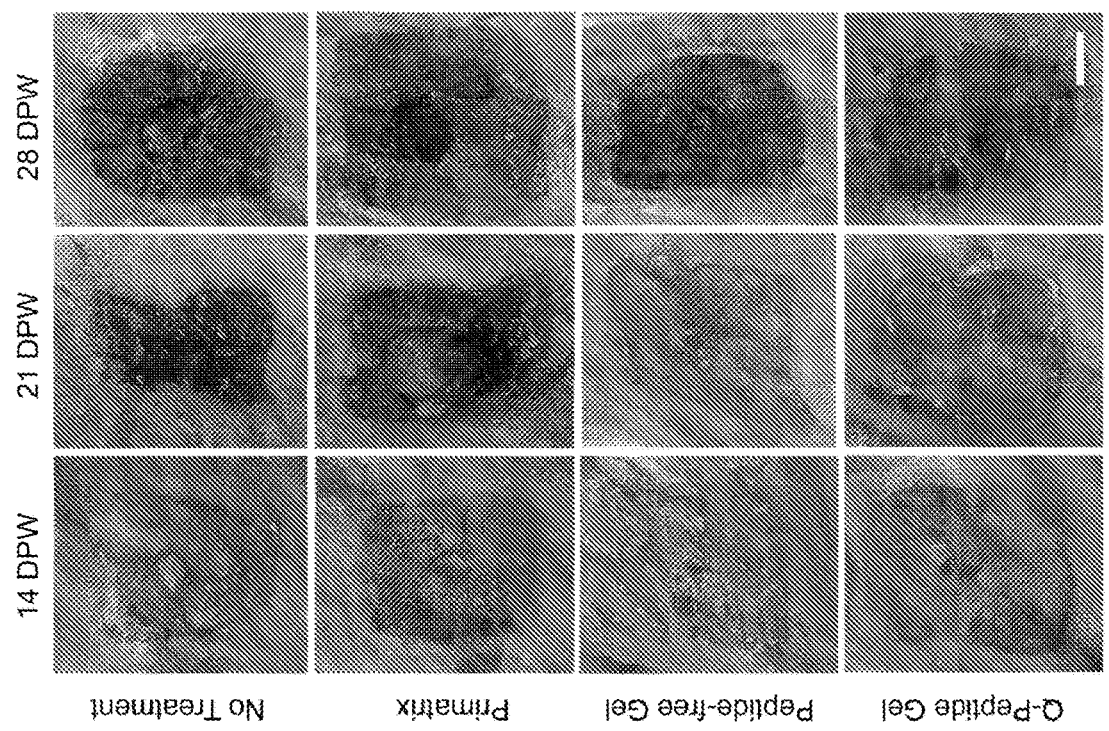
FIG. 8 shows treatment with QHREDGS (SEQ ID NO: 1) peptide conjugated hydrogel speeds wound closure without increasing the amount of wound contraction in an example of the present disclosure. Gross photographs of wounds at 14, 21, and 28 days post wounding (DPW). Representative images across timepoints are from three separate biological replicates.
Figure 9A:
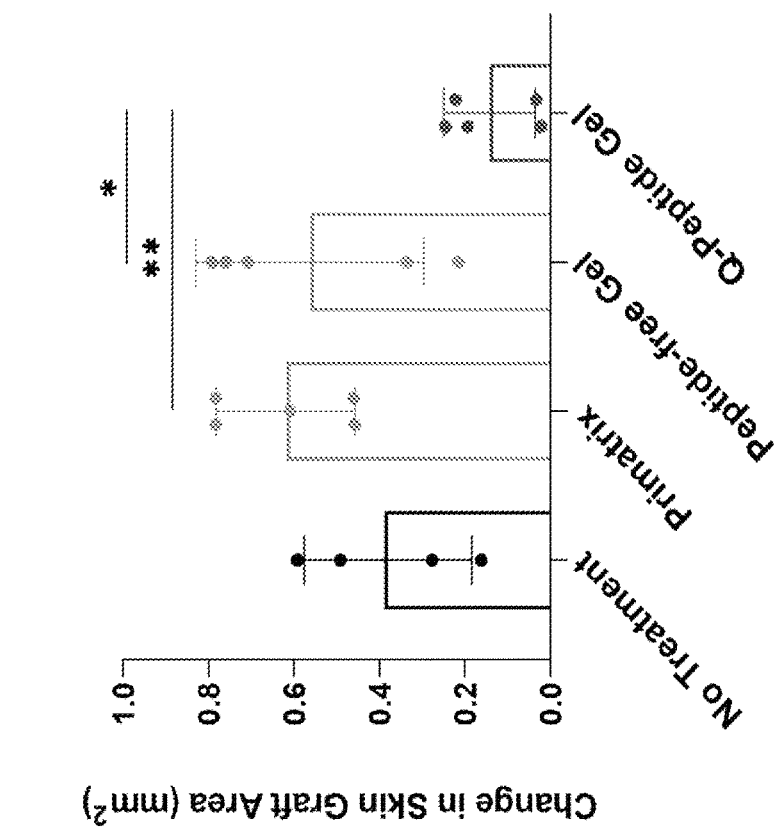
FIGS. 9A-9B show a quantification of wound closure and contraction of experiment from FIG. 13 in an example of the present disclosure.
Figure 9B:
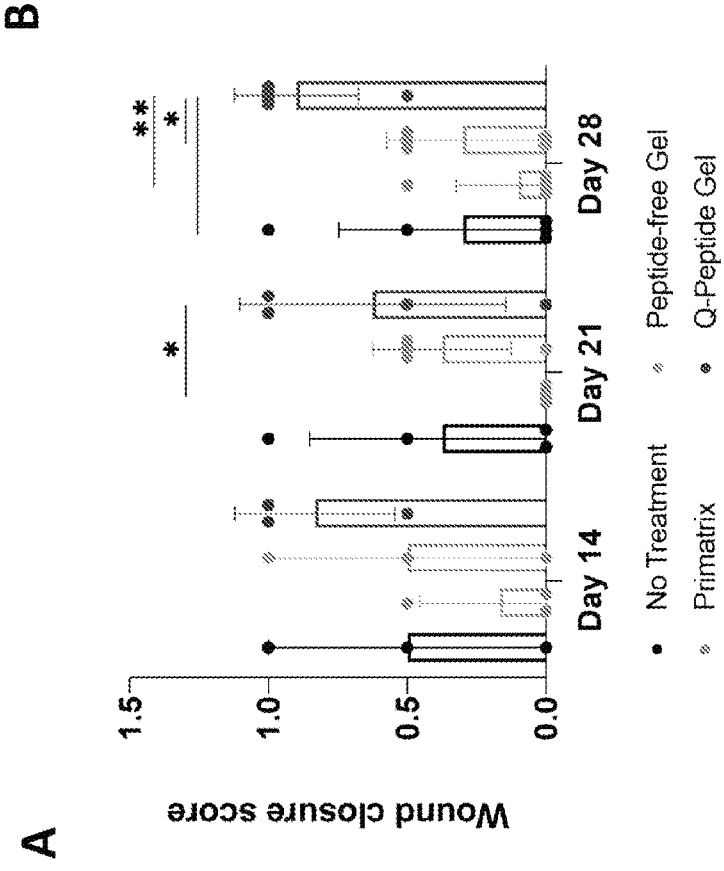

Example 3—Effect of Q-Peptide Hydrogel on Healing of Human Epidermis and Wound Contraction To examine the effect of the Q-Peptide hydrogel on wound healing in human epidermis, 4 mm wounds were treated with a no-treatment control (E), an FDA approved control (P, Primatrix®), a peptide-free hydrogel (H), and the Q-Peptide hydrogel (QH). Gross morphological images of the treated wounds were taken at the time of sacrifice to allow for gross observation of wound healing (FIG. 8). Wound appearance was evaluated by two blinded observers using a wound closure score where open wounds=0, closed wound with attached eschar (scab)=0.5, and closed wound with no eschar present=1. By day 28, the wound can be clearly seen in the no-treated control and in Primatrix®, with the empty hydrogel reducing the appearance of the wound, and the Q-Peptide hydrogel nearly eliminating the appearance of the wound. Wounds treated with the Q-Peptide hydrogel score significantly higher than all treatment groups, with all but one wound reaching full closure with no eschar by day 28 (FIG. 9A). As no panniculous carnous muscle is present in this model, identification of the original edge of the wound can be a challenge. Thus, in an effort to identify the contribution of wound contraction to wound closure, change in total graft area was measured after wound healing. Significantly less change was observed for a wound treated with Q-peptide hydrogel in comparison to a wound treated with peptide-free hydrogel and Primatrix®, suggesting less wound contraction following treatment with Q-peptide hydrogel (FIG. 9B).

Tissue sections from the middle of the wound were stained with H&E to evaluate the rate and quality of wound healing. Each section was given a histology score by an observer blinded to treatment to assess both the stage and quality of healing observed at each timepoint. Based on a previously published system, this score, ranging from 1 (no healing) to 12 (complete healing) encompassed features of wound healing such as the presence and organization of granulation tissue, persistence of inflammation, neovascularization, and re-epithelialization (Greenhalgh, D. G. et. al., *Am J Pathol* 1990, 136 (6), 1235-46). The histology score showed a trend (p<0.09) for improved rate and quality of wound healing following treatment with Q-peptide hydrogel, as evidenced by a higher score at day 14 (FIG. 10A). By day 14, wounds treated with the Q-Peptide hydrogel displayed significantly greater re-epithelialization of the wound (mean 90.9+/−1.2%) compared to all other treatments. Conversely, by day 21, Primatrix® exhibited significantly reduced re-epithelialization compared with the no treatment control and Q-peptide hydrogel. At day 28, though not significant, the negative impact of Primatrix® persisted as evidenced by 40% of wounds treated with Primatrix® (2/5) not exhibiting complete re-epithelialization compared with 100% of wounds in all other treatment groups (FIG. 10B). When compared with the thickness of unwounded adult abdomen skin epidermis (59.9+/−8.7 μm) (Khiao In, M. et. al., *Anat Histol Embryol* 2019, 48 (3), 207-217), an observable increase in thickness of the neoepidermis is present across all groups during early wound healing (day 14-21). At day 28, a significant decrease is identified in no treatment control compared to wounds treated with Q-peptide which most closely approximate that of unwounded adult human epidermis. Together this shows that the Q-Peptide hydrogel accelerates healing of human epidermis without increasing wound contraction.

Use of this xenograft model of wound healing identified that the most deficient wound healing is observed with wounds treated with Primatrix®. This dermal repair scaffold is derived from fetal bovine dermis and is particularly rich in type III collagen. It has demonstrated efficacy in the treatment of difficult wounds such as diabetic foot ulcers compared with both conservative therapy (Kavros, S. J. et. al., *Foot Ankle Spec* 2012, 5 (4), 230-4) and other biological scaffolds containing live cells (Karr, J. C. et. al., *Adv Skin Wound Care* 2011, 24 (3), 119-25).

Figures 11A, 11B, 11C, 11D:
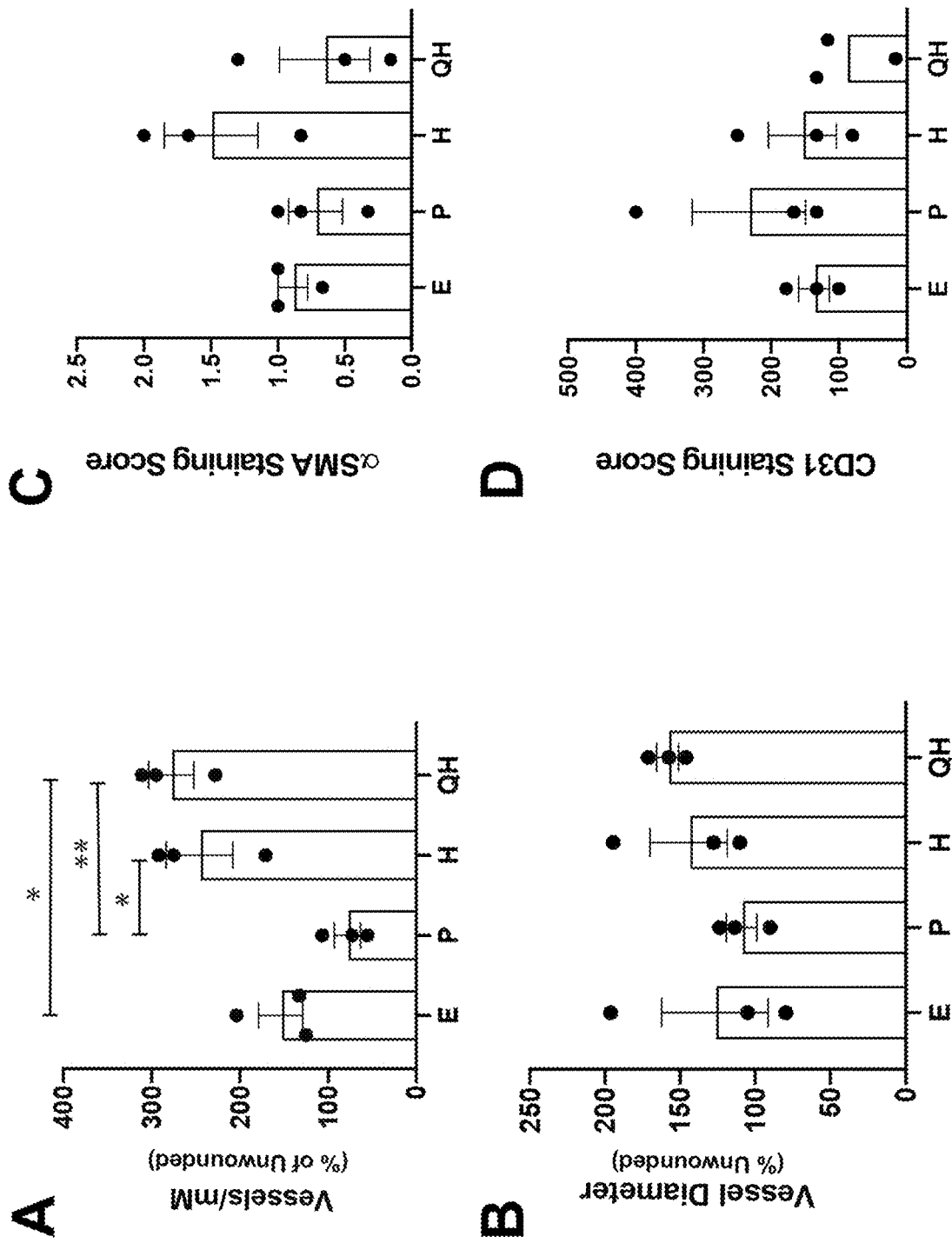
FIGS. 11A-11D show that treatment with Q-Peptide Hydrogel increases neovascularization of healing wounds at day 28 in an example of the present disclosure. Immunofluorescence staining of the central region of day 28 wounds for α-smooth muscle actin (aSMA) and CD31.

Example 4—Effect of Q-Peptide Hydrogel on the Neovascularization of Healing Dermis Wound To determine the effect of Q-peptide hydrogel on the neovascularization in the dermins during wound healing, sections from the center of day 28 wounds were immunostained for both CD31 and α-SMA. Blood vessels were identified not only by their morphologically-distinct phenotype, but also as co-staining for both CD31 and α-SMA. Quantification and measurement of diameter was performed by a blinded observer and completed for both the center of the wounded area as well as the surrounding, unwounded area for each graft. Results are then expressed as the % of each wounds own unwounded graft tissue to eliminate any variability introduced by the xenograft model. The total number of newly-formed blood vessels present within wounds treated with Q-peptide hydrogel was significantly higher than both no treatment and Primatrix® controls. A significant increase in the peptide-free hydrogel relative to Primatrix® suggest a portion of this effect on neovascularization is the result of the hydrogel itself and not only the result of the peptide (FIG. 11A). No significant differences were observed in the diameter of vessels across groups (FIG. 11B). A scoring system based on intensity of staining was then used to qualitatively explore the CD31 and α-SMA staining not associated with discrete vasculature (0=no staining, 0.5=slight, 1=moderate, 2=intense staining). No significant differences in α-SMA score were identified between treatments suggesting the presence of similar numbers of myofibroblasts persisting in the wounds at day 28 (FIG. 11C). Similarly, while no significant differences were observed in CD31 score, an observable reduction of CD31 staining intensity was consistently shown by Q-peptide hydrogel treated wounds suggesting that these wounds contained fewer migrating endothelial cells and thus displayed greater maturity of neovascularization (FIG. 11D).

Figures 12A, 12B, 12C, 12D:
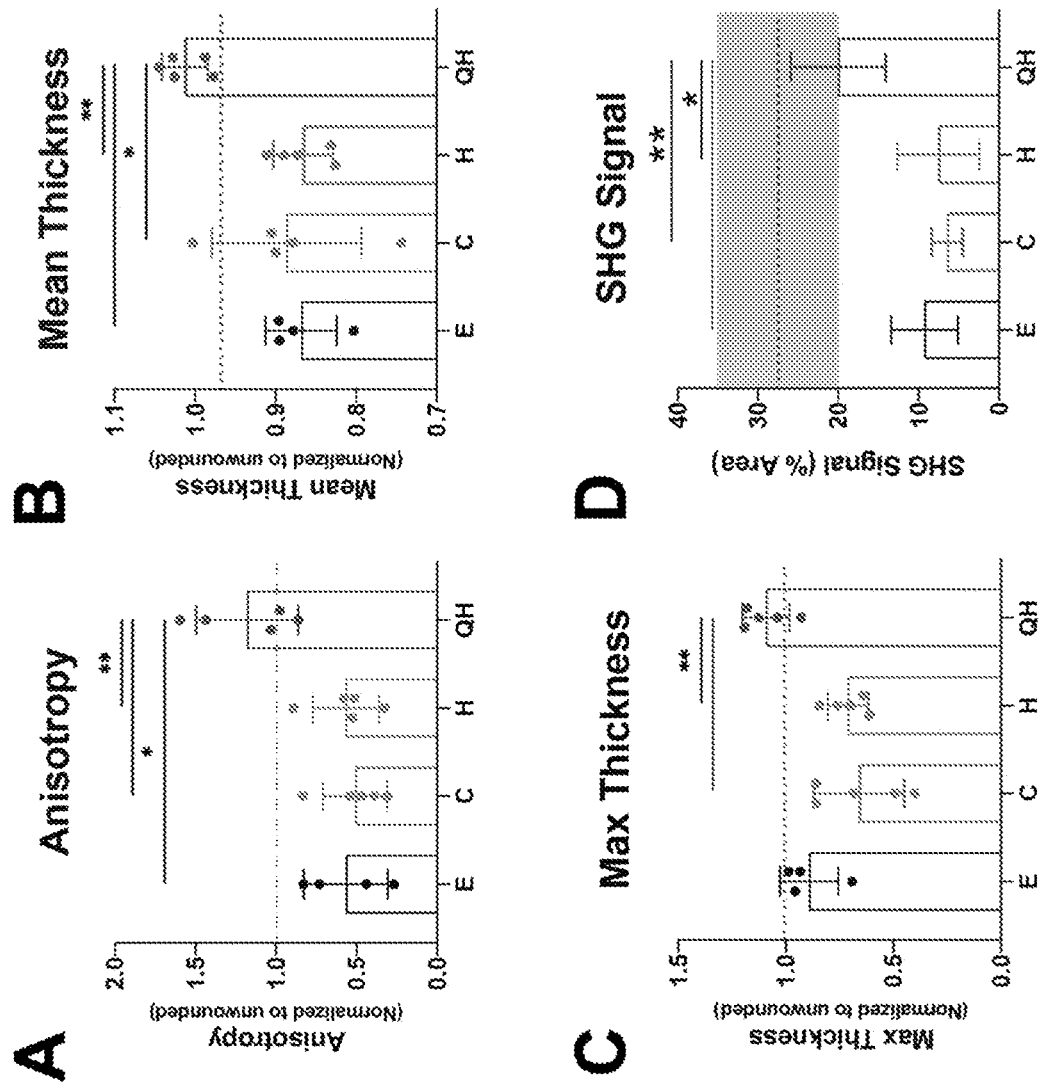
FIGS. 12A-12D show that Q-Peptide gel promotes normal collagen formation and minimizes fibrosis in the wound in an example of the present disclosure. Second harmonic generation of collagen fibers in an unwounded section of skin, and wounds with no treatment, or Primatrix®, Peptide-free gel, or Q-Peptide gel on day 28. Collagen fibers in the wounds treated with the Q-Peptide gel appear similar to those in unwounded skin, as quantified by Anisotropy (FIG. 12A), mean thickness (FIG. 12B), and max thickness (FIG. 12C). Second harmonic generation (SHG) signal is shown in FIG. 12D.
Figure 13:
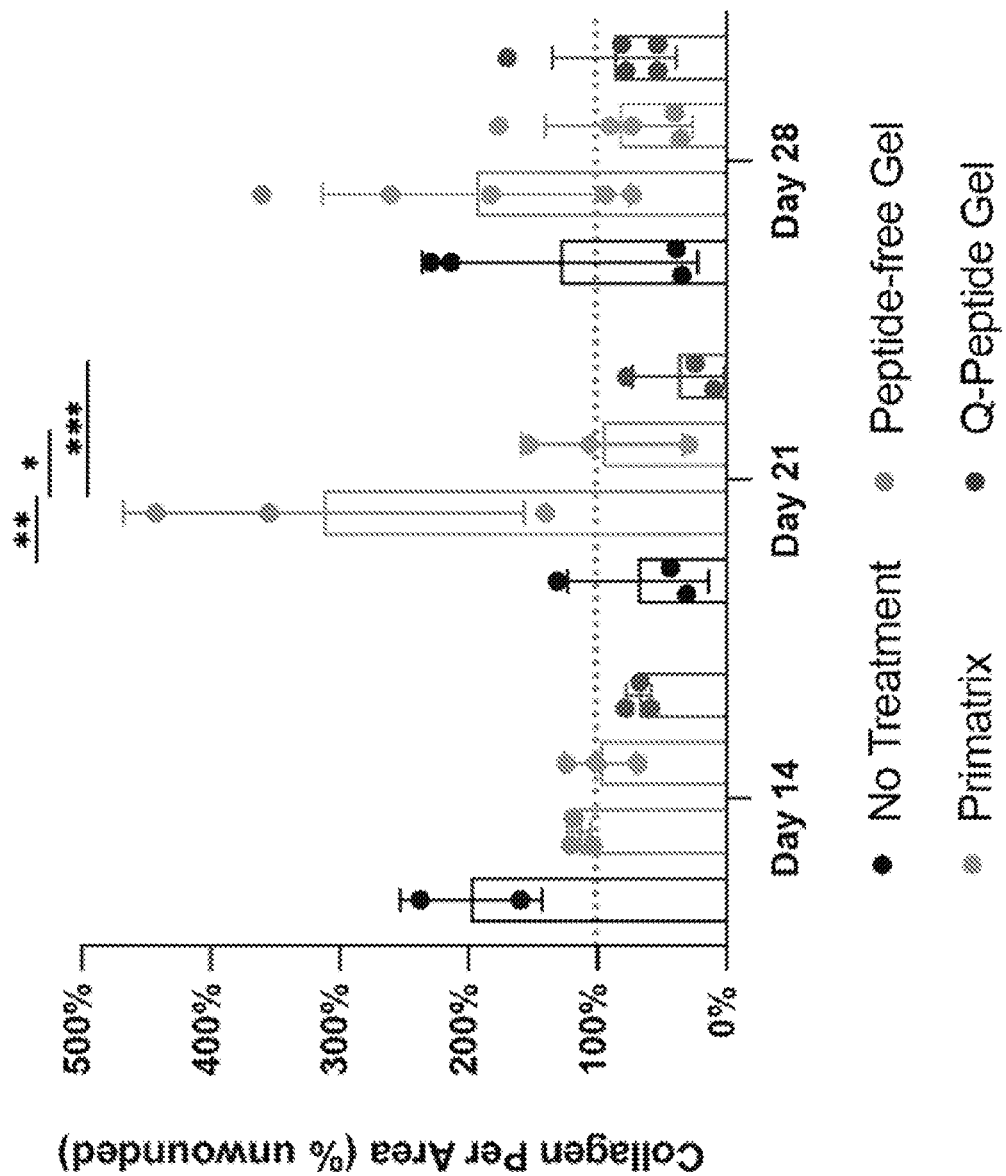
FIG. 13 shows Masson's trichrome staining of wounds treated with i) non-treatment, ii) Primatrix®, iii) Peptide-free gel, and iv) Q-peptide gel in an example of the present disclosure. Collagen per volume area of Masson's Trichrome stained images on days 14, 21, and 28. Data are normalized to unwounded skin graft. Scale bar 50 µm. Data are presented as mean±SD. *=p<0.05, =p<0.01, *=p<0.001. E=No treatment, P=Primatrix®, H=Peptide free Hydrogel, QH=Q-peptide Hydrogel n=3-5

Example 5—Effect of Q-Peptide Gel on Fibrosis in the Dermis Following Wound Healing Unstained tissue sections from unwounded xenografts as well as the center of wounds from each treatment group were subjected to second harmonic generation (SHG) of collagen. Collagen deposition mostly occurs in the dermis. Following normalization to unwounded section in the surrounding area of each wound in the xenograft, it was discovered that collagen fibers in the wounds treated with the Q-Peptide gel appear similar to those in unwounded skin, as quantified by Anisotropy (FIG. 12A), mean fiber thickness (FIG. 12B), and maximum fiber thickness (FIG. 12C). The amount of newly deposited collagen was the same in the Q-Peptide gel treated wounds compared to the uninjured skin (FIG. 12D). Masson's trichrome staining of the middle of healing wounds allowed measurement of collagen per volume area on days 14, 21, and 28 (FIG. 13). This shows that treatment of a wound with Q-peptide gel minimizes fibrosis following wound healing.

Example 6—Effect of Q-Peptide Gel on Scar Formation in the Dermis Following Wound Healing Scarring is often difficult to assess and typically relies on the use of a qualitative scale, such as the Vancouver Scale (Fearmonti, R. et. al., Eplasty 2010, 10, e43-e43). Variation between the scales exists in the scoring and parameters evaluated, though most scales evaluate colour, topography, thickness, and firmness. The use of a primarily qualitative scale for scoring scaring proved to be difficult and ineffective as baseline variations exist between the skin grafts on the mice. Variations in graft pigment, and flakiness/dryness of the skin between the same skin graft source on different mice was observed, as similarly seen in patients (Burnett, L. N. et. al., Burns: journal of the International Society for Burn Injuries 2014, 40 (6), 1097-105). Instead, scarring was assessed by calculating the rete ridge ratio, and the skin graft area before and after wounding to evaluate contraction.

Another cause of scar formation is excessive wound contraction. In healthy healing, some wound contraction is necessary to close the defect and remodel the surrounding tissue. However, excessive contraction can lead to keloids or hypertrophic scarring (Stadelmann, W. K. et. al. *The American Journal of Surgery* 1998, 176 (2, Supplement 1), 26S-38S). During excessive scarring, fibroblasts transform into myofibroblasts, which exert considerable stress on the wound bed, driving wound contraction (Stadelmann, W. K. et. al. *The American Journal of Surgery* 1998, 176 (2, Supplement 1), 26S-38S). There are a number of factors which can lead to myofibroblast activation. While TGF-01 is considered the most prominent stimulator known to induce the fibroblast to myofibroblast transition, tissue stiffness is now seen as a large contributor to fibrosis and myofibroblast activation (Hinz, B. et. al., *Current Rheumatology Reports* 2009, 11 (2), 120). It was previously demonstrated that changes in collagen architecture following grafting can lead to stiffening of the tissue (Rosin, N. L. et. al., *Wound Repair and Regeneration* 2016, 24 (2), 263-274). This increased tissue stiffness can pre-dispose the area to future scaring and myofibroblast activation should a wound occur. As a result, a reduction in skin graft contraction as a result of the Q-Peptide hydrogel treatment may be indicative of a reduction in scarring.

Example 7—Materials and Methods Used in Assessment of Wound Healing in an Equine Limb Model Animals All animal care was approved by the Veterinary Sciences Animal Care Committee at the University of Calgary. A total of ten adult horses (8 geldings and 2 mares) of various breeds (4 quarter horses, 2 pintos, 2 standard breds, 1 Tennessee walking horse) between the ages of 3 and 18 were used in this experiment. Horses were examined prior to study inclusion to ensure that they were free of systemic disease and no pre-existing wounds nor significant lameness were identified on their forelimbs. For the duration of the study period, horses were housed in 60'×40' outdoor pens with access to shelter, mineral licks, and fed a ration of grass hay ad libitum. Following wound creation and excisional biopsy, horses received Phenylbutazone (2.2 mg/kg PO SID for 3 days) for analgesia and were monitored closely for any signs of lameness, swelling, or wound discharge.

Pilot Horse Dermis Wound Creation and Experimental Design

Two horses were selected for a pilot study to ensure bandaging and hydrogel application was feasible before continuing with the full study. The horses were restrained, and sedation provided with detomidine hydrochloride (0.01 mg/kg intravenously) and butorphanol tartrate (0.01 mg/kg intravenously). The dorsolateral aspects of both metacarpi were clipped and aseptically prepared. Regional anesthesia was provided with a dorsal ring block of 2% lidocaine hydrochloride subcutaneously just distal to the level of the carpometacarpal joint. A sterile template was utilized to outline the creation of 4 vertically orientated, 6.25 cm$^2$ full thickness skin wounds (2.5 cm×2.5 cm) 2 cm apart on the dorsolateral as aspects of each forelimb (8 wounds in total). Immediately following wound creation, limbs were bandaged using aseptic technique to facilitate hemostasis. The following day, bandages were removed allowing for treatment application. Due to gross observation of treatment contamination between vertically orientated wounds underneath the bandage, the decision was made to modify the experimental design and these two horses were excluded from further study. Wound care was continued routinely until excisional biopsy sites were healed.

Study Horse Dermis Wound Creation and Experimental Design

Figures 14A, 14B, 14C, 14D, 14E:
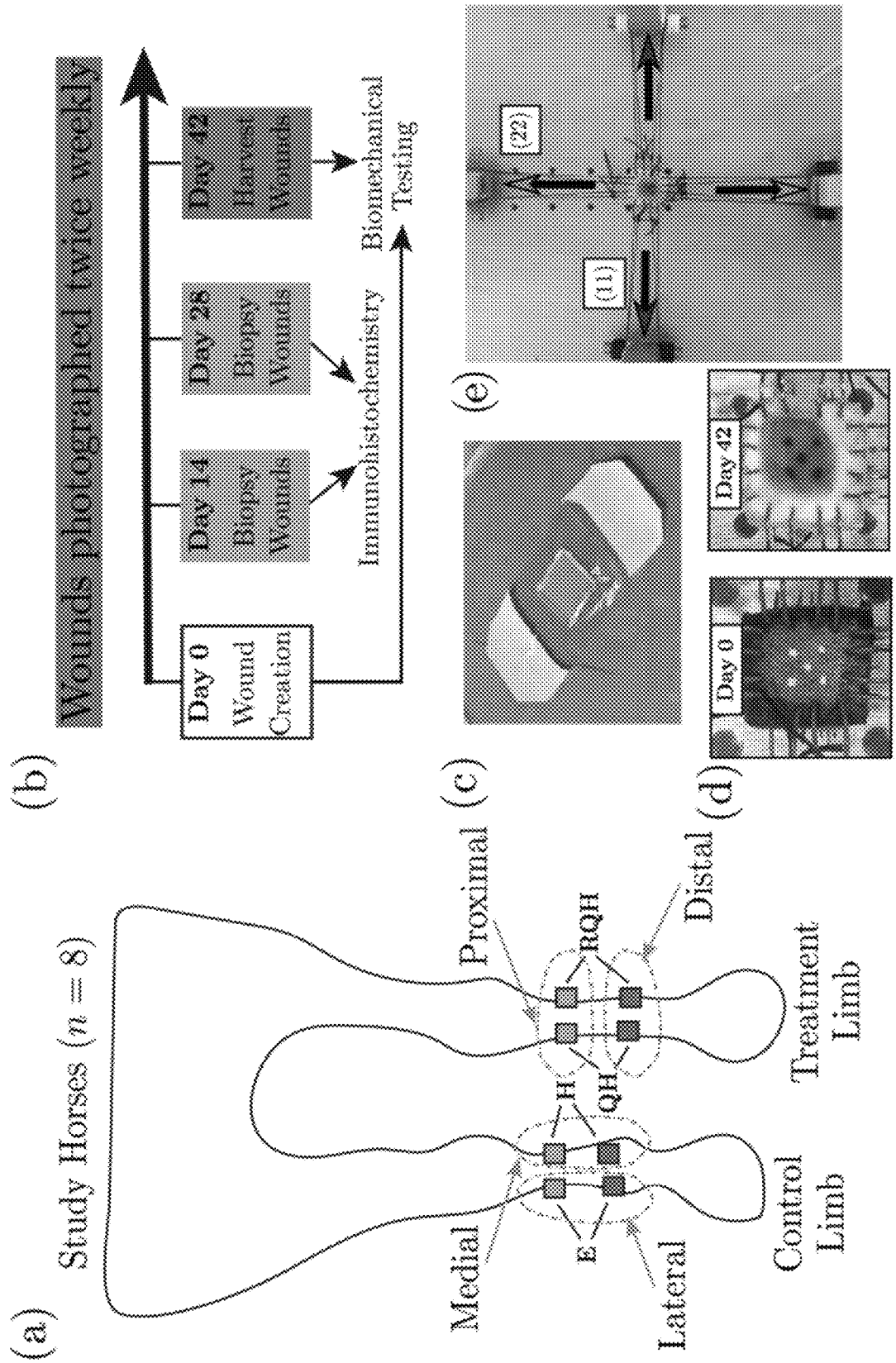
FIGS. 14A-14H show an equine distal limb wound healing model and its biomechanical analysis in an example of the present disclosure.

Eight horses were restrained and sedated as above and both metacarpi were clipped and aseptically prepared. Regional anesthesia was provided as above and the same template used to create 2 vertically orientated, 6.25 cm$^2$ full thickness skin wounds (2.5 cm×2.5 cm) 2 cm apart on the dorsolateral as well as the dorsomedial aspects of each forelimb (8 wounds in total) (FIGS. 14A-B). Proximal wounds (dorsomedial and dorsolateral) were dedicated to observation of gross wound healing until day 42, at which point the entire wounded area was excised under general anesthesia (Xylazine 01. mg/kg IV followed by Ketamine 2.2 mg/kg IV) for biomechanical analysis (FIG. 14B). Wound care was continued routinely until excisional biopsy sites were healed. Distal wounds (dorsomedial and dorsolateral) were utilized for collection of 8 mm wound biopsies for immunohistochemical analysis under standing sedation at days 14 and 28. Biopsies were acquired from opposite sides of the same wound. Following each biopsy collection, these wounds were routinely bandaged and monitored, but no further observation of gross wound healing was made for this study. To ensure no opportunities for contamination of test product (Q-peptide), control wounds (empty and collagen-chitosan hydrogel, E&H) were always done together on a dedicated control limb whereas both the single application and repeated application of Q-peptide (QH & RQH) were performed on the same limb. Treatment sites, however, were randomized to include equal distribution of right and left forelimbs as well as dorsomedial and dorsolateral wound sites (or simply "medial" and "lateral" in what follows). Hydro gels Using 1-ethyl-3-(3-dimethylaminopropyl) carbodiimide (EDC) chemistry, the QHREDGS peptide was conjugated to chitosan (UP-G213, Novamatrix) as previously described (12). Once conjugated and lyophilized, the peptide-chitosan was mixed with collagen at a 1:1 ratio for a final concentration of 2.5 mg/mL. As previously described, a sterile 2.5×2.5 cm polydimethylsiloxane (PDMS) mold was placed on top of a 6×7 cm piece of Tegaderm™ transparent film dressing (3M), and the mold was filled with 1 mL of the peptide hydrogel, or the control hydrogel. The patches were aseptically prepared on day 0 and placed in an incubator at 37° C. On day 1, the patches were removed, the PDMS molds were carefully peeled away, and the resulting hydrogel bandages were placed on the wounds (FIG. 14C). Treatment locations were randomized to include equal distribution of wound locations amongst horses.

Bandaging and Wound Care

On day 1, wound treatment was applied, and the custom hydrogel bandage (or empty wound where applicable) was covered with the circumferential application of Tegaderm™ transparent film dressing (3M) cut to size from a 10 cm wide roll for adhesive reinforcement. Tegaderm™ bandaged limbs were then covered with an 8×10" Telfa™ (Covidien™) nonadhesive pad held in place by a sterile kling. Washable no-bow wraps and standing bandages were then used to cover and protect bandages. Outer bandages were changed every 3-4 days, leaving the Tegaderm™ in place until day 14, at which point these adhesive bandages were removed and wounds bandaged routinely with Telfa™ pads followed by kling and standing wraps. For repeated application of Q-peptide, tegaderm bandages were removed only from the wounds receiving this repeated treatment on day 4 and 7 and replaced with a fresh hydrogel bandage and Tegaderm™ prior to replacing tertiary bandage layers.

Gross Wound Healing Measurement

Photographs were captured of each wound every 3-4 days during bandage changes, ensuring a ruler was positioned in the same plane as the wound for measurement calibration. The gross morphological images were analyzed using ImageJ (Poindexter, N. J. et. al., *Exp Dermatol* 2010, 19 (8), 714-22) to quantify rate of wound healing. The wound area was measured as the area not covered by epithelium from the gross morphological images. The haired wound margin was measured at the boundary between the newly epithelialized skin and uninjured (haired) skin. Excessive granulation tissue (EGT) was scored using a previously described method (Raman, D.; Sobolik-Delmaire, T.; Richmond, A., Chemokines in health and disease. *Exp Cell Res* 2011, 317 (5), 575-89). Briefly, it is based on the summation of 0.5× granulation tissue protuberance (0 none–2 marked), 0.25× granulation tissue color (0 pink–1 yellow/red), and 0.25× granulation topography quality (0 smooth-1 rough). Measurements and scoring were performed by 3 observers blinded to treatment.

Tissue Collection

Excised tissue collected from 8 mm biopsy punches on days 14 and 28 were placed in 4% paraformaldehyde overnight at 4° C. then snap frozen in Optimal Cutting Temperature compound (OCT-VWR) in cryoblocks and kept at −80° C. Tissue blocks were then sectioned at a thickness of 351 µm using a Leica CM1950 cryostat and stored at −80° C. Tissue excised upon completion of the study (day 42) was rinsed in normal saline and individually wrapped flat in aluminum foil before being immediately frozen on dry ice for transport and stored −80° C. before biomechanical testing.

Histological Analysis

Samples were stained using Haematoxylin and Eosin staining. Haematoxylin and Eosin stained slides were digitally captured using an Olympus Virtual Slide System Macro Slide Scanner. On day 28 after wounding, dermal and epidermal thickness was measured in the newly re-epithelialized areas on the wound. The average of three areas, randomly selected to provide an average across the entire area of re-epithelialized wound was performed by 3 observers blinded to treatment. For all quantifications, 4 sections each acquired 280 µm apart were immunostained, representing a 1.12 mm section through the middle of the wound.

Immunohistochemistry

Tissue sections were incubated with primary antibodies in PBS containing 0.05% triton X-100 and 5% goat serum overnight at 4° C. MAC387 (1:200 in PBS) was used to detect granulocytes and macrophages. Von Willebrand Factor (1:200 in PBS) was used to identify blood vessels. Secondary antibodies (1:500 in phosphate buffered saline) were incubated for 1 hour at room temperature. Nuclei were stained with Hoechst (1:200 in PBS) for 10 minutes at room temperature. The slides were then mounted using Permafluor mounting media. Slides were allowed to dry protected from light at room temperature for 2 days and subsequently stored at 4° C. until required. For all quantifications, 4 sections each acquired 280 µm apart were immunostained, representing a 1.12 mm section through the middle of the wound. Images were acquired using a Zeiss Observer microscope and scored or measured by a blinded observer using an automated image analysis software (ImageJ) (Poindexter, N. J. et. al., *Exp Dermatol* 2010, 19 (8), 714-22.). For quantification of vascularization, a modified Chalkley Count was performed (Zaja-Milatovic, S. et. al., *Histol Histopathol* 2008, 23 (11), 1399-407). Briefly, the most vascularized area present within the granulation tissue was identified and an image captured at 20x. ImageJ analysis software was used to overlay a grid pattern atop each image and the number of intersections of vWF+ cells was counted by a blinded observer.

Biomechanical Testing and Data Analysis

Tensile testing was performed on excised intact skin (Day 0) and excised wounds (Day 42) tissue using a 4-motor planar biaxial system (ElectroForce Systems, TA Instruments, Springfield, MO) (FIGS. 14D-14E). Prior to testing, samples were thawed in phosphate buffered saline solution (PBS, pH 7.4) at a room temperature for 90 minutes. Once thawed, samples were oriented to ensure direction (11) and (22) are along and perpendicular to hair growth, respectively; subcutaneous tissue was trimmed from the samples and their thickness was measured at each edge to acquire an average value. Four hooks were attached to each side of the specimen, and the working area was found by measuring the distance between the hooks in both directions for loading adjustment. In the wounded samples, care was taken to ensure hook placement was at the edge of the unwounded skin. Next, using a yellow tissue dye marker on pigmented skin and a violet surgical marker on unpigmented tissue, five dots were drawn on the center of the sample to track deformations during loading by a digital video extensometer (DVE) camera (FIG. 14D). Silk sutures, attached to the hooks, were used to mount the sample to the four motors of the biaxial testing device. Samples were submerged in PBS and kept at 37° C. to maintain hydration for the duration of the test.

The specimens were initially preloaded to 500 mN in both axes to eliminate sagging of the lines and tissue sample. First, displacements were applied simultaneously to each side of the specimen, with 6 mm being a target displacement for an idealized sample with 10 mm×10 mm area in between the hooks (FIG. 14E). Due to the variability in the size of the wounds, the value of the displacement was adjusted by a correction factor based on the undeformed working area, such that 60% deformation was always applied. The samples were conditioned for each protocol by running the test for 10 cycles at a rate of 0.6 mm/s. Data was collected on the last or second to last cycle. Then, the process was repeated for a variety of loading conditions, when the original displacement was applied to two sides along one direction ("1"), and fractions of the original displacement ("0.75, 0.5, 0.2") were applied to the sides of the sample along the orthogonal direction (i.e., protocols 1:0.75, 1:0.5; 1:0.2; 0.2:1; 0.5:1; 0.75:1 with 1:1 being the original protocol called equi-displacement protocol).

Figures 14F, 14G, 14H:
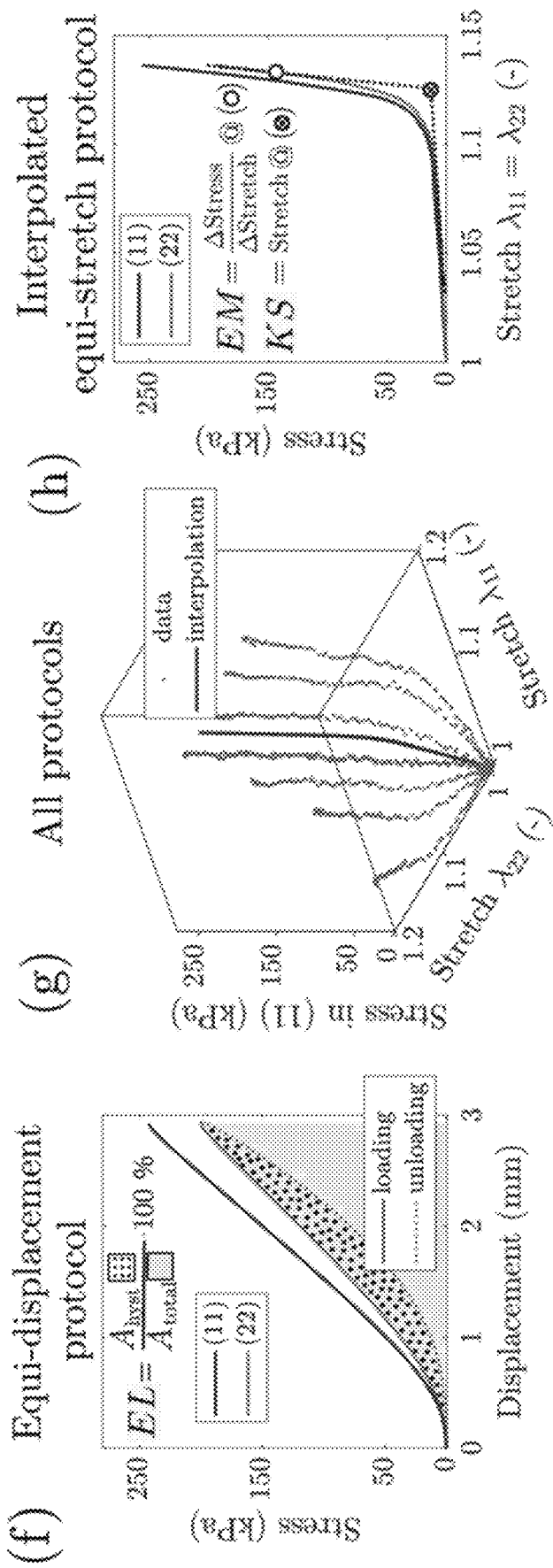

The first Piola-Kirchhoff stresses $P_{11}$ and $P_{22}$ were determined from the forces required to displace the specimen's sides along the two directions divided by the undeformed area (the corresponding side length times thickness). FIG. 14F illustrates the stress plotted against displacement for the equi-displacement protocol in the two directions. Both loading and unloading curves are used to calculate the energy loss (EL) characterizing tissue viscoelasticity and defined as the hysteresis normalized to total the stored strain energy (FIG. 14F). A higher energy loss indicates a more viscous or fluid-like response; a lower energy loss indicates a more elastic or solid-like response. The principal stretches $\lambda_{11}$ and $\lambda_{22}$ were found from the deformations of the center of the specimen computed by the tracked markers (the shear strains were found to be negligible). FIG. 14G illustrates the stress $P_{11}$ plotted against the principal stretches for all seven protocols for one representative sample. An interpolation algorithm applied to all the protocols was used to produce curves with comparable equi-stretch response (i.e. $\lambda_{11}=\lambda_{22}$). A typical interpolated equi-stretch response is shown in FIG. 14G. From here, the knee stretch (KS) indicating the stretch at which the tissue stiffens rapidly corresponding to collagen fibers engagement was determined, and the elastic moduli (EM) identifying the maximum tangential stiffness of the interpolated curves.

To account for individual animal variability (Day 0) and tissue location, the biomechanical parameters (BP) of the healing wounds (MP=EM, EL, KS) was compared as a percent change from that horse's own Day 0 tissue behaviour from the same location (Loc), i.e., BP percent change (%)=$(BP_{Day\ 42,Loc}-BP_{Day\ 0,Loc})/BP_{Day\ 0,Loc}*100\%$.

Second Harmonic Generation Imaging of Collagen

Unstained sections from biopsies taken on day 28 were subjected to second harmonic generation. Samples were imaged using a multiphoton confocal microscope (Zeiss LSM71, Zeiss, Germany) and second harmonic generation (SHG). The microscope was equipped with a Cameleon multiphoton tunable laser (Coherent, USA). SHG was performed to visualize the collagen with the laser set to 800 nm, and a 20× water immersion objective. Z-stacks at 2 μm spacing through the tissue were taken to obtain all focal planes. Images were taken in the upper dermis (the area right below the epidermis) and the lower dermis. SHG images were processed prior to analysis using FIJI (version 2.0.0-rx-68/1.52h). Maximum intensity images of the z-stacks were created, and the autofluorescent background (red) was subtracted from the collagen (white). Analysis of images was performed as described by Liu et al. Briefly, fibers were quantified for directionality (0-180'; relative to the horizontal) and alignment (0=random; 1=aligned) using CurveAlign software (version 4).

Statistical Analysis

All results are presented as mean±SD. Statistical analysis was performed using GraphPad Prism 8. Outcome measures were derived at the level of the wound for each horse. Outliers were identified and removed using the ROUT method. For data having a normal distribution, significance was calculated using either a one-way ANOVA, student's t-test, or survival analysis. To identify significant differences between experimental groups, a Tukey's multiple comparisons test was used. For repeated measures, a two-way ANOVA followed by Sidak's multiple comparisons test was employed. A value of P<0.05 was considered statistically significant.

Example 8—Biomechanics of Dermis Wound Healing in an Equine Limb Model: Effect of Location and Treatment with a Peptide-Modified Collagen-Chitosan Hydrogel The Modified Equine Wound Healing Model A modified equine wound healing model allows investigation of multiple interventions within the same animal, but differential healing must be controlled for across sites.

A pilot study (n=2) using a traditionally reported orientation of vertically stacked wounds revealed considerable treatment contamination between wounds. By day 3, serum and wound exudate was observed to be present across groups, allowing contamination of distal wounds from treatments applied proximally. Due to this observation, results from these 2 horses were excluded from further analyses and a modification of the equine model was developed and explored in this report (n=8). In this modified model, wounds were staggered to allow placement both (dorso) medially and (dorso) laterally on each of the two forelimbs. Vertically orientated wounds were given the same treatment and each treatment was randomized to ensure equal distribution of limb location (medial vs lateral and right vs left forelimb) (FIGS. 14A-14B). One limb was restricted to treatment groups and the other to controls. Using this experimental design, no gross evidence of treatment contamination was observed in any wound. Wounds were well tolerated by horses and no evidence of lameness was observed in any horse over the duration of the study.

Figures 15A, 15B, 15C:
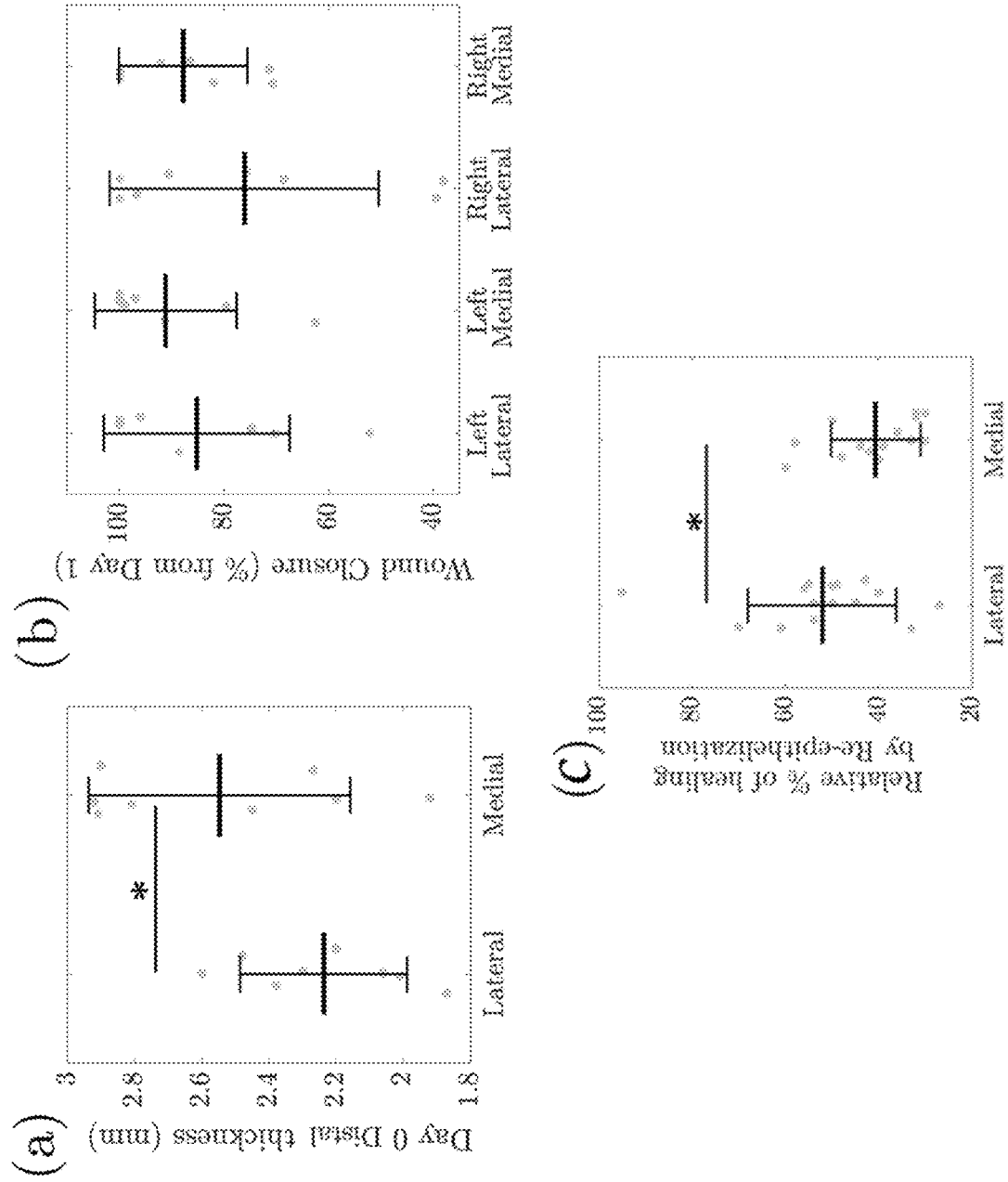
FIGS. 15A-15E show wound location impacts rate of closure and granulation tissue formation in the equine model in an example of the present disclosure.
Figure 15D:
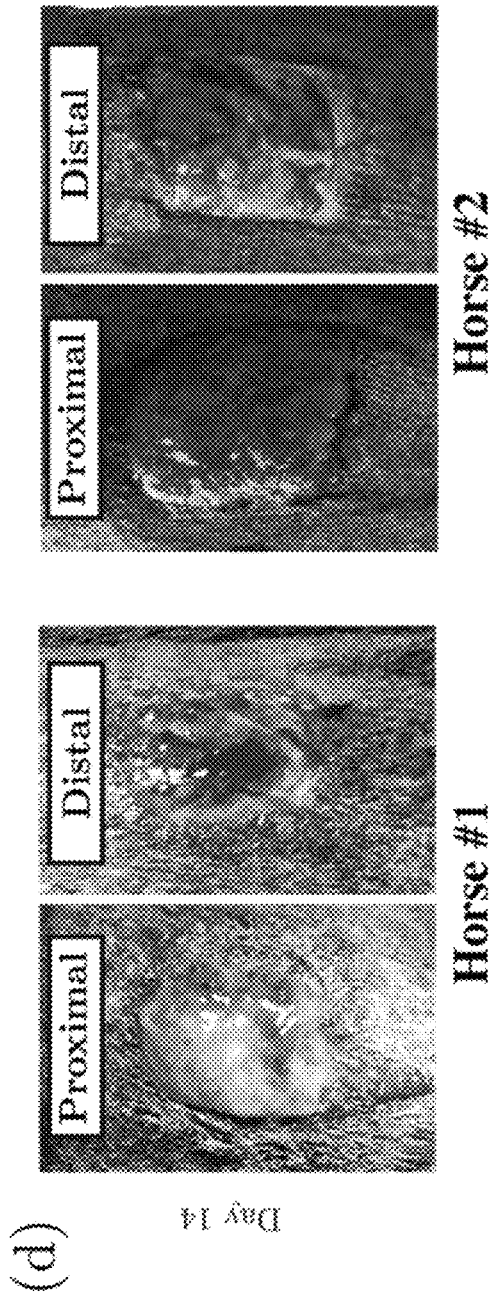
Figure 15E:
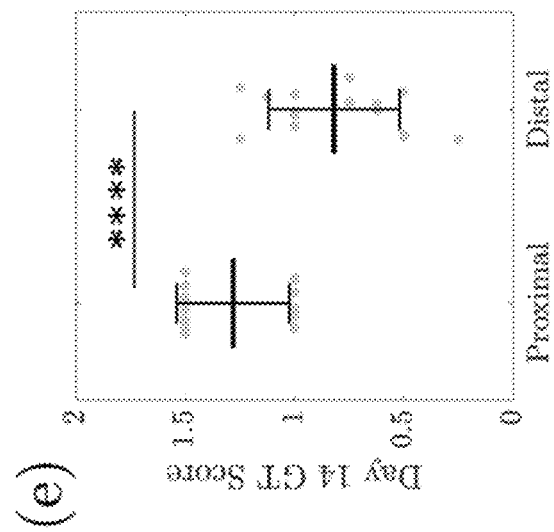

Significant differences were noted in the thickness of unwounded skin at each location, with medial skin found to be thicker than lateral. (FIG. 15A). By the conclusion of the study (day 42), only 40.6% of wounds were observed to have completely closed. Wound healing kinetics were highly variable between horses, however a trend (p=0.08) for faster wound closure was identified for medial wounds compared with lateral (FIG. 15B). No difference was observed between right vs left limbs when controlling for medial or lateral wound location. Medial wounds experienced a significantly greater proportion of wound closure through contraction compared to lateral wounds (FIG. 15C). Pink, healthy granulation tissue (GT) was observed to fill the wound bed by day 4, becoming exuberant and irregular in some wounds by day 8 (FIG. 15D). Using a scoring system previously described for GT (Wise, L. M. et. al., PLoS One 2018, 13 (5), e0197223) health, scores were found to be significantly higher (worse) for proximal wounds compared with distal wounds on day 14 (FIGS. 15D-15E). As biopsies were collected from proximal wounds at day 14 and 28, no further comparisons were made for healing rate or quality between these two locations.

Biaxial tensile testing and analysis of unwounded and wounded skin produced biomechanical data lacking clear directional preference.

Figures 16A, 16B, 16C:
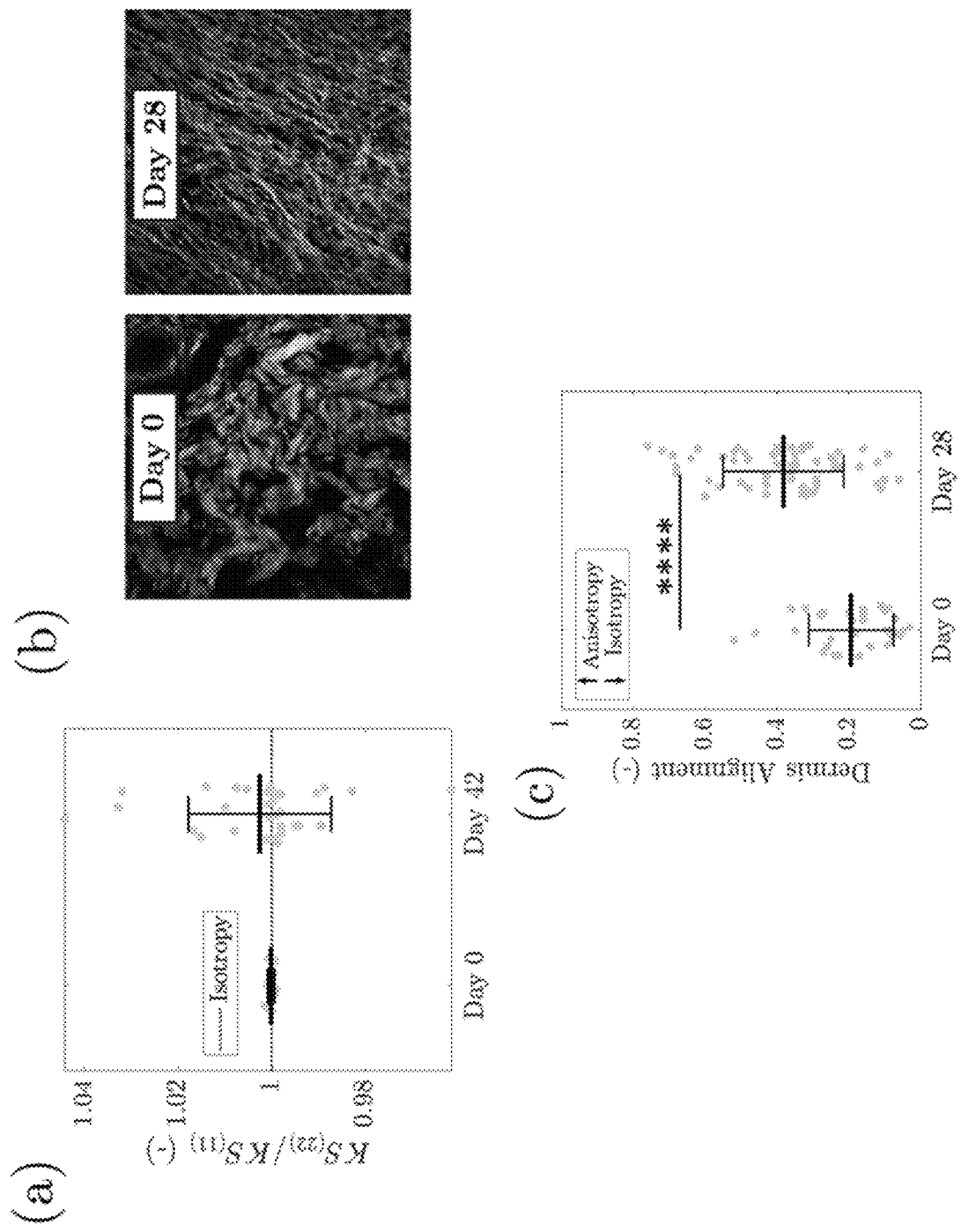

The tissue samples collected for the biomechanical assessment were 2.8+/−0.6 mm thick and the working area between the hooks was 10+/−1.7 mm×8.6+/−1.5 mm. Stress-stretch curves exhibited nonlinear response typical for skin tissue with a prolonged toe and rapid stiffening. By using multiple loading protocols and the interpolation algorithm, the mechanical response of the tissue was characterized at equivalent deformation states (the state of equal stretches in direction (11) and (22)) across all samples; and the biomechanical results in the following have to be interpreted with this factor in mind. Ratios of the biomechanical parameters (BP=EM, EL, KS) in direction (11) to their analogues in direction (22), i.e., $BP_{11}/BP_{22}$, did not reveal consistent preferential direction (KS in FIG. 16A) for uninjured or wounded tissue. However, a more anisotropic response (deviation from "1") was noted for healing (day 42) specimens, which is especially evident in FIG. 16A for KS, where the uninjured controls were remarkably isotropic. The increased anisotropy in healing wounds is corroborated by increased alignment in their collagen fibers observed using second harmonic generation (SHG) imaging of collagen fibers (FIGS. 16B-16C). The anisotropy was deemed not enough to warrant separate analysis between directions (11) and (22), thus, for further analyses, they were combined. Notably, differences in fiber alignment between controls and wounded specimens were not observed in the proximal dermis adjacent to the epidermal basement membrane.

Tissue location and stage of wound healing impact the biomechanical properties of equine skin.

Figures 16D, 16E, 16F:
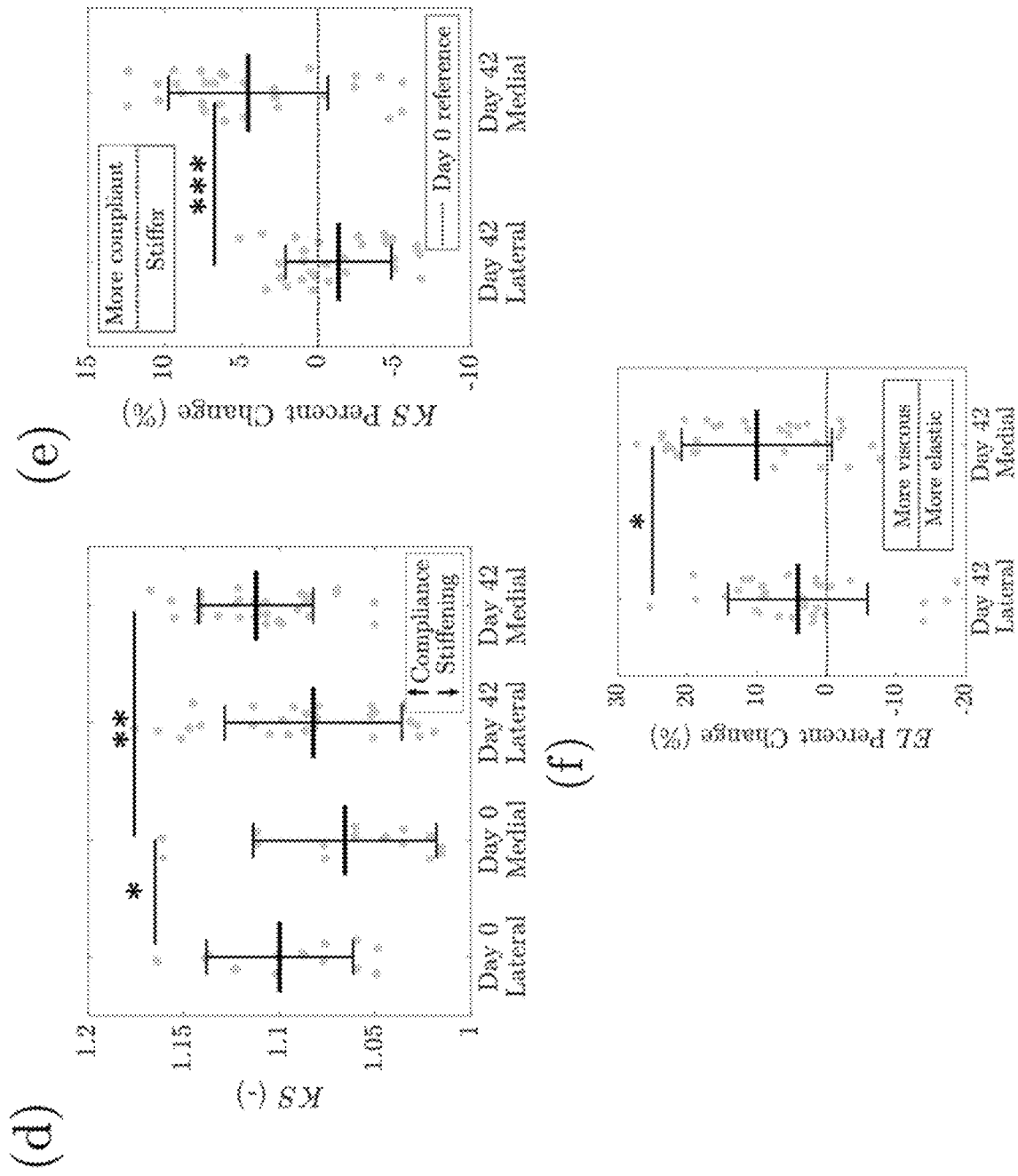

In both the wounded and unwounded specimens, location on the limb (lateral versus medial), did not appear to influence the stiffness (EM) and viscoelasticity (EL) of tissues. However, location was found to significantly affect values of knee stretch (KS) (FIG. 16D) where medial day 0 specimens have earlier collagen engagement as evidenced by a lower KS. In day 42 healing specimens, this relationship appears to switch with the lateral specimens engaging collagen fibers sooner. To explore this feature of wound healing further, the percent change from each horse's own day 0 was looked at and identified a significant increase in KS (FIG. 16E) and EL (FIG. 16F) in medial wounds, but no difference between the two locations for EM during healing.

In addition to an increased anisotropy reported earlier (FIG. 16A), wounds at day 42 of healing, in general, were found to be more compliant (FIGS. 16G-16H) and more viscoelastic (FIG. 16I) than the uninjured control. This coincides with differences in collagen fiber architecture of the dermis, where the healing (Day 28) samples had markedly thinner collagen fibers compared with uninjured (Day 0) control (FIGS. 16B-16C), although it is worth noting no SHG data was collected for Day 42 wound samples. Further, healing wounds with complete restoration of the epithelium ("closed") exhibited the highest compliance compared to open wounds as evidenced by a significantly lower tangential stiffness (EM, FIG. 16G) as well as a more pronounced viscoelastic response (FIG. 16I). The equine distal limb model of chronic wound healing is well established (Theoret, C. L. et. al., Vet Surg 2001, 30 (3), 269-77) and has consistently proven to recapitulate conditions of aberrant wound healing such as the deficient wound closure and fibroproliferative disorders commonly observed in man (Theoret, C. L. et. al., Wound repair and regeneration: official publication of the Wound Healing Society [and] the European Tissue Repair Society 2013, 2/(3), 365-71, Theoret et. al., Veterinary surgery: VS 2013, 42 (7), 783-9). In the pilot study, the aim was to compare healing between 4 different treatment groups using 2 replicate wounds per group to allow detailed temporal investigation. To accomplish this aim, 4 vertically orientated wounds were first created on each forelimb and designated one forelimb for gross observation and one for early wound biopsy collection. In this approach, mixing of wound fluid from different treatment groups underneath the bandage was observed. Armed with this information, the aim was to further distance treatment groups, thus preventing treatment contamination. Previous studies have accomplished this by creating wounds on both the fore and hind limbs (Harmon, C. C. G. et. al., Am J Vet Res 2017, 78 (5), 638-646, Winter, R. L. et. al., BMC Vet Res 2020, 16 (1), 43) as well as the medial and lateral aspects (Lawless et. al., PLoS One 2020, 15 (6), e0235006). However, differences in healing rates previously identified between forelimbs and hindlimbs (Winter, R. L. et. al., BMC Vet Res 2020, 16 (1), 43, Dart, A. J. et. al., Vet Surg 2002, 31 (4), 314-9), as well as additional handling challenges posed by working on hindlimbs directed the present motivation to modify the orientation of wounds on the forelimbs alone. Another method previously utilized by researchers to increase the number of wounds per limb for testing includes the creation of smaller wounds such as 5 mm×2 cm (Theoret, C. L.; Barber, S. M.; Moyana, T. N.; Gordon, J. R., Expression of transforming growth factor beta (1), beta (3), and basic fibroblast growth factor in full-thickness skin wounds of equine limbs and thorax. Vet Surg 2001, 30 (3), 269-77), 1.5×2 cm (Bischofberger et. al., Aust Vet J 2015, 93 (10), 361-6) or 2×2 cm (Bodaan, C. J. et. al., Wound Repair Regen 2016, 24 (6), 966-980, Bischofberger et. al., Vet Surg 2013, 42 (2), 154-60). Certainly, the healing kinetics of various sized wounds will differ, thus the use of a wide range of wound sizes between studies unfortunately prevents critical comparisons between and across research throughout the field. Consequently, the most widely reported size of wounds (2.5×2.5 cm) was selected for us. Then, to prevent treatment mixing, the placement was staggered such that wounds were made on both the dorsomedial and dorsolateral aspect of the forelimbs (Bischofberger et. al., Vet Surg 2013, 42 (2), 154-60). The two vertically orientated wounds were then treated with the same test product, control products were restricted to the same limb, and treatment was randomized to ensure equal distribution. Controlling for wound location indeed allowed for the exploration of the differences in healing on medial vs lateral as well as proximal vs distal sites in parallel.

In the modified model, 40.6% of wounds were observed to have completely closed by the study end point (42 days). When considering only control wounds, only 3/8 (37.5%) were closed in 42 days. Previous publications report a wide range of closure times required for this size of wound, some of which are over 100 days (Fowler et. al., Vet Surg 2019, 48 (8), 1416-1428, Tsang, A. S. et. al., Aust Vet J 2017, 95 (9), 333-337, Berry, D. B., 2nd; Sullins, K. E., Effects of topical application of antimicrobials and bandaging on healing and granulation tissue formation in wounds of the distal aspect of the limbs in horses. Am J Vet Res 2003, 64 (1), 88-92). Certainly, this effect may relate to differences in experimental design such as wound location and EGT prevention and management. As a result of this variability, many studies, including the current study, employ a 42 day endpoint rather than following all wounds to close (Textor, J. A. et. al., Stem Cells Transl Med 2018, 7 (1), 98-108, McIver, V. C. et. al., Aust Vet J 2020, 98 (6), 250-255). Depending on the aims of the study, researchers have also elected to leave wounds unbandaged for all or part (Bischofberger et. al., Aust Vet J 2015, 93 (10), 361-6, Tsang et. al, Aust Vet J 2017, 95 (9), 333-337, Textor et. al., Stem Cells Transl Med 2018, 7 (1), 98-108, McIver, V. C et. al., Aust Vet J 2020, 98 (6), 250-255) of the study, surgically debride EGT either only when/if it occurs or in all wounds (Fowler, A. W. et, al., Vet Surg 2019, 48 (8), 1416-1428), or bandage for the duration of healing and leave EGT untreated (Wise, L. M. et. al., PLoS One 2018, 13 (5), e0197223). In this study, where the latter protocol was followed, only 5/8 control (no treatment)

wounds were observed to have clinical evidence of EGT on day 14. At this timepoint, significantly worse EGT was observed in proximal wounds compared with distal. To the authors knowledge, no previous comparisons of EGT have been made between vertically orientated wounds on the same limb. Interestingly, even without treatment, EGT was observed to resolve in all but 1 of these wounds by day 42 indicating a natural ability to eventually overcome this fibroplastic response in many wounds.

Though wound closure is vital for restoration of the epithelial barrier, biomechanical function of the healed dermal tissue is an important feature of skin health and function. Yet, its investigation is often lacking from experimental wound healing studies. Here, biaxial mechanical ex-vivo testing was employed to investigate the biomechanical function of healing skin. This method is unique in that it: 1) mimics in-vivo deformation experienced by skin in movement and 2) captures direction-dependent behavior of skin and the interaction of collagen fibers in two orthogonal directions (Xu, F. et. al., 2011, Corr, D. T., Hart, D. A. et. al., *Adv Wound Care* (New Rochelle), 2013; Vol. 2, pp 37-43). This is the first use of biaxial mechanical testing on equine skin. Hence, the unique properties of the model (effects of location and directions) were first defined as well as ways to assess healing quality (with respect to the wound closure and as compared to controls).

It is well-established that the biomechanical properties of full-thickness skin are mainly due to the dermis as the epidermis contributes little to the skin's resistance to stretch and its viscoelastic properties (Xu, F.; Lu, T. J., *Introduction to skin biothermomechanics and thermal pain*. Springer-Verlag Berlin Heidelberg: 2011). Thus, functional testing in early wound healing (day 42) was elected to be conducted, despite differences observed in the amount of re-epithelialization present. Importantly, biaxial tensile testing of both unwounded and wounded skin from the distal equine limb revealed a lack of clear directional preference with respect to the chosen directions (along and perpendicular to hair growth); a finding corroborated by previous studies in other species (Corr, D. T. et. al., *Adv Wound Care* (New Rochelle), 2013; Vol. 2, pp 37-43). Interestingly, though, it was observed in the study that an increase in collagen fiber alignment during wound healing, through both the SHG images (although at earlier timepoint, i.e. Day 28) and an increased anisotropy in the biomechanical function. Further, skin from different limb locations exhibits different physical and mechanical properties that may result from the functional requirements and environmental influences specific to different locations. It was demonstrated that un-wounded skin from medial locations was thicker and less compliant than skin from lateral locations, which may reflect physical and functional adaptations. In vivo, skin in the lateral location experiences more movement and overlies soft tissue structures such as the common and lateral digital extensor tendons which could help to absorb traumatic forces. Medially, however, the skin is lying directly over bone, and would seem to be at greater risk for traumatic injury as there is little tissue underneath to absorb impact forces. Therefore, it follows that medial skin would be thicker and more stiff (less compliant) (Williams, D. F et. al., *Journal of Biomechanics* 10 (10), 633-642). Lastly, discrete differences was identified during healing of wounds in differing locations where medial wounds demonstrate a tendency to close faster and with a greater contribution of wound contraction. Biomechanically, medial wounds also underwent more severe functional changes in dermis, exhibiting increased biomechanical compliance and viscosity during healing. These findings suggest that future studies should consider the potential for major differences in healing characteristics between minorly different locations on the equine distal limb.

To account for the observed differences between medial and lateral samples, wounds were compared against unwounded tissue from the same animal and same location and found to be more compliant overall. Moreover, closed wounds exhibited the most compliance. By the selected time point (Day 42), while a number of samples had closed, the underlying dermal tissue was still undergoing remodeling. The increased compliance of the wounds is a positive effect was postulated, as it suggests decreased early tissue fibrosis (Bowden et. al., *Biomech Model Mechanobiol* 2016, 15 (3), 663-81). Indeed, though the epidermis itself contributes very little to the biomechanical function of skin, the physiologic closure of the wound likely leads to improved remodeling of tissue and decreased fibrosis or scarring, as is frequently described in models of skin regeneration which consistently undergo rapid re-epithelialization (Erickson, J. R. et. al., *Dev Biol* 2018, 433 (2), 144-154). In addition to quantifying tissue compliance, the energy loss of wounded tissue was investigated as a measure of its viscoelasticity. Viscoelasticity is likely to be related to the cross-linking of the collagen fibers in tissue (Silver, F. et. al., Advanced Tissue Engineering Regenerative Medicine Open Access 2017, 2 (1), 114-119). As the fiber network becomes more cross-linked, the viscoelasticity decreases indicating an increase in the elasticity. In healing wounds, newly formed collagen fibers are not as cross-linked compared to the control, which is evidenced by an increased viscoelasticity (more viscous response), and, therefore reduced ability of wounded tissue to bounce back after the application of a load. In theory, a decrease of viscoelasticity in wounds, i.e. cross-linking, promotes wound closure by providing pathways to transmission of compressive forces and facilitates return to the "natural state" (Sardari et. al., *Comparative Clinical Pathology* 2009, 18 (3), 239-247). And although it should be considered as a positive characteristic of healing, excessive cross-linking of fibers during early wound healing can promote premature wounds stiffening and potentially delay closing, which is a pathological deviation from a successful healing path (Brauer, E. et. al., *Adv Sci (Weinh)* 2019, 6 (9), 1801780). Perhaps, for this reason, open wounds displayed a trend towards decreased viscoelasticity, although not a significant one. Future work may shed more light on how viscoelasticity changes at different stages of healing. In particular, more accurate measures of viscoelasticity are needed as well as more appropriate viscoelasticity-oriented biomechanical testing (or protocols) for a more thorough analysis. Still, it was hypothesized that while a moderate decrease in viscoelasticity in healing wounds is favorable, a significant reduction in viscoelasticity (high elasticity) could indicate excessive crosslinking resulting in a much stiffer tissue and less favorable remodeling.

During early wound healing, increased compliance and a trend towards decreased viscoelasticity was proposed to be indicative of favorable dermal remodeling. Future studies should consider a later timepoint for biomechanical testing to account for a greater contribution of the remodeling stage of wound healing.

Figure 17A:
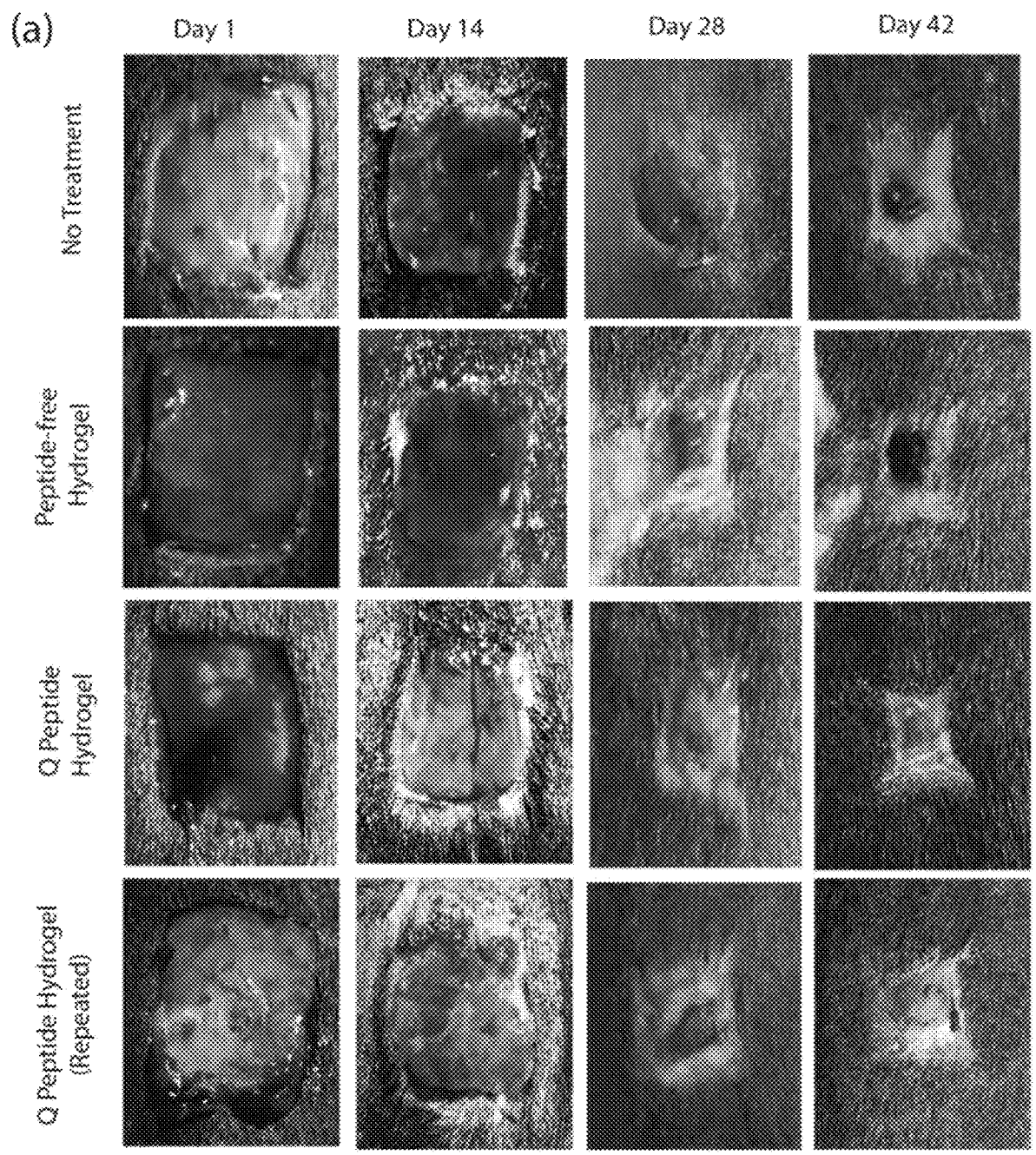
FIGS. 17A-17E show a single treatment with a peptide-modified hydrogel improves wound healing rate in an example of the present disclosure.
Figures 17B, 17C, 17D, 17E:
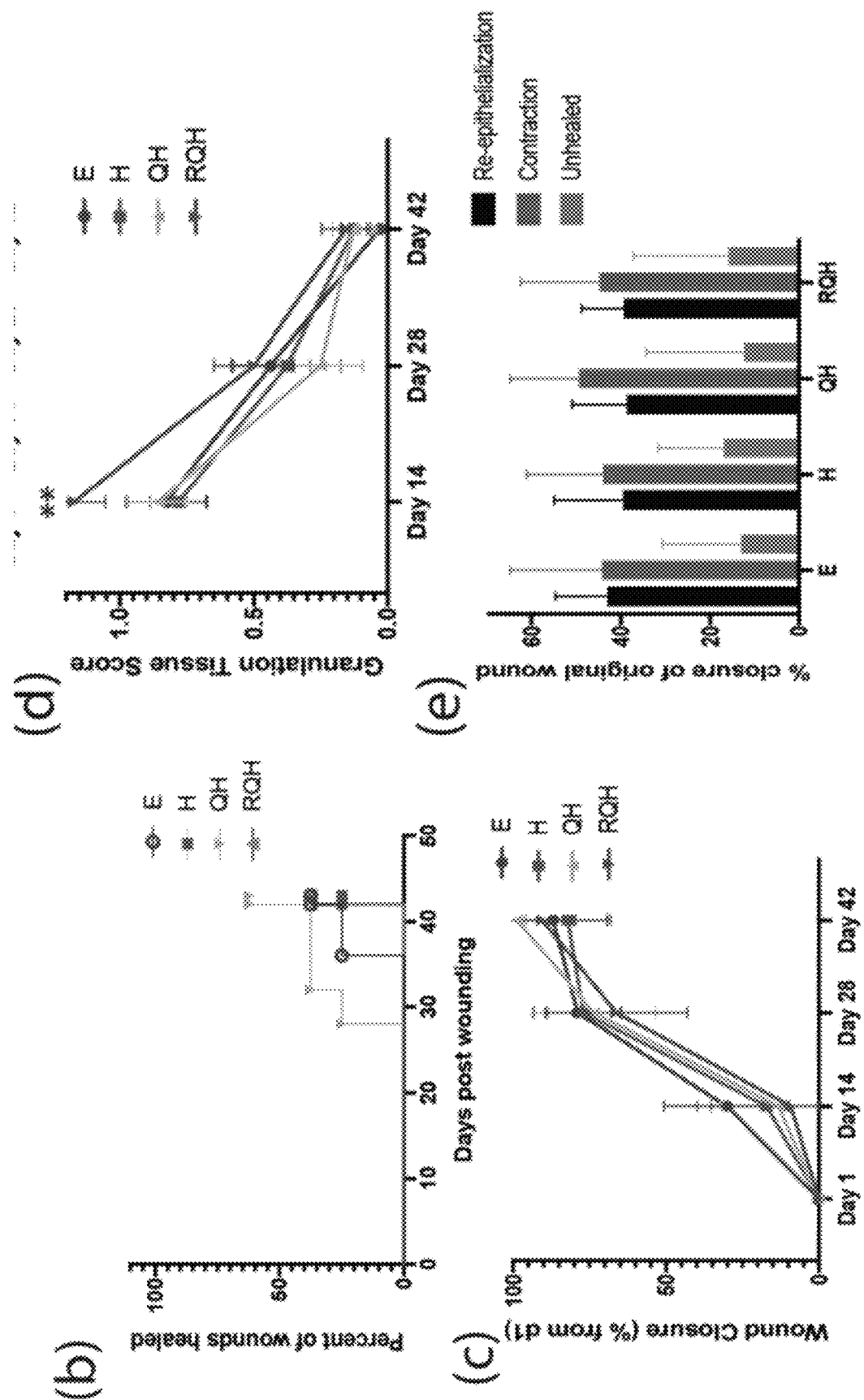

Example 9—Investigating the Effect of a QHREDGS (SEQ ID NO: 1)-Conjugated Collagen-Chitosan Hydrogel on Dermis Wound Healing in the Modified Equine Model A single initial treatment with peptide-modified hydrogels resulted in a greater number of wounds healed within 42 days as compared to controls Prefabricated hydrogels (FIG. 14A) adhered well, and with the aid of a circumferential layer of Tegaderm film, persisted in place for 14 days where indicated. In some cases, the 2.5×2.5 cm gel was observed to have become slightly dislodged such that it was not always in constant contact with the entire wound perimeter. Upon completion of the study (day 42), 62.5% of Q-peptide hydrogel treated wounds were healed compared with 37.5% of empty and 33.3% of peptide-free hydrogel treated wounds (FIG. 17A and FIG. 17B). When considering healing kinetics across the duration of the study, rate of closure did not differ significantly between treatment groups across the study duration (FIG. 17C). On average, wounds reduced to 87+/−17.7% (empty; E), 82.1+/−14% (peptide-free hydrogel; H), 98.7+/−3.1% (Q-peptide hydrogel; QH), and 90.5+/−10.9% (repeated Q-peptide hydrogel; RQH) of their original wound size by day 42. On day 14, 84% (27/32) of wounds were observed to have clinical evidence of exuberant granulation tissue (EGT). By day 28, only 25% of single Q-peptide treated wounds had clinical EGT compared with 62.5% of repeated Q-peptide, 50% of peptide-free hydrogel, and 37.5% of no treatment control wounds. Despite the present study design not including debridement of EGT, nearly all wounds had resolved EGT by day 42. Specifically, only 12.5% of single Q-peptide, peptide-free hydrogel, and no treatment control wounds and 37.5% of repeated Q-peptide treated wounds contained EGT at this timepoint. Granulation tissue score, a measure of quality, was significantly increased (worsened) in the repeated Q-peptide group at day 14 ($p=0.006$) but no differences were observed at later timepoints (FIG. 17D). All wounds healed by a significantly greater contribution of re-epithelialization than contraction ($p=0.0015$). However, no significant difference was observed between percent of wound closure by contraction (E 43.3+/−7.2%, H 42.6+/−6.6%, QH 49.2+/−5.6%, RQH 35.2+/−15%) and re-epithelialization (E 56+/−4.3%, H 60.9+/−5.3%, QH 61.4+/−4.4% RQH 60.6+/−3.2%) between treatment groups (FIG. 17E).

No negative effects of Q-peptide treatment on immune infiltration, vascularization, or scar formation within wounds.

Figure 18A:
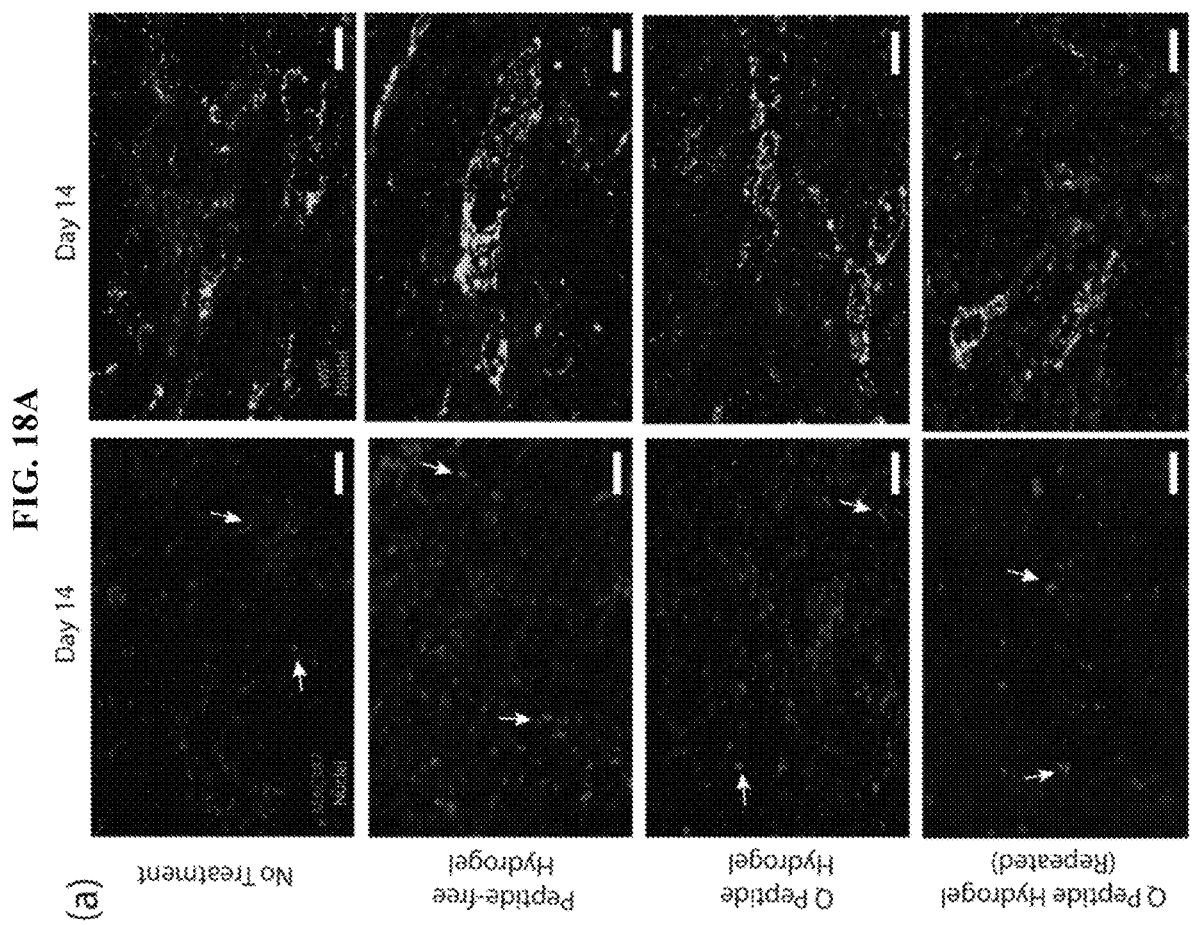
FIGS. 18A-18C show that treatment with peptide-modified hydrogels shows no negative effects on inflammatory response and re-vascularization during wound healing in an example of the present disclosure.
Figures 18B, 18C:
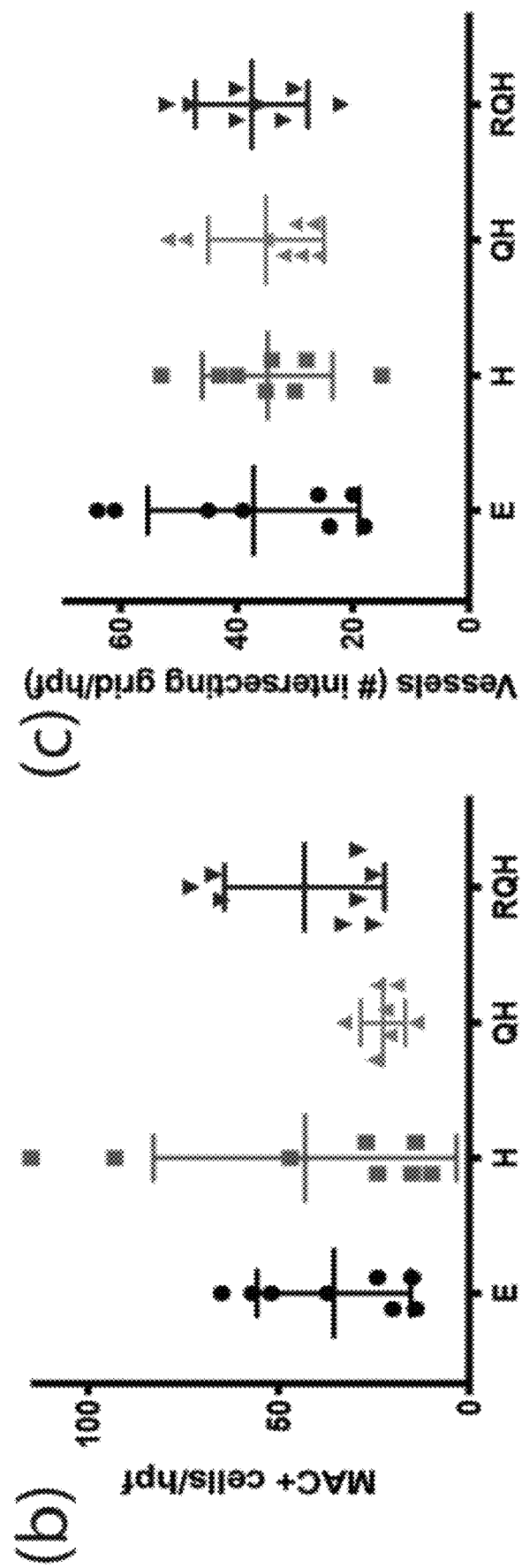

To investigate the effect of treatment on immune cell infiltration and neovascularization, day 14 biopsies were immunostained for MAC387 (highlighting granulocytes and macrophages) and vonWillebrand Factor (vWF) to localize endothelial cells present within blood vessels (FIG. 18A). At this timepoint, many MAC387+ immune cells were observed to persist within all wounds, but no significant differences were identified between treatment groups (FIG. 18B) (E 35.5+/−20.22%, H 43.1+/−39.7%, QH 22.57+/−5.9% RQH 43.3+/−21% cells per high powered field). Likewise, no significant differences were observed in the quantification of neovascularization within the granulation tissue at day 14 (FIG. 18C) (E 37.1+/−18.2%, H 34.8+/−11.3%, QH 35+/−10% RQH 37.5+/−9.7%).

Figure 19A:
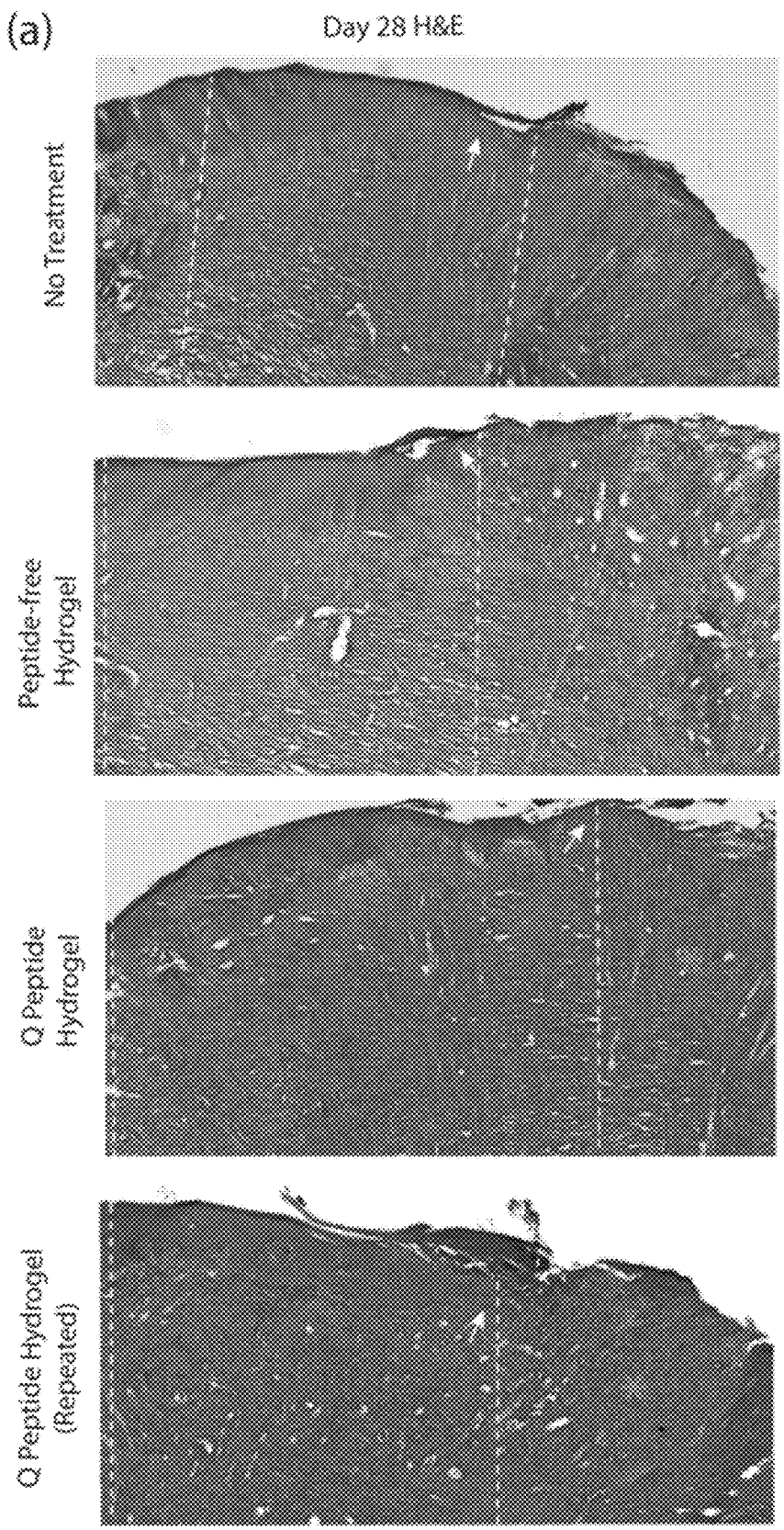
FIGS. 19A-19D show that treatment with peptide-modified hydrogels does not alter the thickness of healing scar during early healing (day 28) in an example of the present disclosure.
Figures 19B, 19C, 19D:
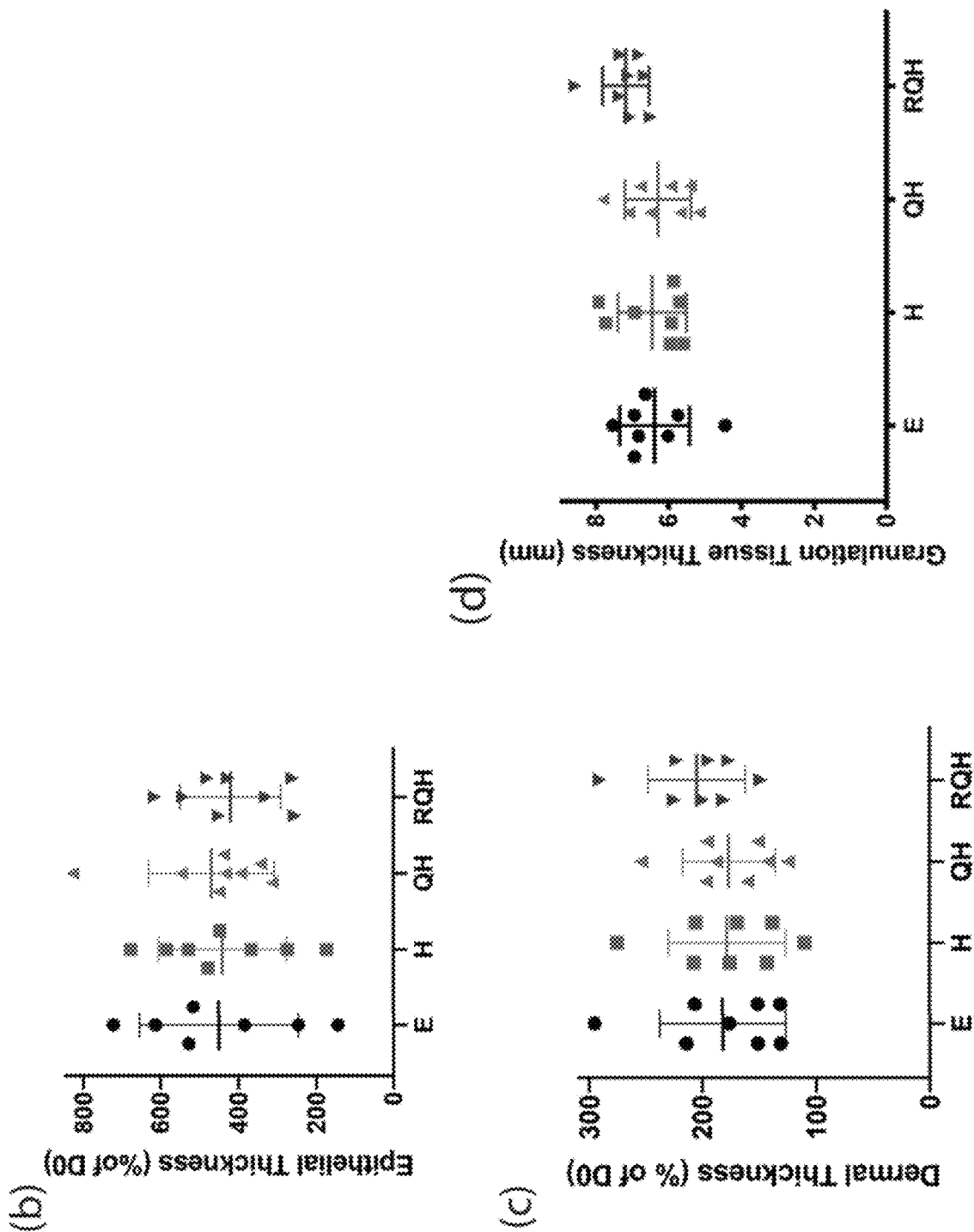

Histologic investigation of the architecture of healing wounds at day 28 (FIG. 19A) revealed no significant differences in thickness of healing tissue between groups. Likewise, no significant differences were observed in granulation tissue thickness (E 6.4+/−0.96 mm, H 6.5+/−0.94 mm, QH 6.3+/−0.91 mm, RQH 7.2+/−0.64 mm) across treatment groups (FIG. 18D). Interestingly, both the epidermis (FIG. 19B) (E 451+/−204%, H 441+/−165%, QH 468+/−162% RQH 420+/−130%) and dermis (FIG. 19C) (E 182+/−55%, H 178+/−51%, QH 177+/−41% RQH 205+/−43%) were markedly thickened during this phase of wound healing across groups relative to the same measurement taken at day 0.

Q-peptide Hydrogel modulates the fibrotic response in the dermis during early wound healing.

Figures 20A, 20B, 20C:
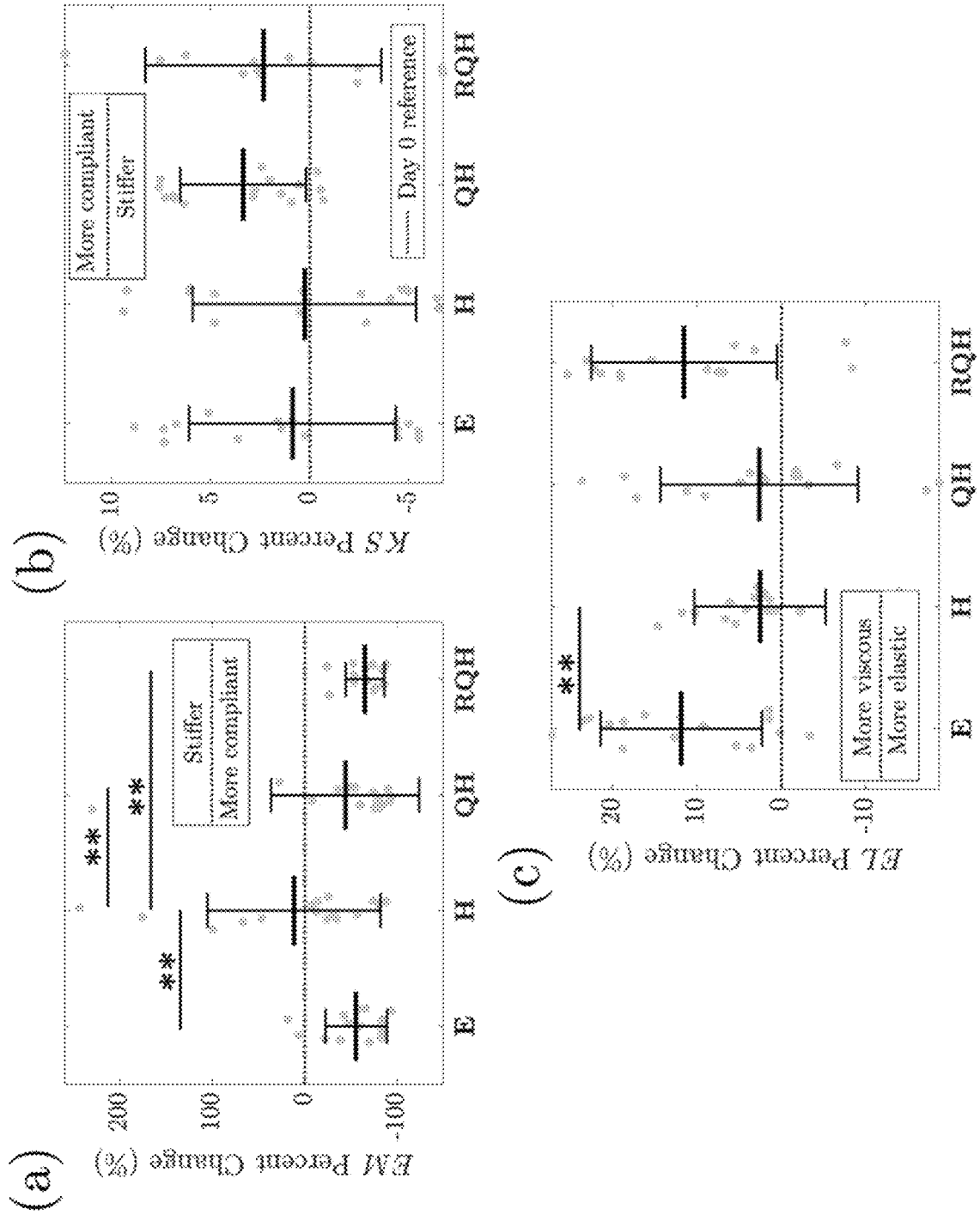
FIGS. 20A-20C show the effect of treatment on the biomechanical response during early wound healing in an example of the present disclosure.

Treatment of wounds with the peptide-free hydrogel (H) increases stiffness (EM) of wound samples compared to wounds with no treatment (E); whereas addition of the Q-peptide hydrogel (QH and RQH) rescued this effect (FIG. 20A). The addition of the Q-peptide (QH and RQH) also increases the knee stretch KS of the wounded tissue compared to E and H, although not significantly (FIG. 20B). Lower EM and higher KS indicate the overall greater compliance in Q-peptide treated wounds (QH and RQH), which is consistent with decreased fibrosis (or scarring) in the wounds. The viscoelasticity of the wounds that received single application of Q-peptide hydrogel (QH) and the peptide-free hydrogel (H) were also observed to most closely reflect that of uninjured skin (FIG. 20C). The Q-peptide hydrogel has been developed and validated as two available forms: an injectable gel and a pre-gelled patch (Mandla et. al., 2019; Vol. 5, pp 4542-4550). The later was selected here for ease of use in a standing animal. The biomimetic peptide sequence, QHRDEGS (SEQ ID NO: 1), is also conjugated to the chitosan component of hydrogel itself (Xiao, Y. et. al., *Proc Natl Acad Sci USA* 2016, 113 (40), E5792-e5801) such that its effects are restricted to cells in direct contact with the dressing and not systemic absorption into the patient. This feature ensures the safety of its use as a medical device. In the current study, granulation tissue score was significantly worse in the repeated Q-peptide group at day 14, but this effect was mitigated at later timepoints Likely, a key cause of this finding was the need for continued removal of the semi-occlusive bandage (Tegaderm) to allow for re-application of the Q-peptide hydrogel, which only occurred in this group (RQH). While application of a bandage does indeed lead to production of EGT in the horse, the use of occlusive and semi-occlusive dressings also allows for the accumulation of exudate in the wound bed which may counter the hypertrophic response through autolytic debridement (Pain, R. et. al., *Vet Rec* 2006, 159 (21), 712-7). Ultimately, to confirm this, an additional control would have been required where the occlusive bandage was changed at the same rate, but no treatment applied.

One key feature of the Q-peptide gel is its direct promotion of the attachment, migration, and survival of keratinocytes leading to more rapid closure of wounds (Xiao, Y. et. al., *Proc Natl Acad Sci USA* 2016, 113 (40), E5792-e5801). In the horse, re-epithelialization from the wound edge is a slow process on the distal limb. Previously reported as macroscopically present at 2 weeks after wounding and progressing no faster than 1 mm in 10 days, identifying methods to improve this re-epithelization rate would be key to improving wound repair in this location (Wilmink, J. M. et. al., *Vet Clin North Am Equine Pract* 2005, 21 (1), 15-32). Indeed, a single application of the Q-peptide hydrogel resulted in 62.5% (5/8) of wounds being classified as healed at the endpoint of the study. This observation is powerful as all other groups were observed to have no greater than 37.5% (3/8) of wounds healed by day 42. This difference was less apparent through direct measurement of wound closure kinetics, likely due to individual horse variation, wound healing location, and inter-observer variability in accuracy of measurements. Overall, as previously described, wounds on the distal limb healed by a significantly greater contribution from re-epithelialization than contraction.

While not significant, wounds treated by Q-peptide displayed 61.4+/−4.4% of closure through re-epithelialization whereas untreated wounds re-epithelialized 56+/−4.3%. Several limitations of the current study design may have impeded the ability to observe significant effects on this rate of re-epithelialization directly. One key limitation was that exuberant granulation tissue was also observed in several wounds secondary to prolonged bandaging. Certainly, this provides a physical barrier to re-epithelialization and may have confounded results. Further research should assess if excision of EGT and removal of the bandages after 14 days would further improve the results observed following treatment with the Q-peptide hydrogel. Another possible limitation may have resulted from poor contact between the gel and the wound edge, as the material was observed to have slipped in some of the wounds. Previous research has demonstrated no efficacy when the Q-peptide is soluble, suggesting conjugation of the Q-peptide on the hydrogel is necessary to support a mechanical mode of action (Xiao, Y. et. al., *PNAS* 2016, 113, E5792-E5801, Reis, L. A. et. al., *Circ Heart Fail* 2015, 8 (2), 333-41). In particular, (31 integrins have been implicated in promoting cell attachment on the Q-peptide hydrogel. As a result, poor contact between the migratory edge of the wound and the carrier may impact keratinocyte re-epithelialization by preventing integrin binding (Xiao, Y. et. al., *PNAS* 2016, 113, E5792-E5801).

The Q-peptide hydrogel has also been previously reported to alter the dynamics of the inflammatory response during wound healing. In the horse, a delayed and weak onset of the inflammatory phase followed by a prolonged period of chronic, low grade inflammation has been demonstrated to play a key role in the poor healing response observed in the distal limb (Wilmink, J. M. et. al., *Vet Clin North Am Equine Pract* 2005, 21 (1), 15-32). While no significant differences were observed in total granulocyte and macrophage numbers at day 14, treatment with Q-peptide resulted in a more uniform inflammatory response between samples. However, detailed investigation that includes both early and more persistent immune cell dynamics following treatment with Q-peptide is imperative in future work. Likewise, augmentation of the cytokine profile of cells involved in wound healing has also been demonstrated through the use of the Q-peptide hydrogel. Specifically, after co-culture with the Q-peptide hydrogel, murine macrophages were found to produce a mileu of cytokines having a historically pro- and anti-inflammatory effect rather than a pure pro-inflammatory effect as was observed during co-culture with the control hydrogel (Mandla et. al., 2019; Vol. 5, pp 4542-4550). Of particular interest was the reduction of TGF-β1 and stimulation of TGF-β3 after culture with the Q-peptide hydrogel. This shift of TGF-β3/1 ratio is more reflective of that observed in models of scarless wound healing Likewise, as a common treatment for the prevention of EGT in the horse is the application of corticosteroids which reduce the production of TGF-β1&2 which in turn reduces fibroblast proliferation and ECM production (Wilmink, J. M. et. al., *Vet Clin North Am Equine Pract* 2005, 21 (1), 15-32). Thus, the altered cytokine profile induced by the Q-peptide hydrogel may provide some of the benefits of corticosteroids such as controlling EGT production whilst avoiding the negative impacts of corticosteroids on angiogenesis and re-epithelialization (Wilmink, J. M. et. al., *Vet Clin North Am Equine Pract* 2005, 21 (1), 15-32).

Previous studies have additionally demonstrated Q-peptide hydrogel's efficacy in modulating fibrosis, as evidenced by improved tissue function subsequent to healing of a myocardial infarction (Reis, L. A. et. al., *Circ Heart Fail* 2015, 8 (2), 333-41, Cal, H. et. al., *Faseb j* 2019, 33 (7), 8306-8320). As such, it was hypothesized that the treatment of wounds on the equine distal limb with the Q-peptide hydrogel would improve the biomechanical and functional properties of the healing skin. To investigate this, biaxial mechanical testing approach validated in part 1 was utilized to compare the function of healing tissues between treatment groups. At this stage in the wound healing continuum, it was proposed that increased compliance promotes wound closure and a lower viscoelasticity is favorable. At day 42, wounds treated with the peptide-free hydrogel were characterized by a pronounced stiffening of the tissue as high and even beyond that of uninjured skin. The addition of Q-peptide, whether single or repeated, counteracts the premature stiffening of wounds treated solely with hydrogel. Wounds treated with peptide-free hydrogel and single application of the Q-peptide hydrogel also exhibited viscoelastic properties most closely resembling uninjured skin. The adverse response seen in the repeated Q-peptide application wounds is likely confounded by constantly disturbing the wound bed during reapplication of the hydrogel, conditions that were not applied to other groups. Since excessive crosslinking of collagen causes tissue stiffening, it was suspect the addition of the Q-peptide may be supporting keratinocyte and fibroblast survival, preserving a more desirable viscoelastic response while preventing premature stiffening of the tissue, thus promoting wound closure. A clearer understanding of the microstructural changes in the tissue is needed to explain the observed differences in gross mechanical response across wounds and the effects of the Q-peptide on the fiber network.

Treatment contamination between vertically orientated experimental wounds on the equine distal limb should be considered when using the equine distal limb model of wound healing. Physical distancing of wounds is important to prevent this, but intrinsic differences between tissue healing across wound sites must be considered during analysis.

The current study suggests the single topical application of Q-peptide hydrogel bandages is a safe and easily implemented means of improving the incidence of wound closure as well as the functional compliance of healing tissue in an equine model of delayed wound healing. Q-peptide hydrogel may have lasting functional improvements in quality of wound repair including aesthetics, scar thickness, and biomechanical function.

Example 10. Use of QHREDGS (SEQ ID NO: 1) Peptide to Improve Appearance and Sensitivity of Human Skin Sensitive skin, characterized by abnormal sensory stimuli, is a complex dermatological condition which affect many across the globe. In American alone, 60-70% of women and 50-60% of men report having some kind of sensitive skin symptom (Farage et. al., *Front Med.* 2019; 6:98), such as itching, burning, stinging, tightness, and dryness. For many, the problems associated with dry and sensitive skin are compounded by acne. While highly prevalent during the early years of puberty and adolescence, adult acne, or acne experienced past the age of 25, is becoming increasingly more common. In fact, it has been reported that some 40-54% of men and women experience signs of acne past the age of 25 (Cordain L et. al., *Arch Dermatol.* 2002; 138(12): 1584-1590). The above skincare concerns are further compounded by fears of aging skin and wrinkles. As skin ages, it undergoes a number of structural and functional changes, such as reduced collagen and oil production, which leads to wrinkles and dryness. The continual frustration and pain associated with the pursuit of clear skin not only causes psychological effects and lost productivity, but a significant financial burden on the patient and consumer. The global skin care market is currently valued at $148.3 billion USD, and is expected to increase by approximately $9 billion USD each year (Skin care industry: global skincare market size 2012-2025 I Statista. https://www.statista.com/statistics/254612/global-skin-care-market-size/. Accessed Oct. 2, 2020). To complicate matters, consumers are constantly bombarded with ads across the Internet advertising the next best skincare product, and societal pressures perpetuating clear and beautiful skin. This creates the messaging that consumers need to be spending hundreds of dollars for a multi-step skincare routine, with products which are backed by buzzwords and influencers, as opposed to science and facts.

The skin is the largest organ, and is responsible for providing protection, and maintaining moisture and hydration. The skin is a complex system composed of 2 layers, the epidermis and the dermis. The outermost layer, or the epidermis, contains keratinocytes, which are primarily responsible for barrier function, melanocytes, dendritic cells, Langerhans cells, and other immune cells. The dermis, which contains fibroblasts, and immune cells, contains extracellular matrix which provides cellular support (Cailedo-Dorantes et. al., *Int J Inflam.* 2019; 2019).

As with all organs, the skin is susceptible to aging, as characterized by thin and dry skin marked with wrinkles. While aging skin is inevitable, the signs of aged skin can be accelerated by external factors such as air pollution, smoking, and sun exposure, which culminates in a loss of skin elasticity and coarse wrinkles. Physiologically, there is a marked decrease in proliferation of keratinocytes and fibroblasts, and a reduction in collagen production. Common non-invasive treatments and preventative measures for aging skin include the application of creams and gels containing antioxidants and retinoids, however due to the protective barrier created by keratinocytes, care must be taken when designing creams that work to maximize molecule delivery and penetration (Zhang S, et. al., *Cell Transplant,* 2018; 27(5):729-738).

Conversely, acne vulgaris is a skin condition which predominantly affects adolescences, however in recent years, its prevalence has risen in young adults in their 20s and 30s. Unlike aging skin, acne plagued skin is often associated with an increase in oil and grease production, leading to prolonged inflammation (Bhate K, et. al., *Br J Dermatol.* 2013; 168(3):474-485). While treatment regimens vary case by case, topical retinoids have proven effective in reducing inflammation and facial lesions (Leyden J J. *J Am Acad Dermatol.* 2003; 49(3 SUPPL.):S200-S210).

Herein is described the development of a lightweight moisturizer and its use in an informal survey amongst North American and Asian subjects. This moisturizer, named Kerra, was formulated using a novel biomimetic peptide sequence, QHREDGS (SEQ ID NO: 1) (INCI name: sh-heptapeptide-10 SP), which was demonstrated to reduce keratinocyte death in the presence of reactive oxygen species (Xiao et. al., doi:10.1073/pnas.1612277113). When used by North American subjects, there is an overwhelmingly positive response amongst an older population (>40 years old), while in China, younger subjects with both dry and oily skin reported positive effects. Further, Kerra was used by a small group of subjects with moderate to severe acne who reported improvement within 5 days of use.

Methods
Cream Formulation

The light weight moisturizer, Kerra, was formulated by a water-in-oil emulsion. Briefly, the water phase containing water/aqua, glycerine, DL-Panthanol, and xanthan gum, and the oil phase containing rosa mschata seed oil, cetyl alcohol, glyceryl stearate, butyrospermum parkii, cetearyl olivate, and sorbitan olivate was heated. Once melted and stirred, the water phase was added to the oil phase and was emulsified until smooth. Once the cream had cooled down to room temperature, collagen and the novel peptide sequence, sh-Heptapeptide-10 SP was added, as well as the preservative, ebnxyl alcohol and ethylhexylglycerin. The cool down phase was mixed until incorporated and the cream was added into tubes and sealed.

North American Survey Collection

North American subjects who received free samples of Kerra were contacted after a week and asked to fill out a survey. The survey collected their age range, and asked participants to select their skin type (they were allowed to select more than one). Participants were then asked the following YES/NO questions based on their experience using Kerra:

1. I felt that Kerra made my skin look less irritated.
2. I felt that Kerra made my skin feel more hydrated.
3. I felt that Kerra made my skin look healthier.
4. I felt that Kerra made my skin feel smoother.
5. I felt that Kerra improved the overall appearance of my skin.

Chinese Survey Collection 30 volunteers visiting beauty salons in Shanghai were asked to enroll in this survey. Once consent was provided, each participant was given 2 tubes of cream to use at home. After 7 days, participants were asked to fill in online survey about their experience using Kerra. 26 participants completed the survey, with 14 having dry or oily skin, and 8 reporting acne. They survey collected their age range and skin type. Participants were asked the following questions:

1. How does Kerra compare to your current skin care product?
2. Answer YES/NO to the following questions. After Kerra my skin feels . . .
3. Tighter
4. Smoother
5. Less sensitive
6. More hydrated
7. No comment
8. Rate the following statements using a Likert scale (strongly agree to strongly disagree) based on your experience when apply Kerra
9. Kerra feels thick
10. Kerra feels refreshing
11. Kerra is not creamy
12. Kerra is not too oily
13. Kerra is not too watery
14. Kerra has a homogenous texture
15. Kerra has a pleasant viscosity
16. Kerra is very absorbent
17. Kerra is easy to spread Rate the following statements using a Likert scale (strongly agree to strongly disagree) based on your experience after using Kerra for a week.

1. My skin is not too oily
2. My skin feels moisturized
3. My skin feels refreshed
4. My skin feels soft
5. My skin feels smooth 6. My skin does not feel sticky
7. My skin feels firm
8. Kerra penetrates my skin well
9. I think Kerra is suitable for my skin If volunteers reported acne prone skin, they were instructed to answer the following survey:

10. Rate pain from acne from very minor, minor, severe, to very severe.
11. Rate redness from acne from very minor, minor, severe, to very severe.
12. On day 1, 2, 3, 4, 5 did you notice:
    a. Pain reduction
    b. Redness reduction
    c. Overall improvement in skin
    d. Acne reduction
    e. No change
    f. Unsure
13. Rate the overall effect of Kerra on your skin: Very good, good, neutral, bad, very bad.

Results and Discussion

Respondent Population

Figure 21A:
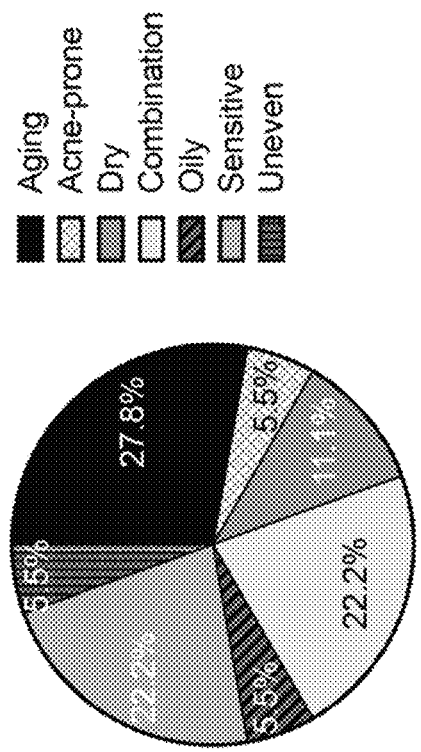
FIGS. 21A-21D show a series of pie graphs depicting subject respondent summary in an example of the present disclosure.
Figure 21B:
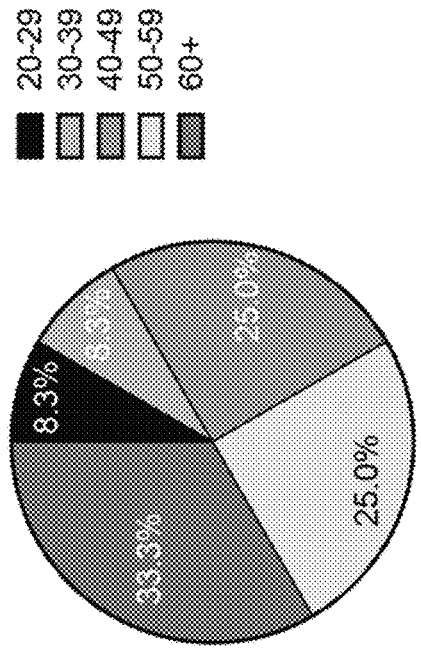
Figure 21C:
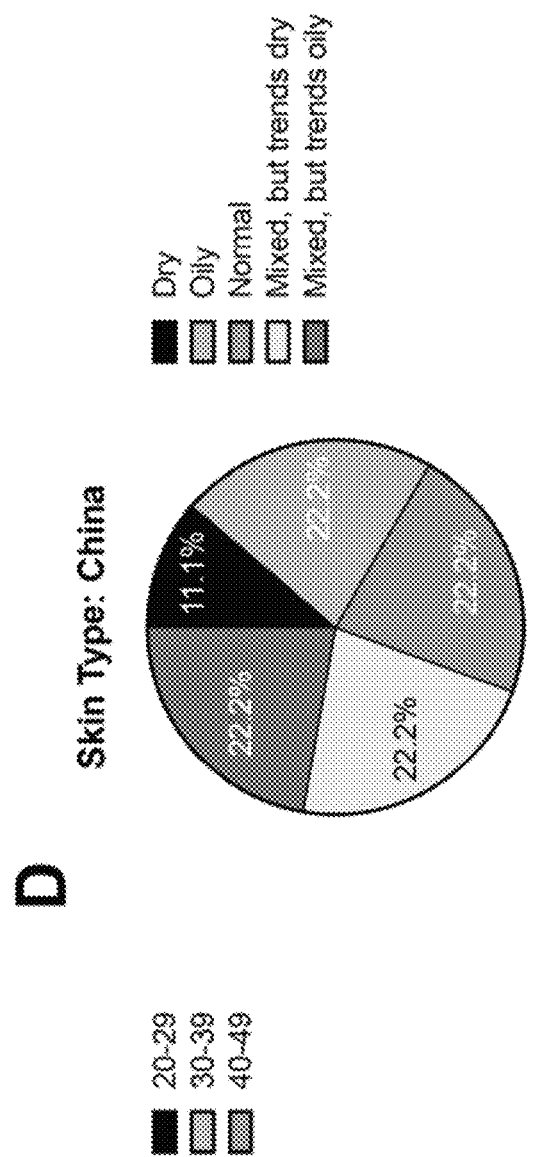
Figure 21D:
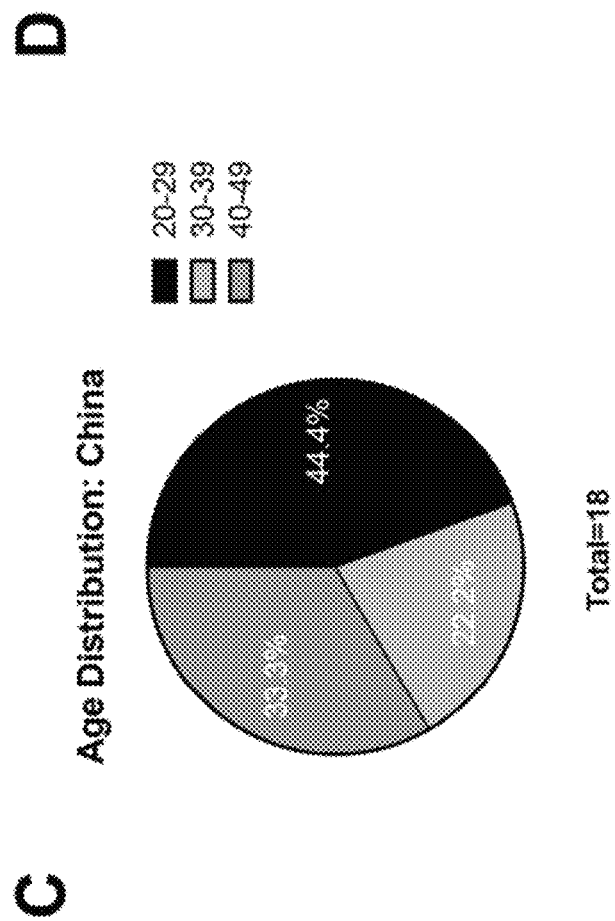

Subjects in North America and China were given Kerra, a lightweight face moisturizer, and after about a week of use, subjects were asked a series of questions aimed at increasing understanding of the user experience. Within North America, questions were designed to gain a quick, high level insight into how the product made their skin feel, whereas the survey in China prompted users to reflect on both product experience, and how their skin felt. Within North America, a total of 12 participants were surveyed, a majority of which were above the age of 40 (FIG. 21A). Survey participants were asked to categorize their skin type. The participants were allowed to select multiple skin types, with aging being the most common skin type observed, followed by sensitive skin and combination skin (FIG. 21B). In the Chinese survey, a total of 18 participants were surveyed and the average age of survey responder was under 40 (FIG. 21C). Chinese respondents reported an even distribution of dry and oily skin (FIG. 21D). Two out of twelve respondents in North America identified as male, whereas all Chinese respondents identified as female. These two survey respondent subsets allowed for insight to be gained into 3 different subject populations; subjects with 1) aging skin, 2) young dry skin and 3) young oily skin.

North American Survey Respondents felt that Kerra Improved Skin Appearance.

In an effort to maximize respondent engagement levels, a short survey was sent out to North American subjects who had recently received a free sample of Kerra. In addition to age and skin type, subjects were asked a series of 5 YES/NO questions designed to gain insight into their use experience. Results were overwhelmingly positive and in support of Kerra.

Figure 22A:
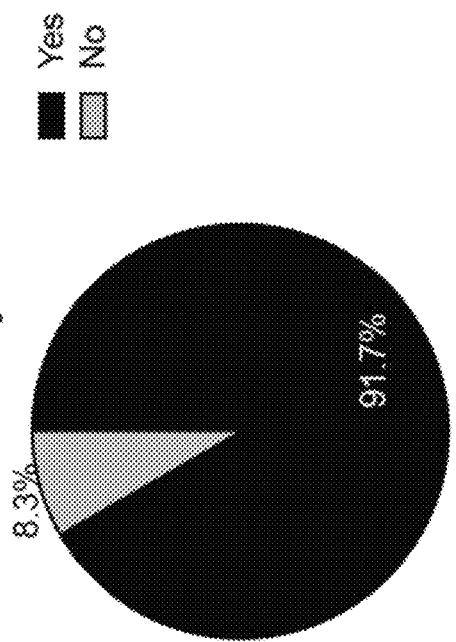
FIGS. 22A-22E show a series of pie graphs depicting that majority of North American users report positive effects while using Kerra (which comprises the Q-peptide hydrogel) in an example of the present disclosure. Participants were asked to respond with YES/NO to the following statements.
Figure 22B:
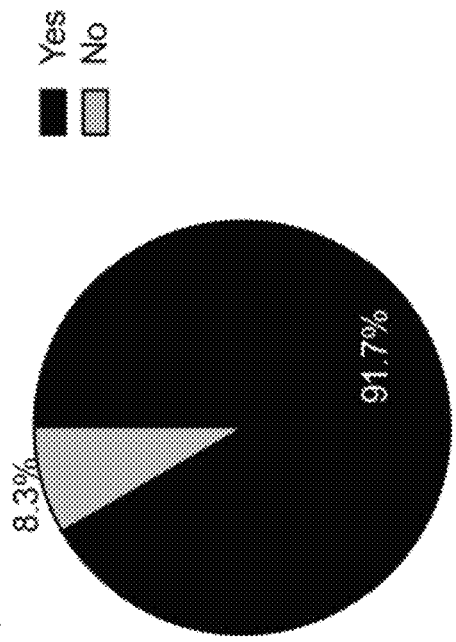
Figure 22C:
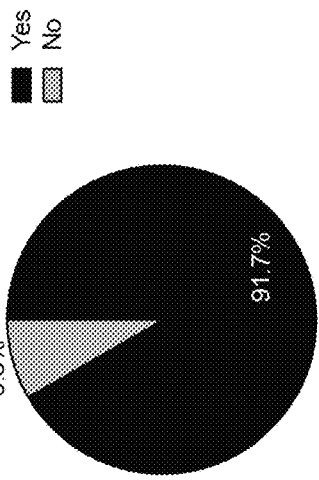
Figure 22D:
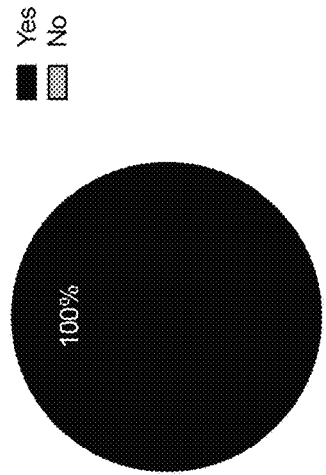
Figure 22E:
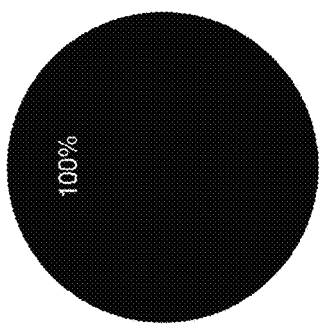

About 92% (11/12) of respondents felt that Kerra made their skin look less irritated, feel more hydrated, and smoother (FIGS. 22A, 22B, 22D), and 100% of respondents felt that Kerra made their skin look healthier and felt that Kerra improved the overall appearance of their skin (FIGS. 22C, 22E). Interestingly, looking at the raw data, the same subject responded no when asked if Kerra made their skin look less irritated, more hydrated, and smoother. This subject is in fact under the age of 40, falling outside of the majority of respondents, suggesting that Kerra may be best suited for subjects above the age of 40. However, with only 12 respondents, this survey merely serves as a first step to understanding the North American user experience.

Chinese Respondents Perceived Kerra Differently Depending on Skin Type.

Figure 23A:
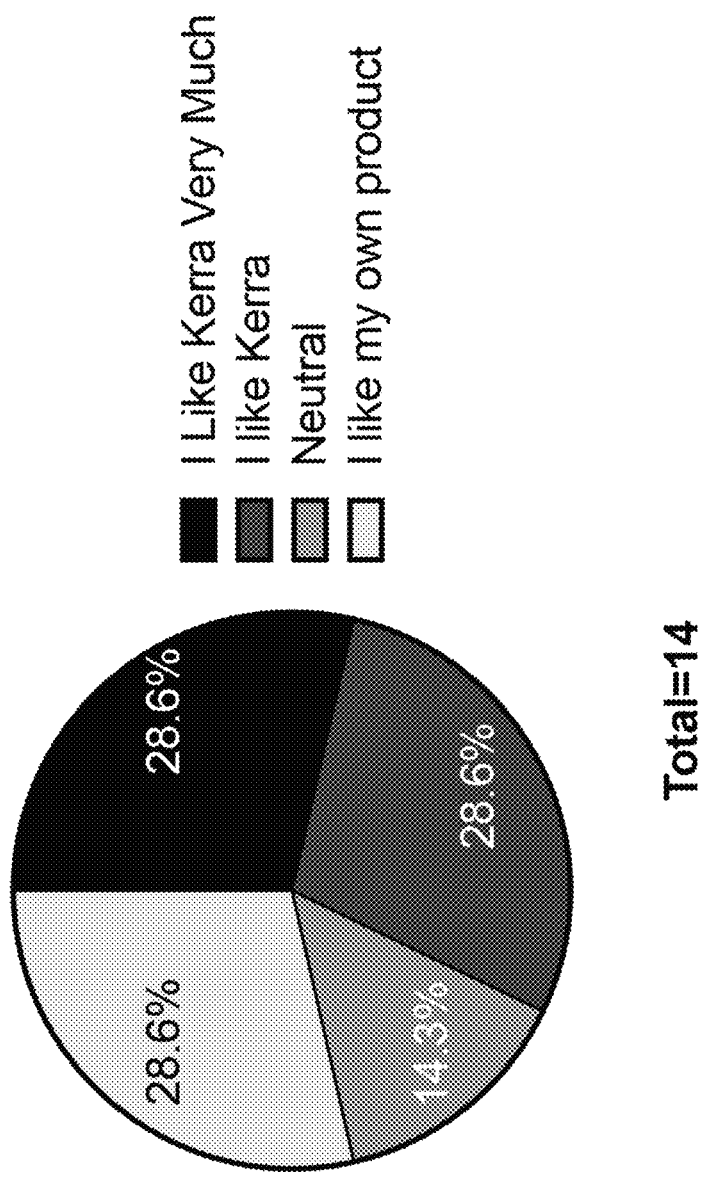
Figure 23B:
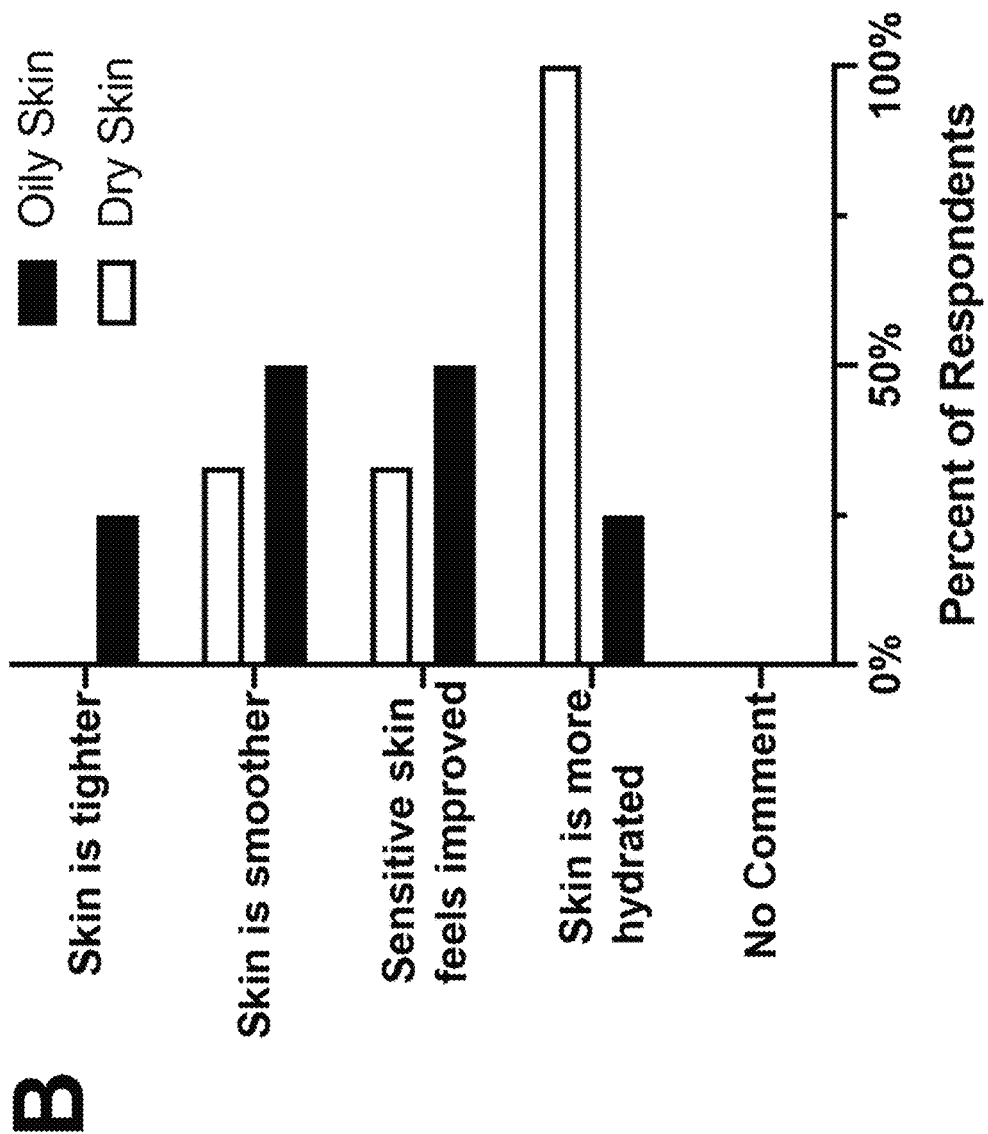

In the survey distributed to Chinese subjects, the questions were designed to extract feedback on the product itself, and on the user experience after using it for a period of time. Overall, the majority of respondents (>57.2%) reported enjoying Kerra with only 28.6% preferring their currently used skincare product (FIG. 23A). Interestingly, if analyzed based on skin type, a number of trends begin to emerge. When asked a series of YES/NO questions, 100% of the subjects with dry skin responded that their skin felt more hydrated after using Kerra, vs only 25% of subjects with oily skin. Conversely, more subjects (50%) with oily skin felt that Kerra improved their sensitive regions, and their skin felt smoother overall (FIG. 23B).

Figure 23D:
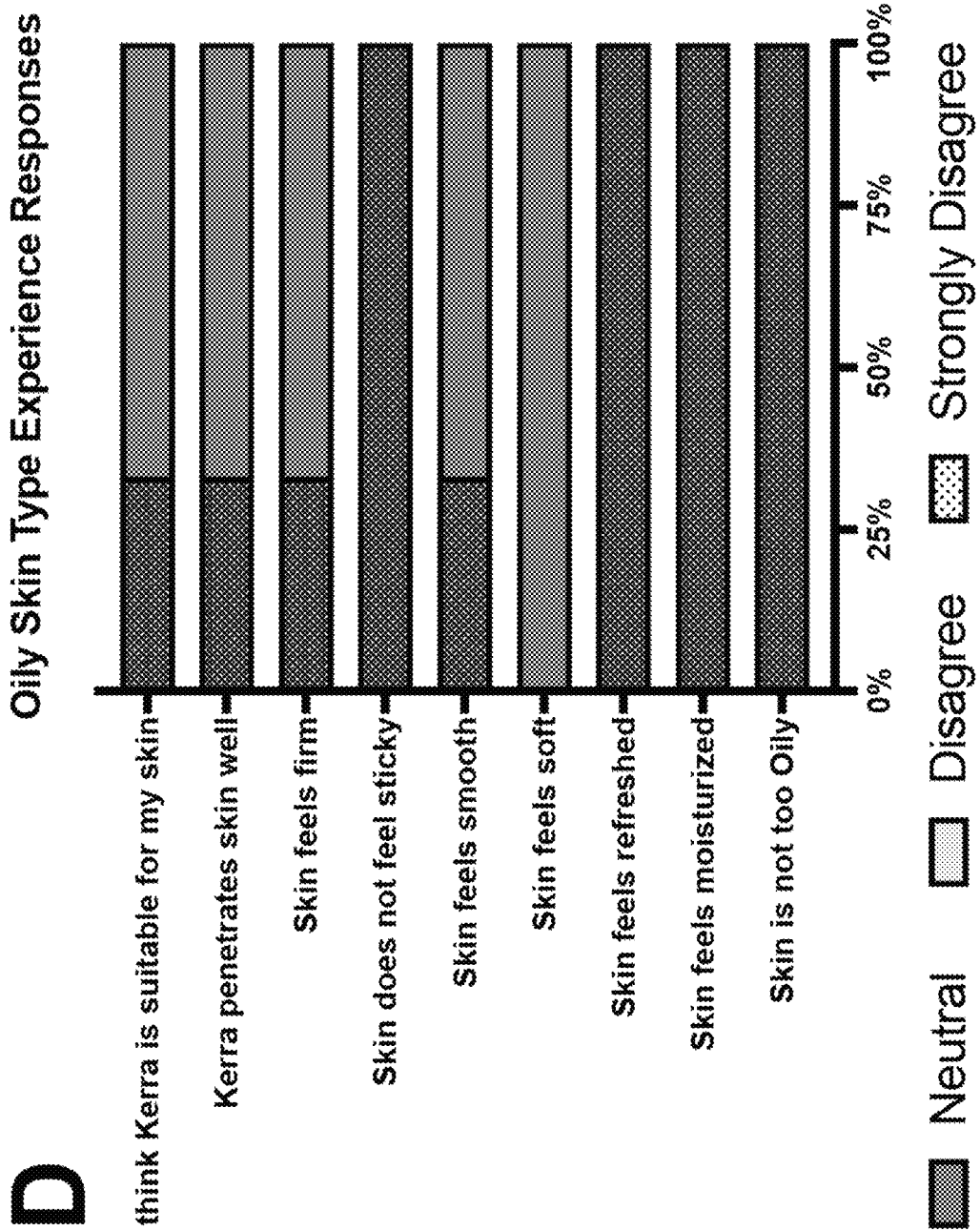
Figure 23E:
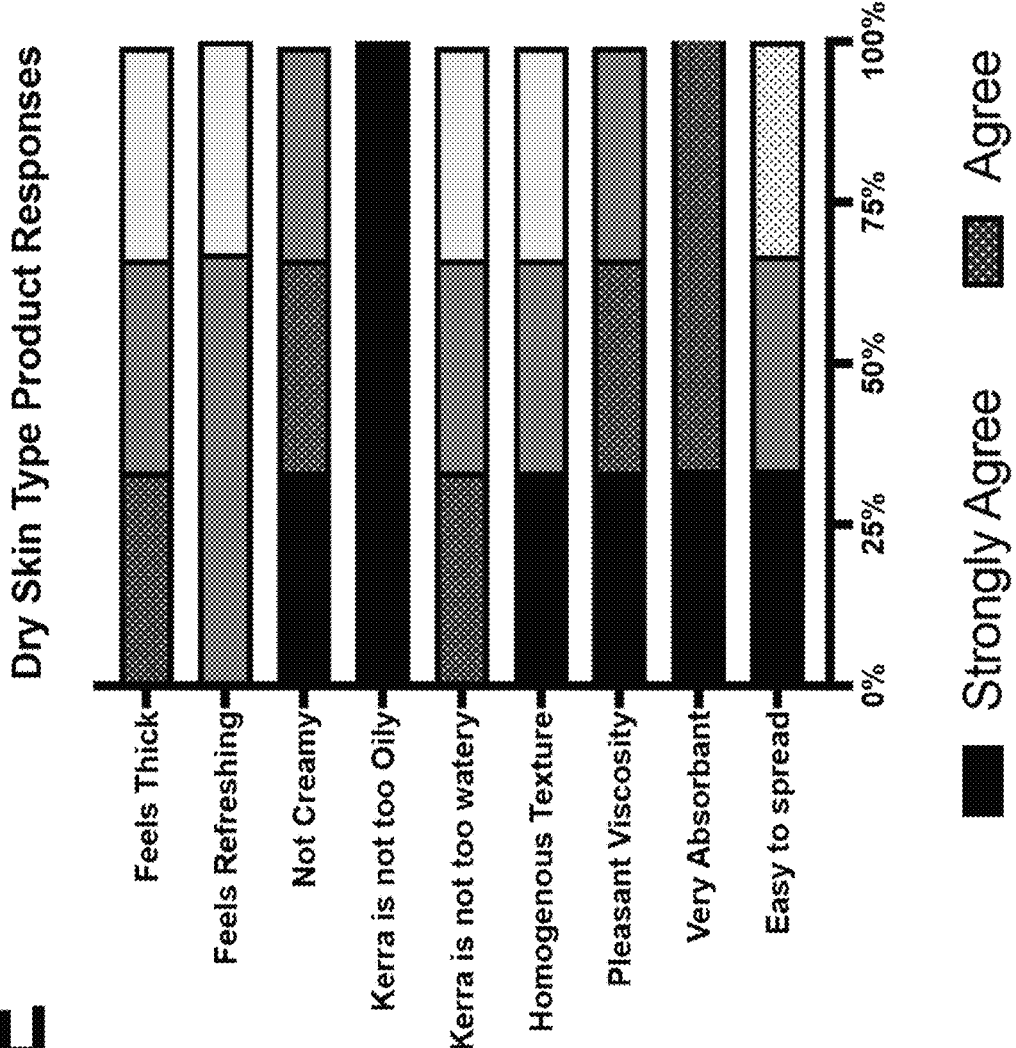
Figure 23F:
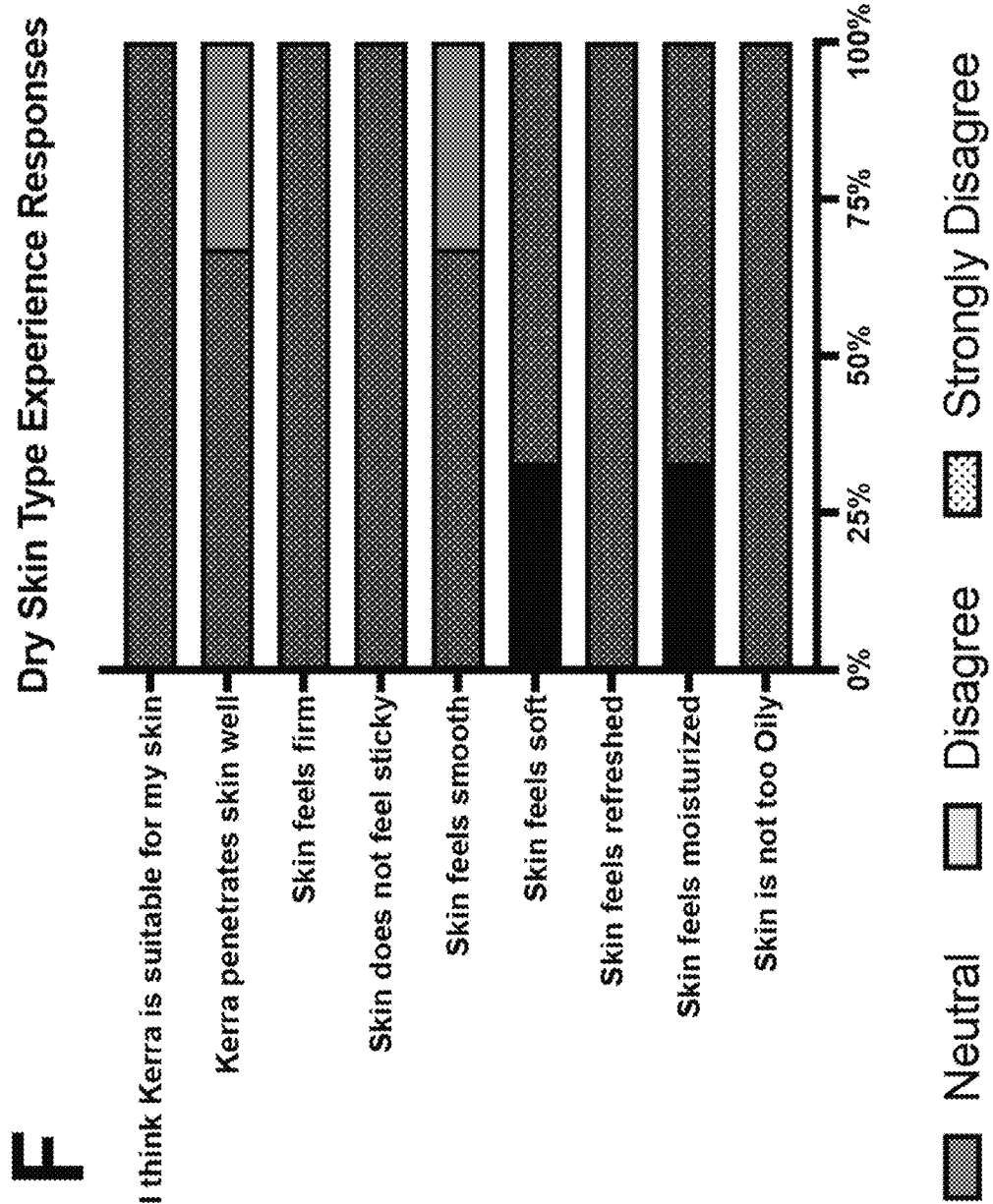

Respondents were then presented with a series of statements regarding their experience of applying Kerra, and their skin after using Kerra for a week, and asked to respond using the Likert Scale. Respondents with dry skin more commonly felt that Kerra was thick and generally refreshing, whereas respondents with oily skin did not think that Kerra felt as refreshing (FIG. 23C, 23E). Instead, respondents with dry skin did not think Kerra was too oily, and felt that it absorbed well on their skin. After using Kerra for 7 days, respondents with oily skin were pleased overall, and 100% agreed that their skin did not feel oily, or sticky, but felt moisturized and refreshed (FIG. 23D). Meanwhile, dry skin respondents noted that their skin felt moisturized and soft after 7 days of use (FIG. 23F). This survey demonstrates that Kerra is suitable for both dry and oily skin, however, user experience greatly varies based on skin type. This is important for understanding that while Kerra can be used by subjects with different skin types, their use cases and need that Kerra would fill differs. This information is important in design future marketing material which will allow for development of a usage campaign or regimen that is personalized to different skin types.

Kerra helps to improve symptoms of acne after 5 days of usage.

Figure 24A:
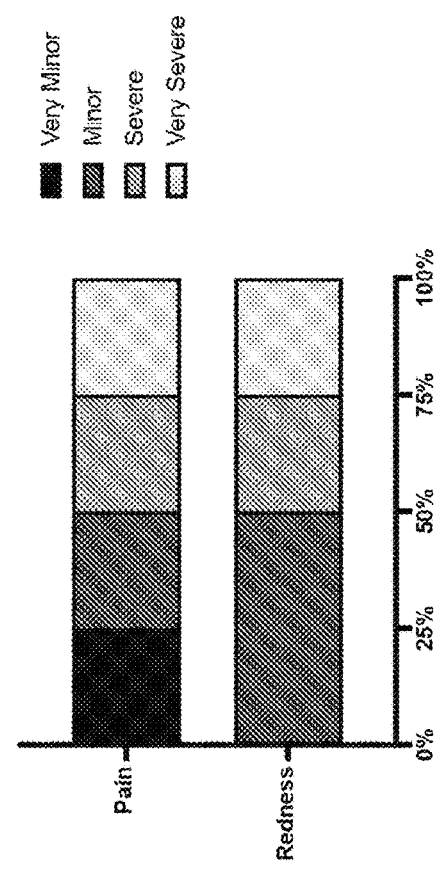
FIGS. 24A-24C show a series of graphs showing respondents with acne prone skin noticed positive effects after using Kerra in an example of the present disclosure.
Figure 24B:
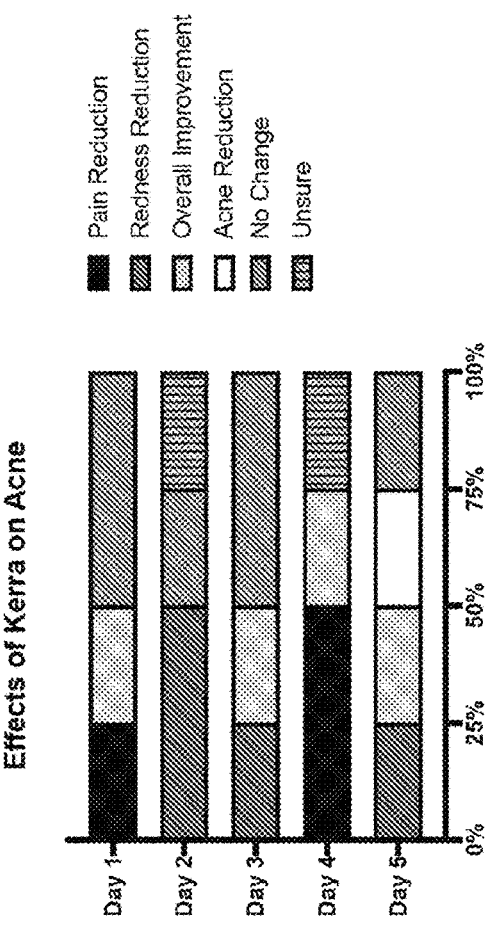
Figure 24C:
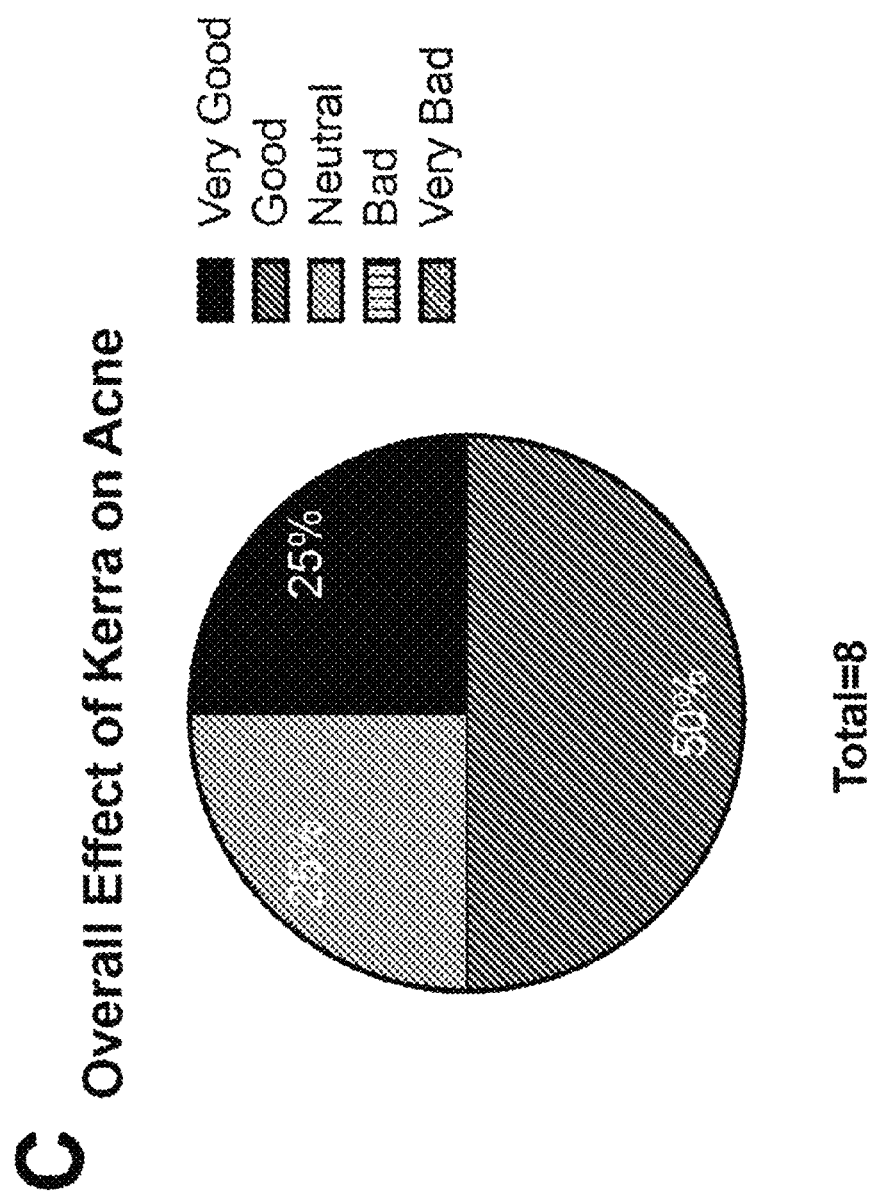

In an effort to understand the effect of Kerra on acne prone skin, eight subjects with varying degrees of acne were given a sample and asked to report how Kerra effected their acne. At baseline, many of the participants reported minor to very severe pain or redness as a result of their acne (FIG. 24A). Remarkably after only 1 day of usage, 25% of respondents had reported pain reduction and an overall improvement in their skin. By day 5, 2 respondents (25%) had reported a reduction in acne, and another 25% percent reported a reduction in redness and an overall improvement in their skin (FIG. 24B). Overall, 75% of the acne users felt as though Kerra had an overall positive effect on their acne (response of "good" or "very good"), with the remaining 25% experiencing a neutral effect (FIG. 24C). The results from this study show early promise that Kerra may be an effective treatment for reducing moderate signs of acne.

In conclusion, Kerra was reported to have a positive effect on most skin types, including aging, dry, oily, and acne prone skin. No negative feedback or adverse reactions were reported in either China or North America.

Example 11. Use of QHREDGS (SEQ ID NO: 1) Peptide to Improve Recovery after Energy-Based Skin Procedures Laser resurfacing and microneedling is a common dermatological procedure for aging and skin discolouration. However, there are often long and painful recovery times marked with enhanced redness and purpura. The Kerra Rescue Regimen (Quthero Skincare), a two-step skincare procedure consisting of a Rescue Gel and Rescue Ointment was used following laser resurfacing and microneedling. In this split-face, multi-center, blinded study, participants treated half of their face with the Kerra Rescue Regimen, and the other half with a comparator regiment (bland gel and CeraVe™). Image analysis demonstrates improved quality of skin as early as day 2 post-procedure, and subjects reported "better feeling" skin on the Kerra Rescue Regimen side.

Energy-based procedures, such as laser face resurfacing and radiofrequency microneedling are common dermatological procedures for aging and discoloured skin. During microneedling and laser resurfacing, the top layer of the skin, also known the epidermis, is damaged. As a result of this micro-injury, the growth of new skin cells is stimulated, resulting in the production of new ECM proteins, such as collagen. While laser resurfacing and microneedling has been demonstrated to have successful effects on aging and discoloured skin, a long recovery time still prevails, resulting in major concern for many patients. This recovery time, which can take upwards of a week, is marked by pain, erythema, scabbing and dyspigmentation.

Herein, the Kerra Rescue Regimen, a two-step skin care routine, for the management of skin following energy-based dermatological procedures is presented. The Kerra Rescue Regimen includes the Rescue Gel, a hydrating gel containing the potent Q-Peptide system, and the Rescue Ointment, a thick hydrating ointment to lock in moisture. The Q-Peptide system has been demonstrated to stimulate the production of new collagen, decrease inflammation and promote a pro-healing immune phenotype, and promote epidermal migration and survival (Mandla, S., et al. *ACS Biomater. Sci. Eng.* 5, 4542-4550 (2019); Xiao, Y. et al. *Proc. Natl. Acad. Sci. U.S.A* 113, E5792—E5801 (2016)). The Kerra Rescue Regimen, containing the Q-Peptide system, is shown herein to shorten the downtime associated with energy-based treatments, by accelerating recovery and improving the appearance of the skin.

The primary objective of this study was to evaluate the Kerra Rescue Regimen following laser or energy-based treatment of the face, specifically fractional ablative and nonablative treatment with any type of laser, radiofrequency microneedling, microneedling and dermabrasion. This study was designed as a split-face blinded trial, in which half of the face was treated with the Kerra Rescue Regimen and the other half was treated with a comparator regimen. Primary endpoints included examination of skin appearance. Secondary endpoints included examining subject satisfaction and skin texture.

Methods

Study Design

Figure 25:
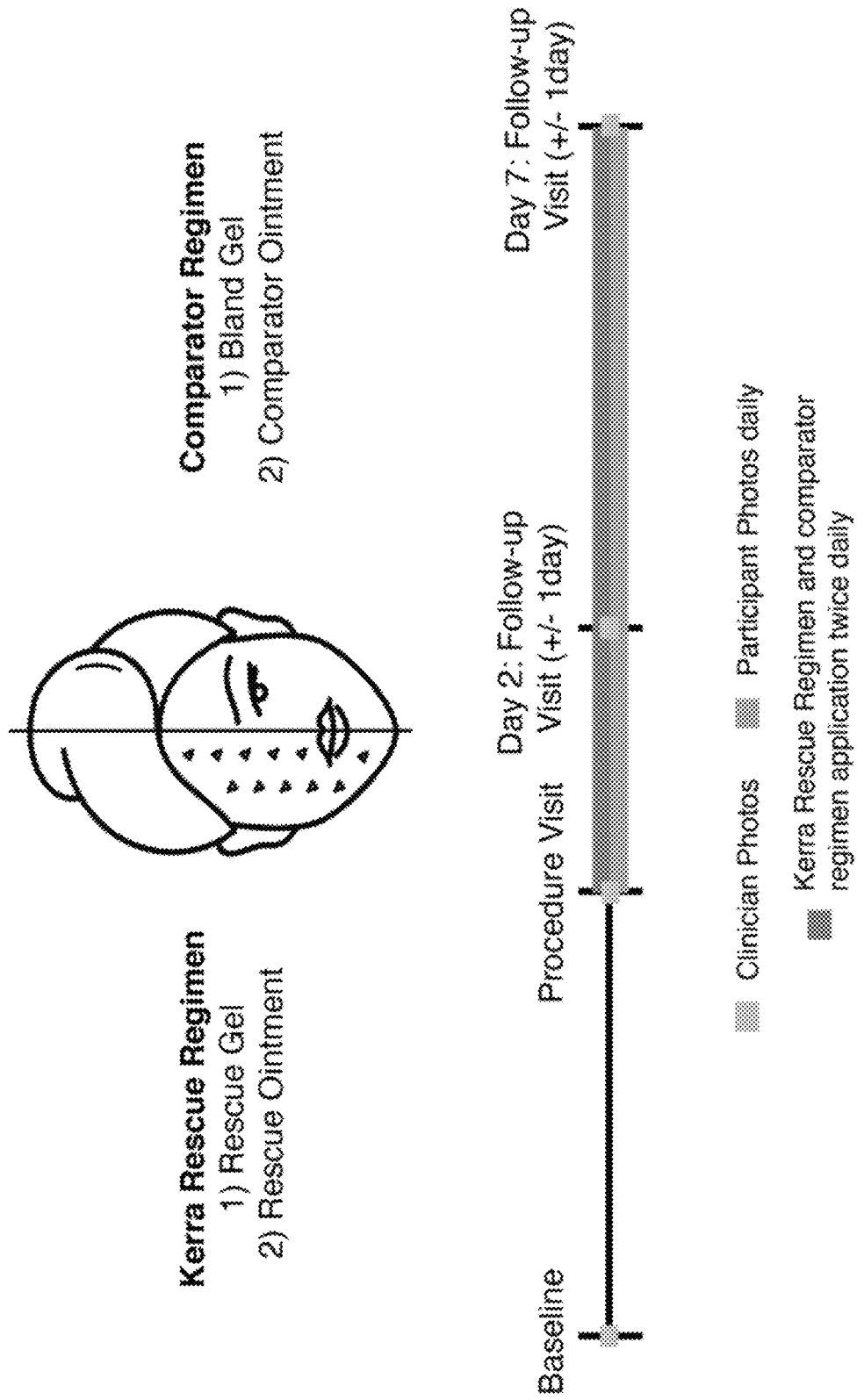
FIG. 25 shows a clinical trial schematic overview of a study of a use of the QHREDGS (SEQ ID NO: 1) peptide, according to an example of the present disclosure. In this split-face trial, half the face was treated with the Kerra Rescue Regimen (which comprises the Q-peptide hydrogel), and the other half was treated with the comparator regimen.

The present study was an investigator-blinded, randomized, split-face clinical study comparing the Kerra Rescue regimen to a standard of care regimen (containing a bland gel and petrolatum-based ointment). All subjects were undergoing a laser or energy based device treatment, specifically, dermabrasion, non-ablative fractional laser, ablative fractional laser, radiofreqeuency microneedling and microneedling for any indications such as: skin rejuvenation, resurfacing, reduction of acne scars, lentigines, or photodamage. Subjects received a baseline assessment during enrollment, immediately post-procedure, and during a follow up visit on day 2 (+/−1 day) and day 7 (+/−1 day) (FIG. 25). A split-face study design was employed to allow for each participant to act as their own control. The study was approved by an independent Institutional Review Board prior to initiation. The timeline in FIG. 25 outlines notable study dates. Photos were captured by the clinician during the baseline screening visit, immediately post-procedure, and during follow-up visit 1 (day 2+/−1) and follow-up visit 2 (day 7+/−1). Immediately post-procedure, the participant used the Kerra Rescue Regimen on one side, and the comparator regimen on the other side twice daily. Participants captured photos daily following the procedure.

Materials

The Kerra Rescue Treatment includes a Q-Peptide recovery gel (Kerra Rescue Gel; Quthero Skincare) and a Q-Peptide recovery ointment (Kerra Rescue Ointment; Quthero Skincare). The standard of care regimen consisted of a bland gel (Formulated by Quthero Skincare) and a petrolatum-based cream (CeraVe Healing Ointment; CeraVe)

The Q-Peptide gel used in this study contains Water/Aqua/Eau, Propanediol 1-3, DL-Panthenol, Sodium Hyaluronate, Collagen, Chitosan, sh-Heptapeptide-10 SP, *Silybum Marianum* Seed Extract, Glycerin, *Calendula Officinalis* (Calendula) flower extract, Hydroxyethylcellulose, Sodium Carbomer, Xanthan Gum, dimethicone, Benzyl Alcohol, Ethylhexylglycerin. The Q-Peptide Ointment contains Petrolatum, Butyrospermum Parkii (Shea Butter), *Rosa Moschata* (Rose hip) seed oil, Water/Aqua/Eau, Glycerine, DL-Panthanol, Glyceryl Stearate, Collagen, sh-Heptapeptide-10 SP, Xanthan Gum, Benzyl Alcohol, Ethylhexylglycerin.

The bland gel contains Water/Aqua, propanediol 1-3, DL-panthenol, hyaluronic acid, *Silybum Marianum* Seed Extract, glycerin, *calendula Officinalis* (Calendula) flower extract, hydroxyethylcellulose, sodium carbomer, xanthan gum, benzyl alcohol, ethylhexylglycerin, dimethicone.

Subjects 13 healthy subjects with Fitzpatrick skin types I-IV undergoing any type of fractional ablative, nonablative laser treatment, dermabrasion, or radiofrequency microneedling for the following indications: skin rejuvenation, skin resurfacing, reduction of acne scars, reduction of lentigines, or reduction of photodamage were enrolled in this study. Written informed consent was obtained from each participant at the time of enrollment, and photographic release. Subjects were compensated with a discount at future procedures at completion of milestones during the study. Exclusion criteria included: presence of an active systemic or local skin disease in the area to be treated, an allergy or hypersensitivity to any ingredient in the products, evidence of active cancer or a diagnosis and an untreated cancer within the past year, presence of dermatitis or eczema in areas to be treated, open wounds or lesions in the area(s) to be treated, history of vitiligo, those receiving an intervention that could interfere with lentigines, treatment with any energy device, drug, or cosmetic intervention for lentignes, tanning within prior 7 days or expectation of tanning, pregnancy or breast feeding within last 6 months. Subjects must also not have use of systemic steroids within past 3 months, use of systemic retinoids treatment within past 12 months, or use of topical treatment with alpha-hydroxy acids within the past 14 days. Subjects must also not have treatment with IPL, ablative resurfacing laser, nonablative resurfacing laser, or light chemical peels for 3 months, or medium to deep chemical peels for 3 months. Nor must they have history of using topical or oral tranexamic acid within 4 weeks, chemotherapy for hormone modulation in breast in past 6 months, or psychiatric drugs that in the investigator's opinion would impair the subject from understanding the protocol requirements or the informed consent form.

Intervention

Subjects were randomized using block randomization with block sizes of 2 for each study site prior to initiation of the treatment to determine which side of the face was set to receive which treatment. The study investigators, clinicians, and participants remained blinded during the duration of the study. Prior to successful enrollment, participants were asked to complete patch testing for the purpose of identifying a possible allergic reaction. The materials were supplied in identical containers labelled A, B, C, D. The participants were asked to apply one material at a time to 4 different locations of the forearm, followed by an observation period of 24 hours. Should any redness or irritation appear after the application of the treatment of control materials, the participants would not be eligible to continue with the trial.

Prior to the procedure, a topical anesthetic gel was applied and standard protocol for each skin type and for each procedure was used. Subjects then underwent a laser or energy-based device treatment specifically, dermabrasion, non-ablative fractional laser, ablative fractional laser, radiofreqeuncy microneedling and microneedling.

Immediately following the procedure, participants were instructed on how to apply their recovery regimens. As this was a split-face trial, participants received both treatments, in identical labelled tubes, labelled LEFT 1, LEFT 2, RIGHT 1, RIGHT 2 containing the Kerra Treatment and the Control Treatment materials according to their randomization. Immediately after the treatment, one side of the face was treated with the Rescue Treatment, consisting of (1) Kerra Gel applied first and followed by (2) the Kerra Ointment. The other side was treated with the standard of care treatment, consisting of a (1) a bland gel, and followed by (2) a petrolatum-based cream.

Assessment

Subjects were evaluated in the office during the enrollment visit, immediately post procedure, and on post-procedure follow up visit 1 (day 2, +/−1 day) and post-procedure follow up visit 2 (day 7+/−1 day). Profile and portrait photos were taken by the clinician during these clinic visits for image analysis. Participants were asked to take self-photographs everyday post procedure from day 1 to day 7.

Photographs were imaged using FIJI (ImageJ; NIH). A macro was written to automate the process and remove bias. Briefly, a white balance corrector was run on all images to account for any differences in photography. A region of interest (ROI) was created on the participant's check and the image was cropped. The colour channels were split into their individual red, green, and blue channels. The green channel was used for analysis as it had the greatest contracts between skin and skin texture. The background was subtracted (with a rolling ball radius of 500). The default threshold was applied, and the mean value (MPV) and area was measured for each image. The total colour difference, $\Delta E^*$, was calculated by converting the RGB image to the CIE L*a*b* colour coordinate system. The MPV was measured, and the $\Delta L$, $\Delta a^*$, $\Delta b^*$ was measured by calculating the difference between the post-procedure visit 1 images and immediately post-procedure. Finally, $\Delta F^*$ was calculated using the equation below:

$$\Delta E^* = \sqrt{(\Delta L^{*2} + \Delta a^{*2} + \Delta b^{*2}}$$

Statistical Analysis

Data from 12 subjects were analyzed; one subject was excluded from analysis after the data were deemed outliers. Data is presented as mean+/−standard deviation. A paired 2-tail t-test or a Wilcoxon test was performed where indicated. A P-value of 0.05 or less was considered significant.

Results

Subjects

Of the 13 subjects enrolled in the study, 1 was excluded as they received their laser procedure on their hands. 12 participants received either fractional ablative, nonablative laser treatment, dermabrasion, or radiofrequency microneedling on their face, and successfully completed the study. There were 10 women, and 2 men. There were no observable differences between baseline characteristics between the participants. 10 participants received fraxel laser face resurfacing and 2 participants received microneedling.

Skin Recovery

Figure 26:
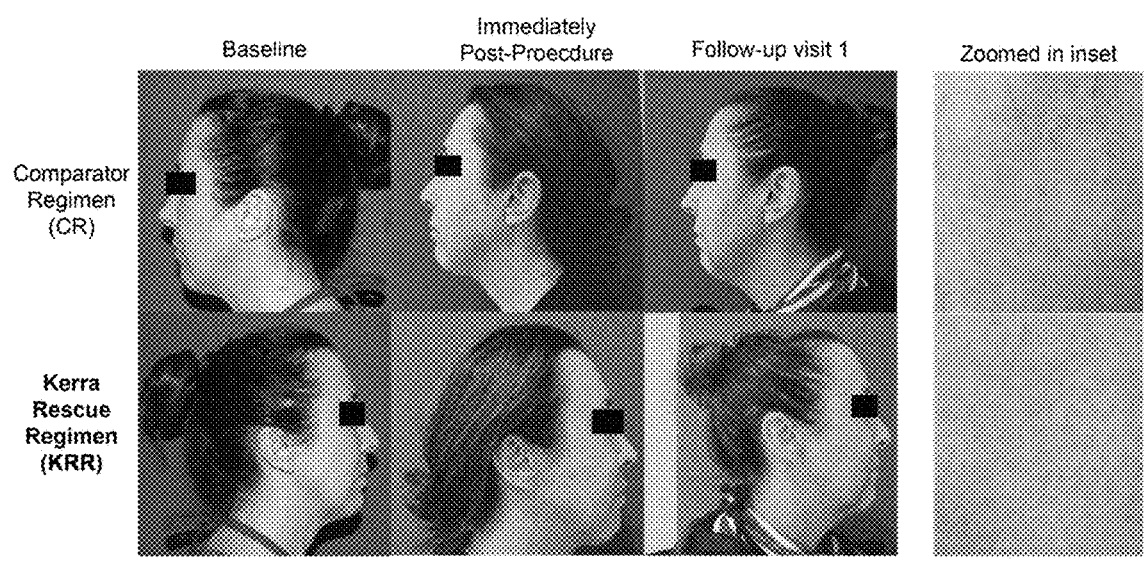
FIG. 26 shows representative photos of participants who received A) microneedling and B) laser face resurfacing in the clinical trial illustrated in FIG. 25.
Figure 26:
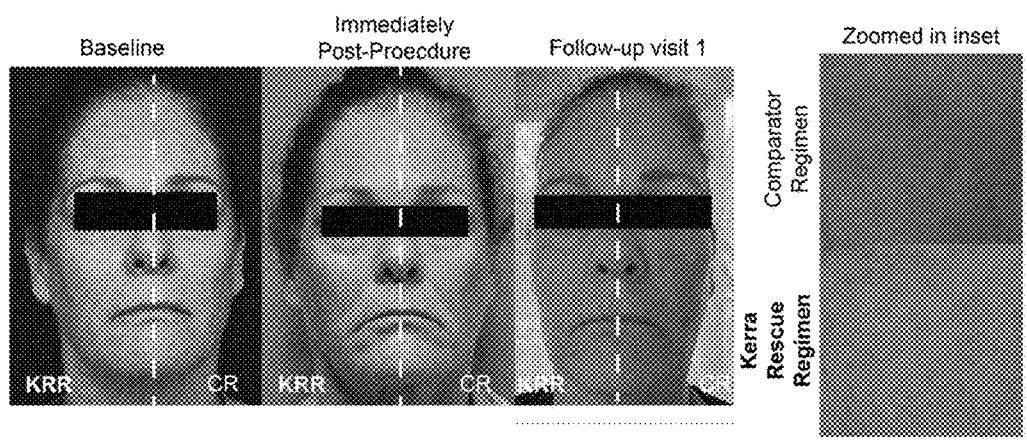

Representative images from a participant who received fraxel laser face resurfacing and a participant receiving microneedling can be found in FIG. 26. Regardless of procedure, there is an observable visual reduction in redness, irritation, and purpura after treatment with the Kerra Rescue Treatment on the first follow-up visit (Day 2+/−1) (FIG. 26). There were no observable differences in exudation, lentigines, or tone.

Figure 27:
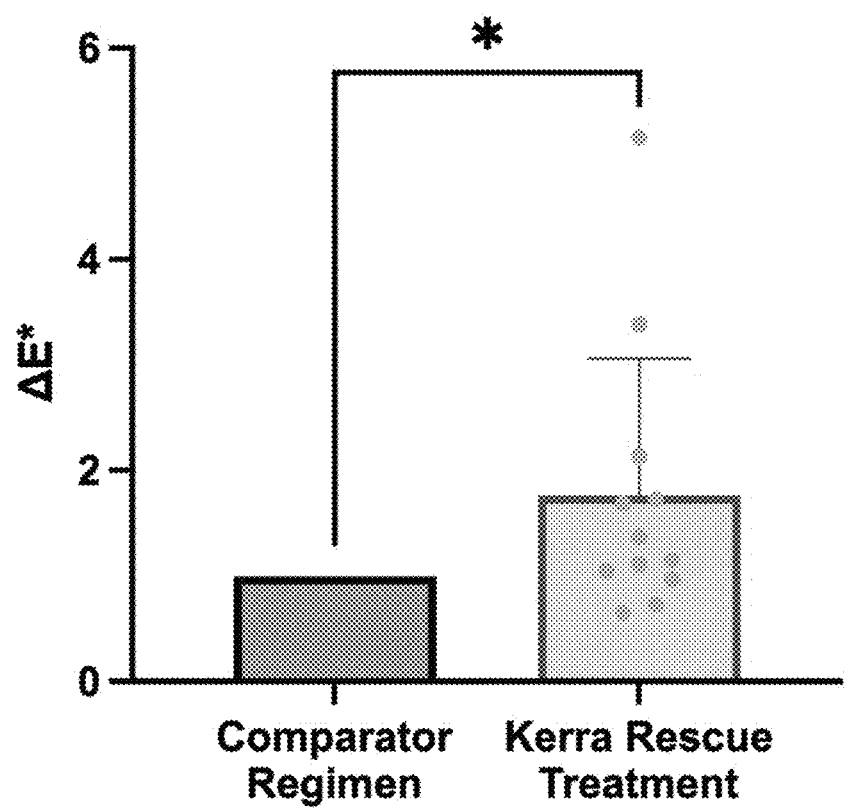
FIG. 27 is a bar graph illustrating that the Kerra Rescue Regimen supports a greater recovery and change in skin colour and appearance by day 2 as measured by ΔE*, in an example of the present disclosure. Data plotted are mean+/−SD. Wilcoxon Test performed. *=p<0.05.

Change in skin colour and appearance, $\Delta E^*$, from immediately after the procedure to the first follow-up visit (Day 2+/−1) was quantified (FIG. 27). $\Delta E^*$ is calculated from the CIE L*a*b* colour space where L* is the luminosity, a* is the green-red colour space, b* is the yellow-blue colour space, and $\Delta E^*$ represents the total change in colour and appearance. Kerra Rescue treated skin had a significantly greater $\Delta F^*$ compared to the comparator regimen, suggesting the Kerra Rescue Regimen supports a greater recovery in skin colour and appearance.

Skin Quality

Figure 28:
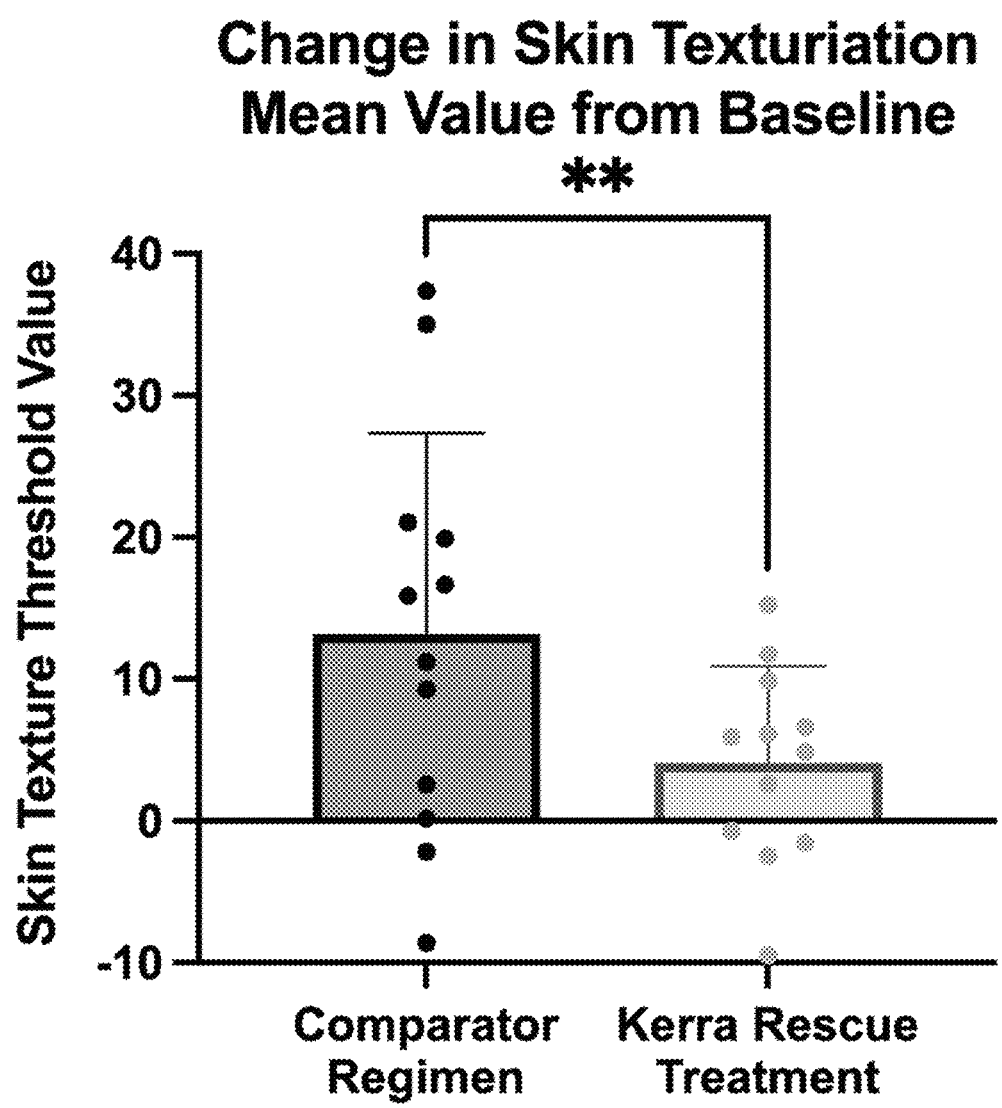
FIG. 28 is a bar graph illustrating that the Kerra Rescue Regimen improves skin texture by day 2 by promoting a faster recovery to baseline levels of skin texture, in an example of the present disclosure. Data plotted are mean+/−SD. Student t-test performed. *=p<0.05.

Skin quality was quantified using image analysis and thresholding techniques. Skin texture was quantified by calculating the change in skin texture threshold value between the first follow-up visit (day 2+/−1) and the baseline visit. A lower skin texture threshold value (i.e. closer to 0) denotes a faster recovery to baseline levels of skin texture, as it implies there is little difference between the baseline images, and the first follow-up (day 2+/−1). Kerra Rescue treated skin had significantly improved skin texture as demonstrated by a lower skin threshold value (FIG. 28). This suggests that the Kerra Rescue Regimen improves skin texture recovery following energy-based dermatological procedures.

Figure 29:
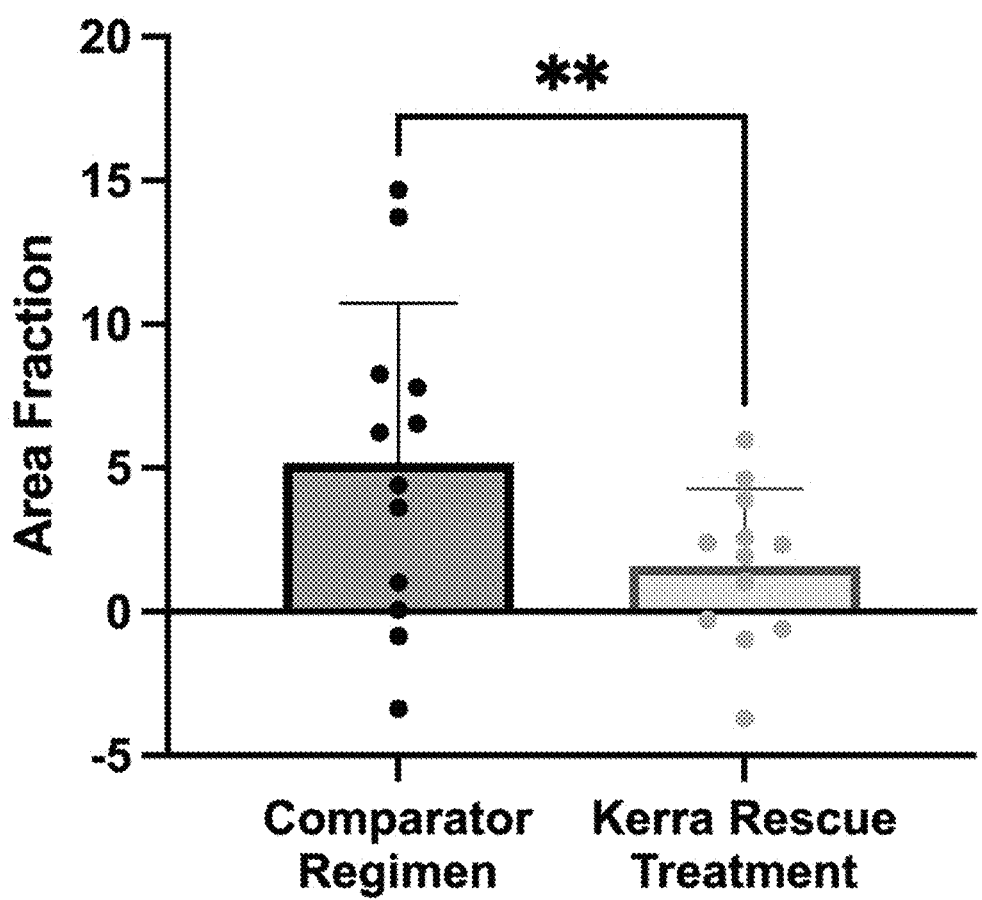
FIG. 29 is a bar graph illustrating that the Kerra Rescue Regimen significantly reduces scabbing area by day 2 following energy-based dermatological procedures, in an example of the present disclosure. Data plotted are mean+/−SD. Student t-test performed. *=p<0.05.

In addition to skin texture, change in scabbing and irritation area from the first follow-up visit to baseline was quantified. Again, a lower value denotes a faster recovery in post-procedure scabbing and irritation as it implies there is little difference between the two timepoints, and the post-procedure skin resembles baseline skin. The Kerra Rescue treated skin had significantly less scabbing area and irritation compared to the comparator regimen (FIG. 29). Taken together, these data demonstrate that the Kerra Rescue Regimen can improve post-procedure recovery by reducing skin texture, and scabbing area and irritation by 2-fold compared to the comparator regimen.

Investigator and Subject Rated Healing

Figure 30:
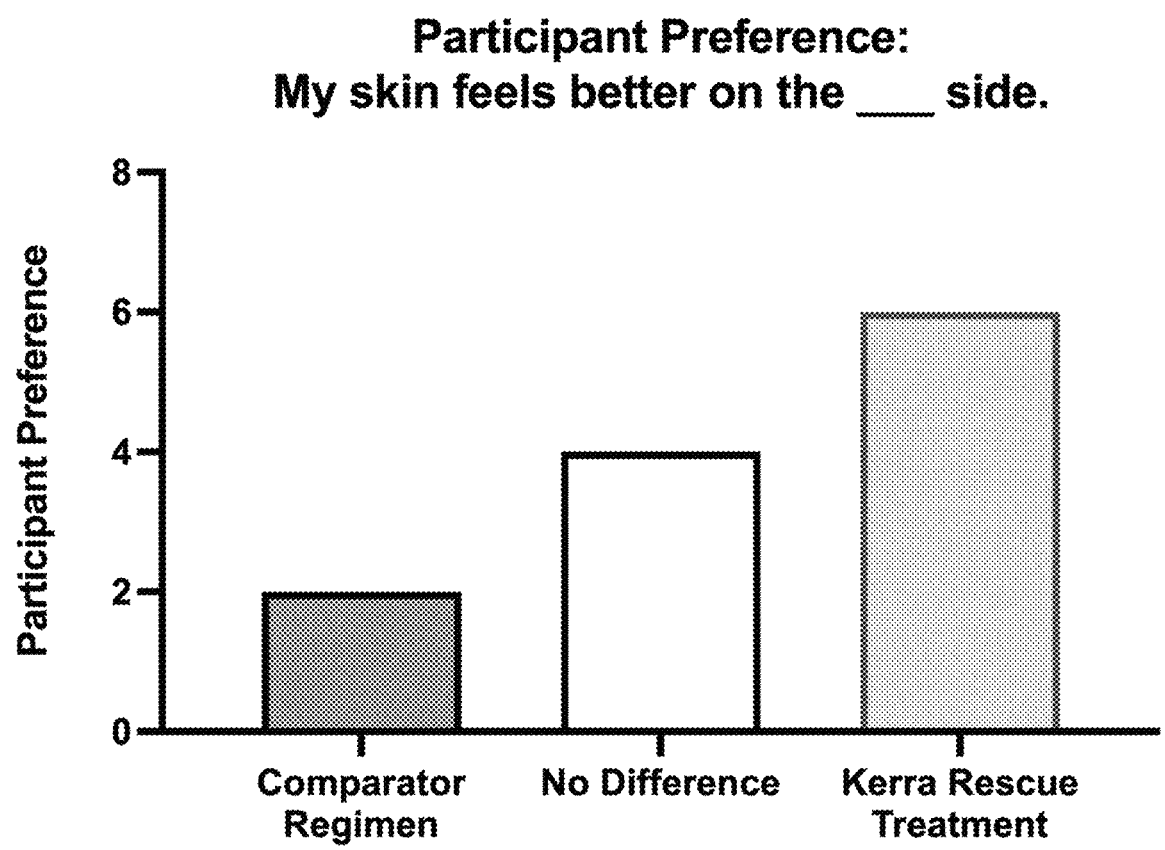
FIG. 30 is a bar graph illustrating that a majority of participants reported that the Kerra Rescue Regimen made their skin feel better during the first follow-up visit (day 2+/−1).

Subjects reported higher satisfaction with the Kerra Rescue Regimen during the first follow-up visit when asked to report on which side of their face their skin feels better (FIG. 30).

Figure 31:
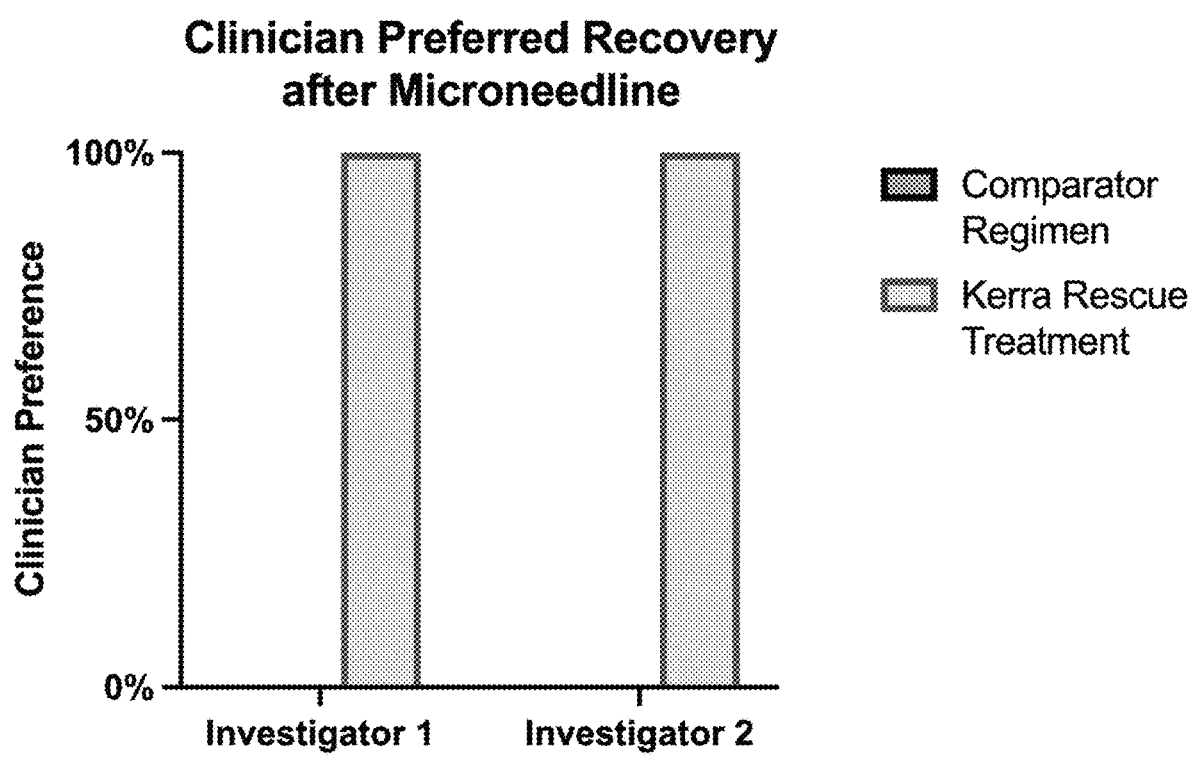
FIG. 31 is a bar graph illustrating that two blinded dermatologists consistently rated better recovery with the Kerra Rescue Regimen following microneedling procedures.

Similarly, two blinded dermatologists, independent of each other, consistently rated improved recovery in skin treated with the Kerra Rescue Regimen during the first follow-up visit in participants who received any microneedling procedure (FIG. 31).

Safety

There were no significant adverse events reported. One participant showed signs of irritant contact dermatitis on both sides of the face after the procedure. The dermatitis was treated with standard of care by the clinician.

Discussion

Although procedures such as laser resurfacing and microneedling exist for the purpose of anti-aging and skin discolouration, the recovery time is a major hinderance for many patients and clinicians. The Kerra Rescue Regimen has been designed to shorten the recovery period following these types of dermatological procedures, allowing patients to resume normal day-to-day activities quicker.

When designing a post-procedure recovery regimen, products with ingredients that have been shown to promote skin health, new collagen formation, and provide hydration were sought. Thus, the Kerra Rescue Regimen, consists of a two-step skin care process to tackle the needs of these patients. The first step, consists of the Kerra Rescue Gel, which is a hydrating gel containing the Q-Peptide system. This system has been demonstrated to promote skin cell survival and migration, new collagen production, and is anti-inflammatory (Mandla, S., et al. *ACS Biomater. Sci. Eng.* 5, 4542-4550 (2019); Xiao, Y. et al. *Proc. Natl. Acad. Sci. U.S.A* 113, E5792—E5801 (2016)). The Rescue Gel was designed to be free of dyes, lanolin, fragrances, parabens and formaldehydes such that it is a clean product, with low risk of skin irritation, and the Rescue Ointment was designed to contain petrolatum and shea butter, thereby acting as a hydrating mask.

The results from this study are the first to demonstrate the efficacy and safety of the Kerra Rescue Regimen following laser and energy-based dermatological procedures. In this study, recovery hastened at an early time point during the first post-procedure follow up visit on day 2 (+/−1 day). By day 7, all patients had recovered, and so day 2 was chosen as the comparator day for this study. Further, as this was a split-face study design and each participant received both treatments, each participant was able to act as their own control for recovery during data analysis.

By employing image analysis techniques as opposed to questionnaires alone, quantitative was captured which demonstrates the increased recovery with the Kerra Rescue Regimen. Notably, by day 2, an increase in skin recovery was observed as indicated by a greater change in skin colour and appearance. In addition, the Kerra Rescue Regimen improves the quality of skin during recovery as evidenced by a significant reduction in skin texture, and scabbing area.

In addition to a quantifiable difference in the quality of skin, participants were more satisfied with the Kerra Rescue Regimen and reported that it made their skin feel better by day 2. Finally, two blinded dermatologists, independently of each other rating improved recovery in Kerra Rescue Regimen treated skin following microneedling. Positive feedback from the blinded participants and dermatologists further supports the use of the Kerra Rescue Regimen following laser resurfacing and microneedling.

As this was a pilot study, the inclusion criteria were not limiting to capture any and all laser and energy-based procedures. However, it was important for identifying areas in which the Kerra Rescue Regimen has the greatest effect. Following the promising results of radiofrequency microneedling, future studies should include more patients undergoing deep-tissue microneedling, as well as longer patient follow-ups to track if the Kerra Rescue Regimen also helps to preserve the effects of their procedure.

There are currently few products on the market which are recommended by dermatologists following laser and energy-based dermatological treatments. As a result, patients are left to find products to use on their own, some of which can be detrimental, such as retinols. The development of a cosmetically elegant skincare routine for post-procedure skin can not only help to short recovery times, but prevent further injury, and enhance satisfaction leading to future procedures.

CONCLUSION

In this study, the Kerra Rescue Regimen was demonstrated to be a safe skincare regimen that promoted accelerated recovery and skin appearance following laser face resurfacing and microneedling. The use of this regimen may lead to increased patient satisfaction as a result of a shorted recovery time.

The present disclosure provides examples of the disclosed compositions, formulations, and methods of use of a peptide comprising an amino acid sequence of QHREDGS (SEQ ID NO: 1), for treatment or improvement of the condition and appearance of skin. These examples are provided only to help illustrate the disclosed compositions and uses thereof, and are not intended to be limiting. It should be understood that the disclosed composition and formulation may be varied within the scope of the present disclosure.

The present disclosure may be embodied in other specific forms without departing from the subject matter of the claims. The described example embodiments are to be considered in all respects as being only illustrative and not restrictive. Selected features from one or more of the above-described embodiments may be combined to create alternative embodiments not explicitly described, features suitable for such combinations being understood within the scope of this disclosure.

All values and sub-ranges within disclosed ranges are also disclosed. Also, although the systems, devices and processes disclosed and shown herein may comprise a specific number of elements/components, the systems, devices and assemblies could be modified to include additional or fewer of such elements/components. For example, although any of the elements/components disclosed may be referenced as being singular, the embodiments disclosed herein could be modified to include a plurality of such elements/components. The subject matter described herein intends to cover and embrace all suitable changes in technology.

SEQUENCE LISTING

```
Sequence total quantity: 22
SEQ ID NO: 1           moltype = AA  length = 7
FEATURE                Location/Qualifiers
REGION                 1..7
                       note = Synthetic polypeptide
source                 1..7
```

```
                        mol_type = protein
                        organism = synthetic construct
SEQUENCE: 1
QHREDGS                                                                 7

SEQ ID NO: 2            moltype = AA   length = 16
FEATURE                 Location/Qualifiers
REGION                  1..16
                        note = Synthetic polypeptide
MOD_RES                 1
                        note = ACETYLATION
MOD_RES                 16
                        note = AMIDATION
source                  1..16
                        mol_type = protein
                        organism = synthetic construct
SEQUENCE: 2
RARADADARA RADADA                                                       16

SEQ ID NO: 3            moltype = AA   length = 4
FEATURE                 Location/Qualifiers
REGION                  1..4
                        note = Synthetic Polypeptide
source                  1..4
                        mol_type = protein
                        organism = synthetic construct
SEQUENCE: 3
REDG                                                                    4

SEQ ID NO: 4            moltype = AA   length = 4
FEATURE                 Location/Qualifiers
REGION                  1..4
                        note = Synthetic Polypeptide
source                  1..4
                        mol_type = protein
                        organism = synthetic construct
SEQUENCE: 4
RLDG                                                                    4

SEQ ID NO: 5            moltype = AA   length = 5
FEATURE                 Location/Qualifiers
REGION                  1..5
                        note = Synthetic Polypeptide
source                  1..5
                        mol_type = protein
                        organism = synthetic construct
SEQUENCE: 5
REDGS                                                                   5

SEQ ID NO: 6            moltype = AA   length = 5
FEATURE                 Location/Qualifiers
REGION                  1..5
                        note = Synthetic Polypeptide
source                  1..5
                        mol_type = protein
                        organism = synthetic construct
SEQUENCE: 6
RLDGS                                                                   5

SEQ ID NO: 7            moltype = AA   length = 5
FEATURE                 Location/Qualifiers
REGION                  1..5
                        note = Synthetic Polypeptide
source                  1..5
                        mol_type = protein
                        organism = synthetic construct
SEQUENCE: 7
HREDG                                                                   5

SEQ ID NO: 8            moltype = AA   length = 5
FEATURE                 Location/Qualifiers
REGION                  1..5
                        note = Synthetic Polypeptide
source                  1..5
                        mol_type = protein
                        organism = synthetic construct
SEQUENCE: 8
HRLDG                                                                   5
```

```
SEQ ID NO: 9          moltype = AA   length = 6
FEATURE               Location/Qualifiers
REGION                1..6
                      note = Synthetic Polypeptide
source                1..6
                      mol_type = protein
                      organism = synthetic construct
SEQUENCE: 9
HREDGS                                                                    6

SEQ ID NO: 10         moltype = AA   length = 6
FEATURE               Location/Qualifiers
REGION                1..6
                      note = Synthetic Polypeptide
source                1..6
                      mol_type = protein
                      organism = synthetic construct
SEQUENCE: 10
HRLDGS                                                                    6

SEQ ID NO: 11         moltype = AA   length = 6
FEATURE               Location/Qualifiers
REGION                1..6
                      note = Synthetic Polypeptide
source                1..6
                      mol_type = protein
                      organism = synthetic construct
SEQUENCE: 11
QHREDG                                                                    6

SEQ ID NO: 12         moltype = AA   length = 6
FEATURE               Location/Qualifiers
REGION                1..6
                      note = Synthetic Polypeptide
source                1..6
                      mol_type = protein
                      organism = synthetic construct
SEQUENCE: 12
QHRLDG                                                                    6

SEQ ID NO: 13         moltype = AA   length = 7
FEATURE               Location/Qualifiers
REGION                1..7
                      note = Synthetic Polypeptide
source                1..7
                      mol_type = protein
                      organism = synthetic construct
SEQUENCE: 13
QHREDVS                                                                   7

SEQ ID NO: 14         moltype = AA   length = 7
FEATURE               Location/Qualifiers
REGION                1..7
                      note = Synthetic Polypeptide
source                1..7
                      mol_type = protein
                      organism = synthetic construct
SEQUENCE: 14
QHREDGS                                                                   7

SEQ ID NO: 15         moltype = AA   length = 7
FEATURE               Location/Qualifiers
REGION                1..7
                      note = Synthetic Polypeptide
source                1..7
                      mol_type = protein
                      organism = synthetic construct
SEQUENCE: 15
QHRLDGS                                                                   7

SEQ ID NO: 16         moltype = AA   length = 6
FEATURE               Location/Qualifiers
REGION                1..6
                      note = Synthetic Polypeptide
source                1..6
                      mol_type = protein
                      organism = synthetic construct
SEQUENCE: 16
KRLDGS                                                                    6
```

```
SEQ ID NO: 17         moltype = AA  length = 8
FEATURE               Location/Qualifiers
REGION                1..8
                      note = Synthetic Polypeptide
source                1..8
                      mol_type = protein
                      organism = synthetic construct
SEQUENCE: 17
QHREDGSL                                                              8

SEQ ID NO: 18         moltype = AA  length = 8
FEATURE               Location/Qualifiers
REGION                1..8
                      note = Synthetic Polypeptide
source                1..8
                      mol_type = protein
                      organism = synthetic construct
SEQUENCE: 18
QHRLDGSL                                                              8

SEQ ID NO: 19         moltype = AA  length = 9
FEATURE               Location/Qualifiers
REGION                1..9
                      note = Synthetic Polypeptide
source                1..9
                      mol_type = protein
                      organism = synthetic construct
SEQUENCE: 19
QHRLDGSLD                                                             9

SEQ ID NO: 20         moltype = AA  length = 9
FEATURE               Location/Qualifiers
REGION                1..9
                      note = Synthetic Polypeptide
source                1..9
                      mol_type = protein
                      organism = synthetic construct
SEQUENCE: 20
QHREDGSLD                                                             9

SEQ ID NO: 21         moltype =    length =
SEQUENCE: 21
000

SEQ ID NO: 22         moltype = AA  length = 7
FEATURE               Location/Qualifiers
REGION                1..7
                      note = Synthetic Polypeptide
source                1..7
                      mol_type = protein
                      organism = synthetic construct
SEQUENCE: 22
QHREDGS                                                               7
```

The invention claimed is:

1. A method of improving a cosmetic condition or aesthetic appearance of skin on a subject, the method comprising: topically administering to the skin of the subject in need thereof, a formulation comprising a peptide comprising an amino acid sequence of QHREDGS (SEQ ID NO: 1), in an amount effective to improve the cosmetic condition or aesthetic appearance of the skin, wherein the improvement of the cosmetic condition or aesthetic appearance of the skin is at least one of: reducing dermatological signs of chronological aging, photo-aging, hormonal aging, or actinic aging; reducing the appearance of lines or wrinkles; reducing noticeability of facial lines and wrinkles, facial wrinkles on cheeks, forehead, perpendicular wrinkles between eyes, horizontal wrinkles above eyes, and around mouth, marionette lines; reducing, or diminishing the appearance or depth of lines or wrinkles; improving the appearance of suborbital lines or periorbital lines; reducing the appearance of crow's feet; rejuvenating or revitalizing skin; reducing skin fragility; reversing of loss of glycosaminoglycans or collagen; ameliorating effects of estrogen imbalance; skin atrophy; reducing, or treating hyperpigmentation; minimizing skin discoloration; improving skin tone, radiance, clarity or tautness; reducing, or ameliorating skin sagging; improving skin firmness, plumpness, suppleness or softness; improving procollagen or collagen production; improving skin texture or promoting retexturization; improving skin barrier repair or function; improving the appearance of skin contours; restoring skin luster and/or brightness; minimizing dermatological sings of fatigue or stress; resisting environmental stress; replenishing ingredients in the skin decreased by aging or menopause; improving communication among skin cells; increasing cell proliferation or multiplication; increasing skin cell metabolism decreased by aging or menopause; retarding cellular aging, improving skin moisturization; enhancing skin thickness; increasing skin elasticity or resiliency; enhancing exfoliation; improving microcirculation; or decreasing cellulite formation.

2. The method of claim 1, wherein the improvement of the cosmetic condition or aesthetic appearance of the skin further includes decreasing skin redness in the subject, the amount of formulation administered being effective to decrease skin redness.

3. The method of claim 2, wherein the skin redness results from acne, contact irritation, skin sensitivity, rosacea, eczema, surgery, laser treatment, allergies, microdermabrasion, dermabrasion, or any combination thereof.

4. The method of claim 1, wherein the formulation further comprises a topically acceptable vehicle.

5. The method of claim 4, wherein the topically acceptable vehicle is selected from hydroxyethyl cellulose, hydroxypropyl cellulose, methylcellulose, hydroxypropyl methylcellulose, sodium hyaluronate, hyaluronic acid, sodium carbomer, aloe gel, xanthan gum, cetyl alcohol, cetearyl alcohol, propanediol 1,3 glycerin, rosehip oil, shea butter, jojoba oil, castor oil, macadamia oil, argan oil, kukui nut oil, petrolatum, mineral oil, evening primrose oil, glyceryl stearate, Polysorbate 60, Cetearyl Olivate, Sorbitan Olivate, Sodium Stearyl Lactylate, Stearic Acid, PEG 100 Stearate, Benzyl Alcohol, Ethylhexylglycerin, Benzoic Acid, Sorbic Acid, Gluconolactone, Sodium Benzoate, Calcium Gluconate, and any combinations thereof.

6. The method of claim 1, wherein the formulation further comprises a carrier.

7. The method of claim 6, wherein the carrier is selected from the group consisting of hydrogel, glycerol, propylene glycol, chitosan, alginate, agarose, polyether, polyesters, methylcellulose, hyaluronan, collagen, laminin, matrigel, fibronectin, vitronectin, poly-l-lysine, proteoglycans, fibrin glue, gels made by decellularization of engineered and natural tissues, polyglycolic acid (PGA), polylactic acid (PLA) and combinations of PGA and PLA, poly(lactic-co-glycolic) acid (PLGA), poly ε-caprolactone, polyvinyl alcohol (PVA), polyethylene glycol (PEG), methyl methacrylate, poly(methyl methacrylate) (PMMA), poly(2-hydroxyethyl methacrylate) (Poly-HEMA), poly(glycerol sebacate), self-assembling peptide hydrogels, RARADADARARADADA (SEQ ID NO: 2), polyurethanes, poly(isopropylacrylamide), poly(N-isopropylacrylamide) (poly(NIPAM)), and any combinations thereof.

8. The method of claim 7, wherein the peptide is conjugated to the carrier.

9. The method of claim 7, wherein the formulation comprises 0.5-50 wt % carrier.

10. The method of claim 7, wherein the formulation comprises 0.02-2 wt % collagen.

11. The method of claim 1, wherein the formulation further comprises 0.001-1 wt % peptide.

12. The method of claim 1, wherein the formulation is in a form of a gel, a tincture, a cream, a cream, an ointment, a lotion, or an aerosol spray.

13. A method of improving a cosmetic condition or aesthetic appearance of skin on a subject, the method comprising: topically administering to the skin of the subject in need thereof, a formulation comprising a peptide comprising an amino acid sequence of QHREDGS (SEQ ID NO: 1), in an amount effective to improve the cosmetic condition or aesthetic appearance of the skin, wherein the improvement of the cosmetic condition or aesthetic appearance of the skin is reducing a dermatological signs of chronological aging selected from a group consisting of rhytids, wrinkles, jowls, sun damage, dull appearance of skin, loss of skin tautness, keratosis, hyperpigmentation, melasma, solar lentigo, solar keratosis, dermatoheliosis, skin discoloration, and any combinations thereof.

14. The method of claim 13, wherein the formulation further comprises a topically acceptable vehicle selected from hydroxyethyl cellulose, hydroxypropyl cellulose, methylcellulose, hydroxypropyl methylcellulose, sodium hyaluronate, hyaluronic acid, sodium carbomer, aloe gel, xanthan gum, cetyl alcohol, cetearyl alcohol, propanediol 1,3 glycerin, rosehip oil, shea butter, jojoba oil, castor oil, macadamia oil, argan oil, kukui nut oil, petrolatum, mineral oil, evening primrose oil, glyceryl stearate, Polysorbate 60, Cetearyl Olivate, Sorbitan Olivate, Sodium Stearyl Lactylate, Stearic Acid, PEG 100 Stearate, Benzyl Alcohol, Ethylhexylglycerin, Benzoic Acid, Sorbic Acid, Gluconolactone, Sodium Benzoate, Calcium Gluconate, and any combinations thereof.

15. The method of claim 13, wherein the carrier is selected from the group consisting of hydrogel, glycerol, propylene glycol, chitosan, alginate, agarose, polyether, polyesters, methylcellulose, hyaluronan, collagen, laminin, matrigel, fibronectin, vitronectin, poly-l-lysine, proteoglycans, fibrin glue, gels made by decellularization of engineered and natural tissues, polyglycolic acid (PGA), polylactic acid (PLA) and combinations of PGA and PLA, poly(lactic-co-glycolic) acid (PLGA), poly ε-caprolactone, polyvinyl alcohol (PVA), polyethylene glycol (PEG), methyl methacrylate, poly(methyl methacrylate) (PMMA), poly(2-hydroxyethyl methacrylate) (Poly-HEMA), poly(glycerol sebacate), self-assembling peptide hydrogels, RARADADARARADADA (SEQ ID NO: 2), polyurethanes, poly(isopropylacrylamide), poly(N-isopropylacrylamide) (poly(NIPAM)), and any combinations thereof.

16. The method of claim 15, wherein the peptide is conjugated to the carrier.

17. The method of claim 13, wherein the formulation is in a form of a gel, a tincture, a cream, an ointment, a lotion, or an aerosol spray.

18. The method of claim 13, wherein the formulation comprises 0.001-1 wt % peptide.

19. A method of improving a cosmetic condition or aesthetic appearance of skin on a subject, the method comprising: topically administering to the skin of the subject in need thereof, a formulation comprising a peptide comprising an amino acid sequence of QHREDGS (SEQ ID NO: 1), in an amount effective to improve the cosmetic condition or aesthetic appearance of the skin, wherein the improvement of the cosmetic condition or aesthetic appearance of the skin is regenerating collagen in a skin area of the subject, the amount of formulation administered being effective to regenerate collagen in the skin area.

20. A method of improving a cosmetic condition or aesthetic appearance of skin on a subject, the method comprising: topically administering to the skin of the subject in need thereof, a formulation comprising a peptide comprising an amino acid sequence of QHREDGS (SEQ ID NO: 1), in an amount effective to improve the cosmetic condition or aesthetic appearance of the skin, wherein the improvement of the cosmetic condition or aesthetic appearance of the skin is decreasing wrinkles in the subject, the amount of the formulation administered being effective to decrease wrinkles.

* * * * *